(12) United States Patent
Karnik

(10) Patent No.: US 8,796,282 B2
(45) Date of Patent: Aug. 5, 2014

(54) METHOD OF TREATING DERMATOLOGICAL DISORDERS

(75) Inventor: Pratima Karnik, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 1564 days.

(21) Appl. No.: 12/057,649

(22) Filed: Mar. 28, 2008

(65) Prior Publication Data

US 2009/0042909 A1 Feb. 12, 2009

Related U.S. Application Data

(60) Provisional application No. 60/908,541, filed on Mar. 28, 2007.

(51) Int. Cl.
*A01N 43/54* (2006.01)

(52) U.S. Cl.
USPC .......................................... 514/256

(58) Field of Classification Search
USPC .......................................... 514/256
See application file for complete search history.

(56) References Cited

U.S. PATENT DOCUMENTS 6,395,784 B1 * 5/2002 Ryono ........................... 514/563
7,105,573 B2 * 9/2006 Krajcik et al. ................. 514/635

OTHER PUBLICATIONS

Healthcommunities.com (Retrieved on Apr. 27, 2011 from the Internet: <URL: http://www.dermatologychannel.net/alopecia/lichen_planopilaris.shtml).*
Olsen (J Investig Dermatol Symp Proc, vol. 10, pp. 217-221; 2005).*
Sachs et al. (Arch Derm Syphilol, vol. 45, No. 6, Abstract; 1942).*
Clarke et al. (Clin Nutr, vol. 70, pp. 566-571; 1999).*
Nigam et al. (British Journal of Dermatology, vol. 119, Issue 1, pp. 128 and 129; 2006).*
Clough et al. (J Histochem Cytochem, vol. 53, No. 5, abstract; 2005).*

* cited by examiner

*Primary Examiner* — Raymond Henley, III
(74) *Attorney, Agent, or Firm* — Tarolli, Sundheim, Covell & Tummino LLP

(57) ABSTRACT

A method of treating a dermatological disorder in a subject includes the step of administering a therapeutically effective amount of at least one PPARγ agonist or derivative thereof to the subject.

30 Claims, 20 Drawing Sheets

METHOD OF TREATING DERMATOLOGICAL DISORDERS

RELATED APPLICATION

This application claims priority from U.S. Provisional Application No. 60/908,541, filed Mar. 28, 2007, the subject matter, which is incorporated herein by reference.

TECHNICAL FIELD

The present invention generally relates to a method of treating a dermatological disorder in a subject, and more particularly to a method of treating a dermatological disorder in a subject by topically administering a therapeutically effective amount of at least one peroxisome proliferator-activated receptor γ agonist or derivative thereof to the subject.

BACKGROUND OF THE INVENTION

Cicatricial or scarring alopecia are a diverse group of hair disorders that cause permanent destruction of the hair follicle. There are two broad categories of cicatricial alopecia (CA): those in which hair follicles are destroyed non-specifically by processes such as thermal burns, metastatic cancer, trauma, radiation, etc.; and those in which the follicles are the primary target of a destructive inflammatory process. The latter category is termed primary CA.

Primary CA is characterized by a folliculocentric inflammatory cell infiltrate with ultimate replacement of the follicle with fibrous tissue and progressive and permanent hair loss. The failure of affected follicles to re-grow is thought to be because of destructive inflammatory changes in the region of the follicular bulge where the sebaceous gland and hair follicle stem cells are located. If the stem cells are destroyed, then there is no possibility for hair follicle regeneration and permanent hair loss ensues. Depending on the inflammatory cells detected during the active phase of the disease, the primary CAs are classified as lymphocytic, neutrophilic, or mixed.

Sebaceous glands are appendages connected to the hair follicle to form the pilosebaceous unit and secrete a unique mixture of lipids known as sebum comprised of triacylglycerols/triglycerides, cholesterol, sterol esters and phospholipids. Sebum is thought to facilitate the coordinated breakdown of the inner root sheath during the hair cycle. The sebaceous gland is a common victim along with the hair follicle in lichen planopilaris (LPP); however, the extent of sebaceous gland atrophy varies in different patients. The molecular mechanisms that link sebaceous gland atrophy, inflammation, and scarring alopecia have not yet been delineated.

Peroxisome proliferator-activated receptors (PPARs)—which include PPARγ, PPARα and PPARδ—are members of the nuclear receptor supergene family that regulate the expression of genes involved in inflammation and lipid homeostasis. They exhibit unique expression patterns within vertebrate tissues and are central regulators of gene expression and differentiation in several cell and tissue types including adipose cells, skin, sebaceous glands, muscle, liver and macrophages. PPARγ plays an important role in the sebaceous gland, inducing differentiation of sebocytes and interfering with many components of the inflammatory response by altering the expression of cytokines, receptors, and adhesion molecules.

The etiology and pathogenesis of the primary CAs remain poorly understood. Histologically, the primary CAs are marked by extensive perifollicular inflammatory infiltrates, including macrophages and either lymphocytes or neutrophil granulocytes. The inflammatory process predominately occurs around the permanent portion of the hair follicle, thereby resulting in irreversible destruction of hair follicles. Patients with primary CA are faced with a disfiguring disease that results in progressive and permanent hair loss. In addition, patients often have severe symptoms of scalp itching, burning and pain.

SUMMARY OF THE INVENTION

The present invention generally relates to a method of treating a dermatological disorder in a subject, and more particularly to a method of treating a dermatological disorder in a subject by administering a therapeutically effective amount of at least one peroxisome proliferator-activated receptor γ (PPARγ) agonist or derivative thereof to the subject.

In one aspect of the present invention, a method of treating a dermatological disorder in a subject comprises the step of topically administering a therapeutically effective amount of at least one PPARγ agonist or derivative thereof to the subject.

In another aspect of the present invention, a method of treating at least one primary cicatricial alopecia in a subject comprises the step of topically administering a therapeutically effective amount of at least one PPARγ agonist or derivative thereof to the subject.

and in the ORS and IRS surrounding the hair shaft (HS). LPP tissue (LPP1-LPP5) from 5 different patients showed a complete lack of staining for peroxisomes in the sebaceous glands and in the ORS and IRS cells surrounding the hair shaft suggesting loss of peroxisome biogenesis. An isotype control of normal tissue is also shown.

Figure 16:
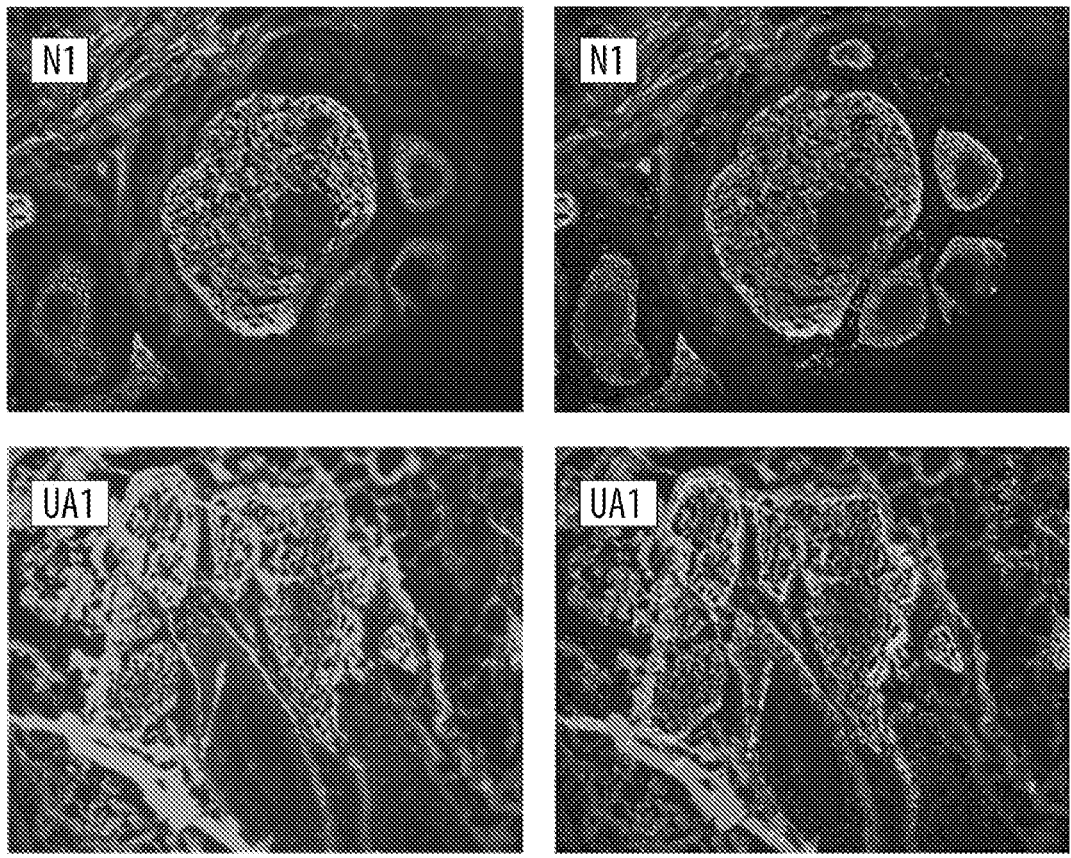

FIG. 16 illustrates in normal scalp tissue (N1), abundant peroxisome staining is seen in the sebaceous glands (SG) and in the ORS and IRS surrounding the hair shaft. b) In unaffected tissue (UA1) peroxisome staining is lost in the ORS and IRS cells surrounding the hair shaft but not in sebaceous glands. Double staining the unaffected tissue section (bottom, right panel) for peroxisomes and nuclei (DAPI) shows that the ORS and IRS cells around the hair shaft are intact but they have specifically lost peroxisomes.

Figure 17:
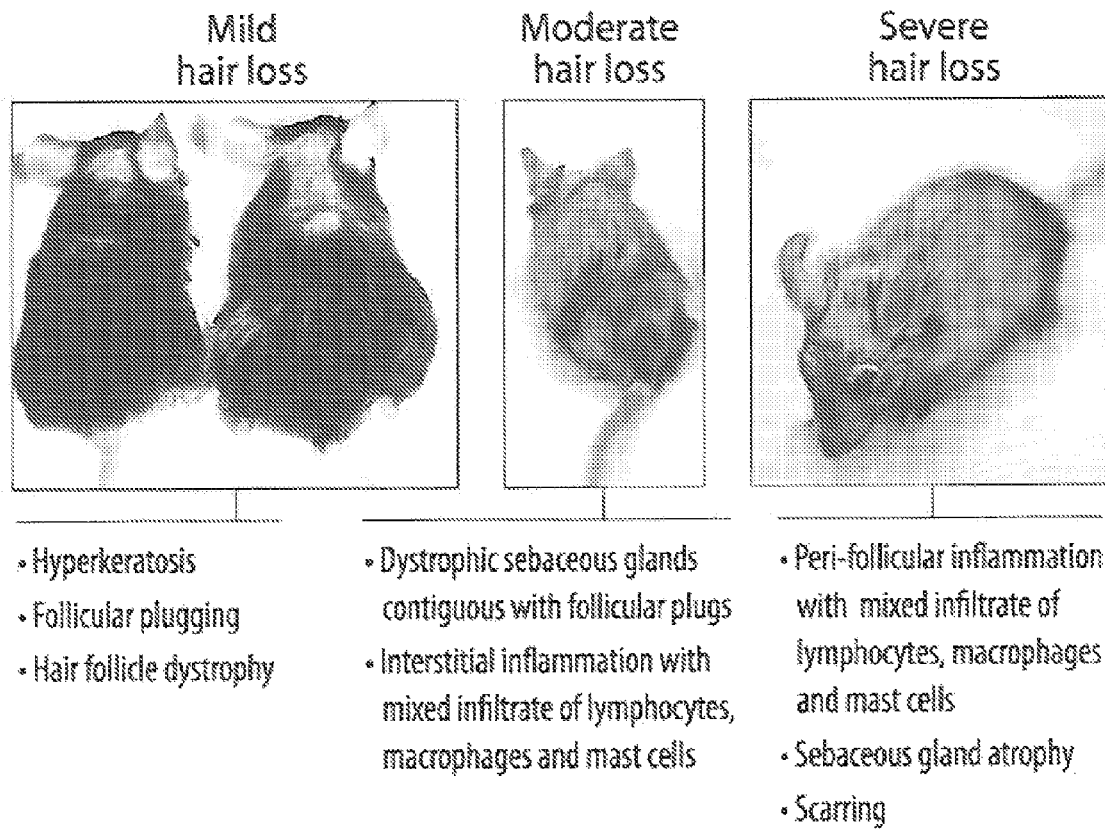

FIG. 17 illustrates scarring alopecia disease progression in PPARγ$^{fl/fl}$/Cre mice. H&E staining revealed hyperkeratosis, follicular plugging in mice with mild hair loss. Dystrophic sebaceous glands and increased interstitial inflammation in the form of macrophages, mast cells and T-lymphocytes was seen in animals with moderate hair loss. The animals with severe hair loss showed a dense lymphocytic infiltrate of t cells, some macrophages and mast cells. Sebaceous gland atrophy and scarring was also commonly seen. These data suggest that these stem cell specific knockout of PPARγ causes scarring alopecia.

Figure 18:
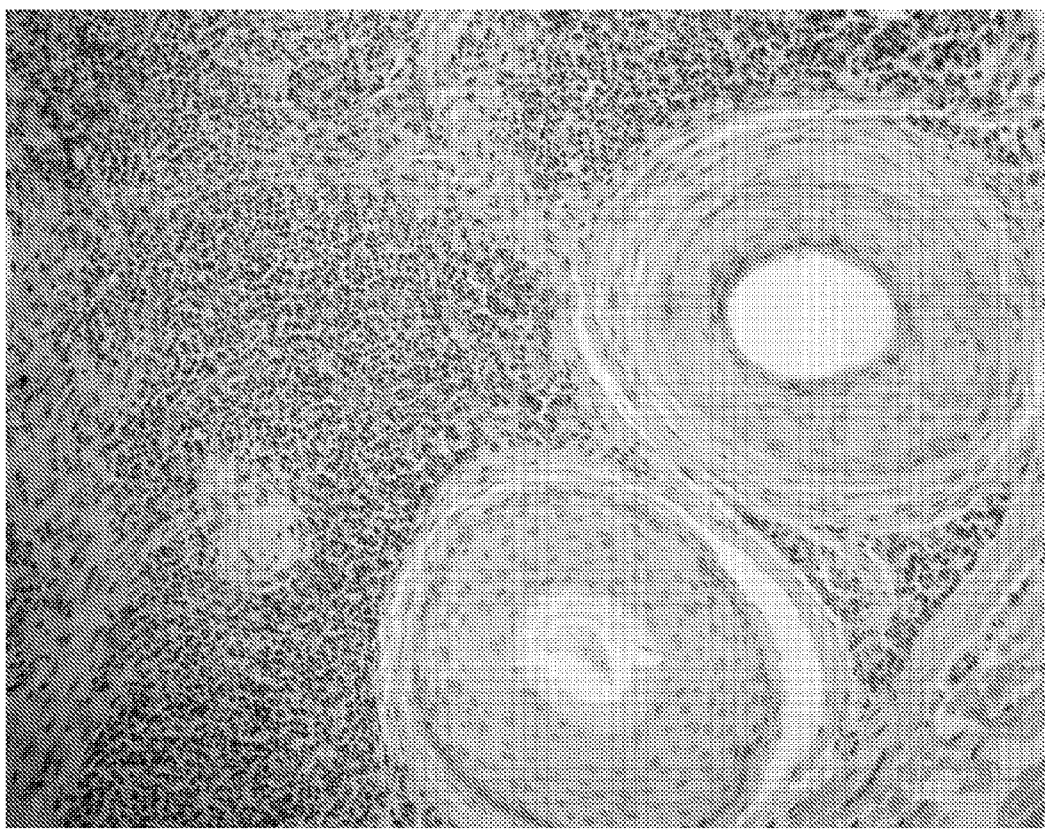

FIG. 18 illustrates before Actos LLP H and E staining of scalp biopsy magnificence (40×) of LLP patient before Actos treatment.

Figure 19:
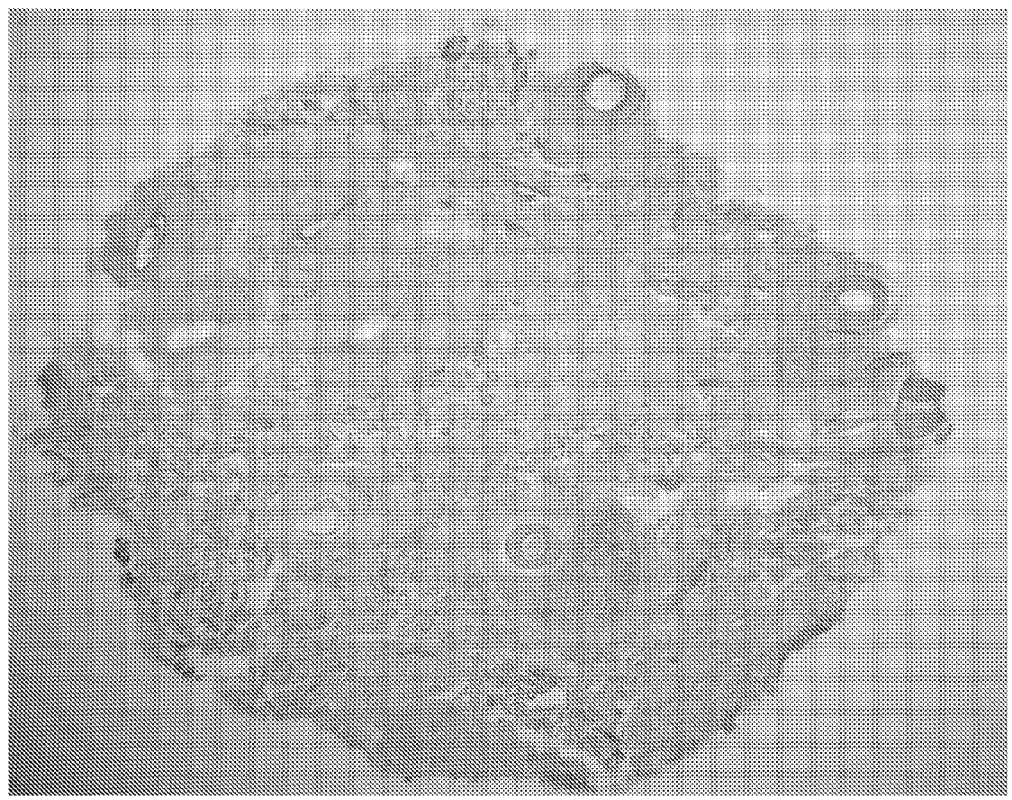

FIG. 19 illustrates after one year of treatment Hematoxylin-Eosin (H and E) staining of horizontal magnificence (20×) section of scalp biopsy of a patient with Lichen Planopilaris. Blue staining cells represent inflammatory T cells, inflammation seen in and around Sebaceous glands and hair follicles.

Figure 20:
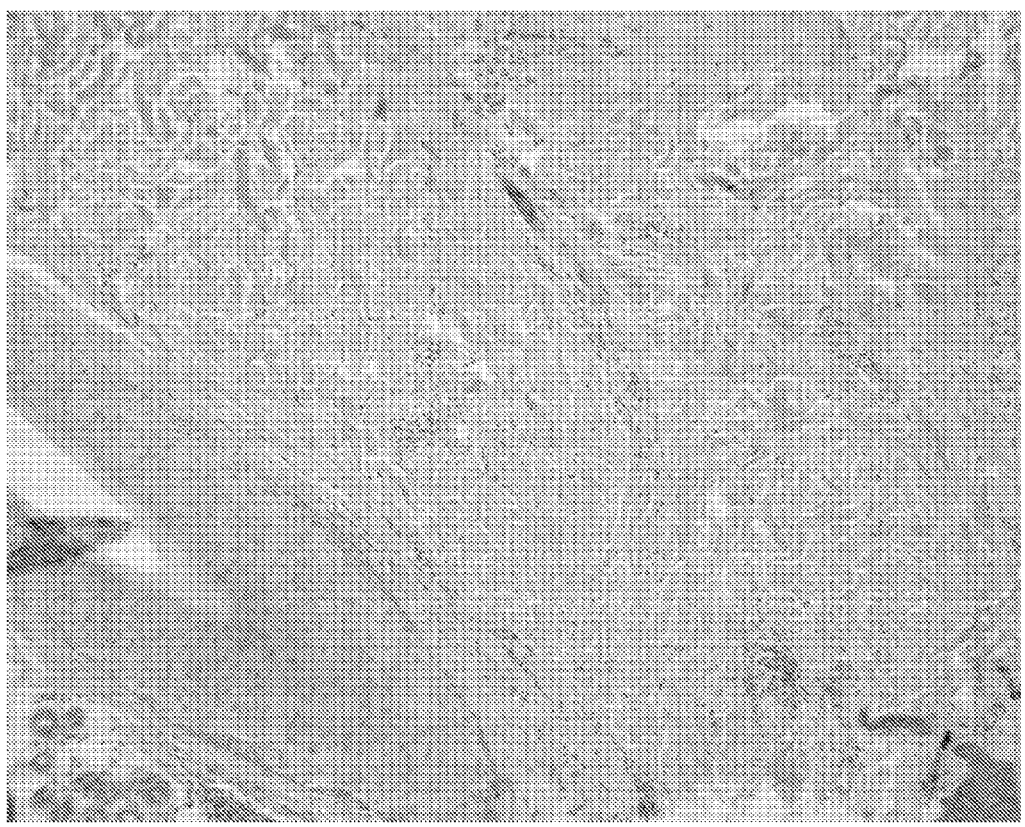

FIG. 20 illustrates after two years at a higher magnification Hematoxylin-Eosin (H and E) staining of horizontal magnificence (20×) section of scalp biopsy of a patient with Lichen Planopilaris. Blue staining cells represent inflammatory T cells, inflammation seen in and around Sebaceous glands and hair follicles.

DETAILED DESCRIPTION

The present invention generally relates to a method of treating a dermatological disorder in a subject, and more particularly to a method of treating a dermatological disorder in a subject by administering a therapeutically effective amount of at least one peroxisome proliferator-activated receptor γ (PPARγ) agonist or derivative thereof to the subject. The present invention is based on the discovery that there are multiple alterations in gene expression required for cellular lipid metabolism and peroxisome biogenesis in subjects with lichen planopilaris (LPP). More particularly, the present invention is based on the discovery that the specific PPARγ agonist rosiglitazone induces the expression of the peroxisomal genes peroxisomal biogenesis factor 3 (PEX3), peroxisomal biogenesis factor 16 (PEX16), and peroxisomal membrane protein (PMP22) (collectively, "PEX genes"), as well as numerous matrix protein genes for enzymes of fatty acid β-oxidation and desaturation. Based on these discoveries, the present invention provides a method of treating dermatological disorders, such as primary cicatricial alopecias (CAs), by topically administering a therapeutically effective amount of at least one PPARγ agonist or derivative thereof to a subject.

Unless otherwise defined, all technical terms used herein have the same meaning as commonly understood by one of ordinary skill in the art to which the present invention pertains.

In the context of the present invention, the term "therapeutically effective amount" refers to that amount of a composition that results in amelioration of symptoms or a prolongation of survival in a subject. A therapeutically relevant effect relieves to some extent one or more symptoms of a disease or condition or returns to normal either partially or completely one or more physiological or biochemical parameters associated with or causative of the disease or condition.

As used herein, the term "PPARγ agonist" refers to a compound or composition, which when combined with PPARγ, directly or indirectly stimulates or increases an in vivo or in vitro reaction typical for the receptor (e.g., transcriptional regulation activity). The increased reaction can be measured by any of a variety of assays known to those skilled in the art. An example of a PPARγ agonist is a thiazolidinedione compound, such as troglitazone, rosiglitazone, pioglitazone, ciglitazone, WAY-120,744, englitazone, AD 5075, darglitazone, and congeners, analogs, derivatives, and pharmaceutically acceptable salts thereof.

As used herein, the term "subject" refers to any animal, including, but not limited to, humans and non-human animals (e.g., rodents, arthropods, insects, fish (e.g., zebrafish), non-human primates, ovines, bovines, ruminants, lagomorphs, porcines, caprines, equines, canines, felines, aves, etc.), which is to be the recipient of a particular treatment. Typically, the terms "patient" and "subject" are used interchangeably herein in reference to a human subject.

As used herein, the term "agonist" refers to a molecule which, when interacting with a biologically active molecule, causes a change (e.g., enhancement) in the biologically active molecule, which modulates the activity of the biologically active molecule.

As used herein, the term "modulate" refers to a change in the biological activity of a biologically active molecule. Modulation can be an increase or a decrease in activity, a change in binding characteristics, or any other change in the biological, functional, or immunological properties of biologically active molecules.

As used herein, the term "in vitro" refers to an artificial environment and to processes or reactions that occur within an artificial environment. In vitro environments consist of, but are not limited to, test tubes and cell culture. The term "in vivo" refers to the natural environment (e.g., an animal or a cell) and to processes or reaction that occur within a natural environment.

As used herein, the term "dermatological disorder" refers to any disorder of skin, hair, or glands. A dermatological disorder can be manifest in the form of visible lesions, pre-emergent lesions, pain, sensitivity to touch, irritation, inflammation, or the like. Dermatological disorders include disorders of the cutaneous and pilosebaceous unit or the process of keratogenesis. For example, a dermatological disorder can be a disorder of the epidermis or dermis, or within and surrounding a pilosebaceous unit, which is located within the epidermis, dermis, subcutaneous layer, or a combination thereof. Examples of dermatological disorders include, but are not limited to, acne, alopecia, psoriasis, seborrhea, ingrown hairs and pseudofolliculitis barbae, hyperpigmented skin, cutaneous infections, lichen planus, Graham Little Syndrome, periorificial dermatitis, rosacea, hidradenitis suppurativa, dissecting cellulitis, systemic lupus erythematosus, discoid lupus erythematosus, and the like.

As used herein, the terms "treating" or "treatment" of a condition or disease includes: (1) preventing at least one symptom of the conditions, i.e., causing a clinical symptom to not significantly develop in a subject that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms. Treatment, prevention, and ameliorating a condition, as used herein, can include, for example decreasing or inhibiting hair loss associated with a dermatological disorder.

As used herein, the term "alopecia" refers to partial or full baldness, hair loss, and/or hair thinning.

As used herein, the term "primary cicatricial alopecia" refers to a group of hair disorders that cause permanent destruction of the hair follicle. The term includes hair disorders in which the hair follicles are the primary target of a destructive inflammatory process. Cicatricial alopecias can be classified as lymphocytic, neutrophilic, and combinations thereof (i.e., "mixed"). Examples of lymphocytic CAs include lichen planopilaris, frontal fibrosing alopecia, chronic cutaneous lupus, erythematosus, pseudopelade, central centrifugal alopecia, alopecia mucinosa, and keratosis follicularis spinulosadecalvans. Examples of neutrophilic CAs include folliculitis decalvans, tufted folliculitis, and dissecting cellulitis. Examples of mixed CAs include follicullitis keloidalis and erosive dermatosis.

Although it is not necessary to understand the mechanisms in order to practice the present invention, and it is not intended that the present invention be so limited, it is shown by the present invention that: (1) PPARγ-regulated gene expression is decreased in LPP; (2) genes associated with lipid metabolism exhibit decreased expression in LPP; (3) lipid accumulation is abnormally high in the extracellular region of the perifolliculum in LPP; (4) PEX gene expression is down-regulated in LPP; and (5) exposure to rosiglitazone produces a three-fold increase in PEX gene expression in a human keratocyte cell line. From this, it is believed that increasing PPARγ expression with specific PPARγ agonists can induce peroxisomal and lipid-metabolic gene expression in subjects with dermatological disorders, such as LPP, and thus serve as an effective treatment for such disorders.

In an aspect of the present invention, a method is provided for treating a dermatological disorder in a subject. The method comprises the step of administering a therapeutically effective amount of at least one PPARγ agonist or derivative thereof to the subject. The PPARγ agonists can include, for example, prostaglandin J2 (PGJ2) and analogs thereof (e.g., A2-prostaglandin J2 and 15-deoxy-2,4-prostaglandin J2), members of the prostaglandin D2 family of compounds, docosahexaenoic acid (DHA), and thiazolidinediones (e.g., ciglitazone, troglitazone, pioglitazone and rosiglitazone).

In addition, such PPARγ agonists can include, but are not limited to, L-tyrosine-based compounds, farglitazar, GW7845, indole-derived compounds, indole 5-carboxylic acid derivatives and 2,3-disubstituted indole 5-phenylacetic acid derivatives. It is significant that most of the PPARγ agonists exhibit substantial bioavailability following oral administration and have little or no toxicity associated with their use (See, e.g., Saltiel and Olefsky, Diabetes 45:1661 (1996); Wang et a1., Br. J. Pharmacol. 122:1405 (1997); and Oakes et al., Metabolism 46:935 (1997)). It will be appreciated that the present invention is not limited to above-identified PPARγ agonists and that other identified PPARγ agonists can also be used.

PPARγ agonists that can be used for practicing the present invention, and methods of making these compounds, are disclosed in WO 91/07107; WO 92/02520; WO 94/01433; WO 89/08651; WO 96/33724; WO 97/31907; U.S. Pat. Nos. 4,287,200; 4,340,605; 4,438,141; 4,444,779; 4,461,902; 4,572,912; 4,687,777; 4,703,052; 4,725,610; 4,873,255; 4,897,393; 4,897,405; 4,918,091; 4,948,900; 5,002,953; 5,061,717; 5,120,754; 5,132,317; 5,194,443; 5,223,522; 5,232,925; 5,260,445; 5,814,647; 5,902,726; 5,994,554; 6,294,580; 6,306,854; 6,498,174; 6,506,781; 6,541,492; 6,552,055; 6,579,893; 6,586,455, 6,660,716, 6,673,823; 6,680,387; 6,768,008; 6,787,551; 6,849,741; 6,878,749; 6,958,355; 6,960,604; 7,022,722; and U.S. Applications 20030130306, 20030134885, 20030109579, 20030109560, 20030088103, 20030087902, 20030096846, 20030092697, 20030087935, 20030082631, 20030078288, 20030073862, 20030055265, 20030045553, 1 20020169192, 20020165282, 20020160997, 20020128260, 20020103188, 20020082292, 20030092736, 20030069275, 20020151569, and 20030064935.

The disclosures of these publications are incorporated herein by reference in their entireties, especially with respect to the PPARγ agonists disclosed therein, which may be employed in the methods described herein.

As PPARγ agonists having the aforementioned effects, the compounds of the following formulas are useful in treating subjects. Accordingly, in some embodiments of the present invention, the PPARγ agonists can comprise compounds of Formula I:

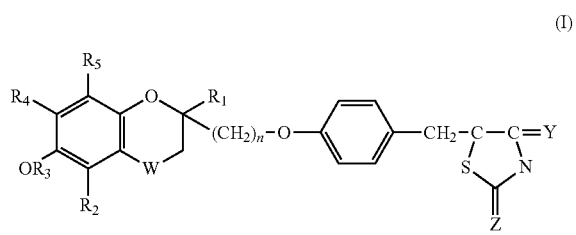

(I)

wherein $R_1$ and $R_2$ are the same or different, and each represents a hydrogen atom or a $C_1$-$C_5$ alkyl group; $R_3$ represents a hydrogen atom, a $C_1$-$C_6$ aliphatic acyl group, an alicyclic acyl group, an aromatic acyl group, a heterocyclic acyl group, an araliphatic acyl group, a ($C_1$-$C_6$ alkoxy)carbonyl group, or an aralkyloxycarbonyl group; $R_4$ and $R_5$ are the same or different, and each represents a hydrogen atom, a $C_1$-$C_5$ alkyl group or a $C_1$-$C_5$ alkoxy group, or $R_4$ and $R_5$ together represent a $C_1$-$C_5$ alkylenedioxy group; n is 1, 2, or 3; W represents the $CH_2$, CO, or $CHOR_6$ group (in which $R_6$ represents any one of the atoms or groups defined for $R_3$ and may be the same as or different, from $R_3$); and Y and Z are the same or different and each represents an oxygen atom or an imino (—NH) group; and pharmaceutically acceptable salts thereof.

In some embodiments of the present invention, the PPARγ agonists can comprise compounds of Formula II:

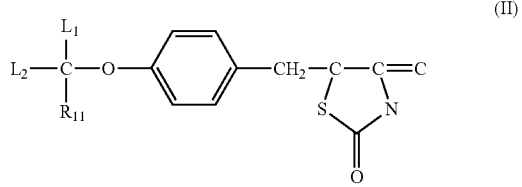

(II)

wherein $R_{11}$ is a substituted or unsubstituted alkyl, alkoxy, cycloalkyl, phenylalkyl, phenyl, aromatic acyl group, a 5- or 6 membered heterocyclic group including 1 or 2 heteroatoms selected from the group consisting of nitrogen, oxygen, and sulfur, or a group of the formula indicated in:

wherein $R_{13}$ and $R_{14}$ are the same or different and each is a lower alkyl (alternately, $R_{13}$ and $R_{14}$ are combined to each other either directly or as interrupted by a heteroatom comprising nitrogen, oxygen, and sulfur to form a 5- or 6-membered ring); and wherein $L^1$ and $L^2$ are the same or different and each is hydrogen or lower alkyl or $L^1$ and $L^2$ are combined to form an alkylene group; or a pharmaceutically acceptable salt thereof.

In some aspects of the present invention, the PPARγ agonists can comprise compounds of Formula III:

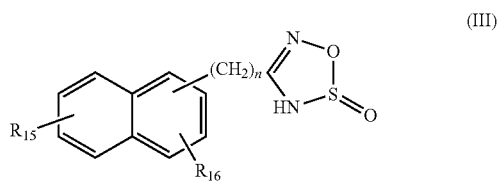
(III)

wherein $R_{15}$ and $R_{16}$ are independently hydrogen, lower alkyl containing 1 to 6 carbon atoms, alkoxy containing 1 to 6 carbon atoms, halogen, ethyl, nitrite, methylthio, trifluoromethyl, vinyl, nitro, or halogen substituted benzyloxy; n is 0 to 4; or a pharmaceutically acceptable salt thereof.

In some aspects of the present invention, the PPARγ agonists can comprise compounds of Formula IV:

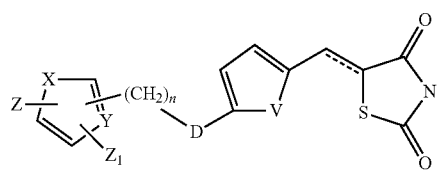
(IV)

wherein the dotted line represents a bond or no bond; V is HCH—, —NCH—, —CH=N—, or S; D is $CH_2$, CHOH, CO, C=NOR$_{17}$, or CH=CH; X is S, SO, NR$_{18}$, —CH=N, or —N=CH; Y is CH or N; Z is hydrogen, $(C_1-C_7)$alkyl, $(C_1-C_7)$cycloalkyl, phenyl, naphthyl, pyridyl, furyl, thienyl, or phenyl mono- or di-substituted with the same or different groups which are $(C_1-C_3)$alkyl, trifluoromethyl, $(C_1-C_3)$alkoxy, fluoro, chloro, or bromo; $Z_1$ is hydrogen or $(C_1-C_3)$ alkyl; $R_{17}$ and $R_{18}$ are each independently hydrogen or methyl; and n is 1, 2, or 3; the pharmaceutically acceptable cationic salts thereof; and the pharmaceutically acceptable acid addition salts thereof when the compound contains a basic nitrogen.

In some embodiments of the present invention, the PPARγ agonists can comprise compounds of Formula V:

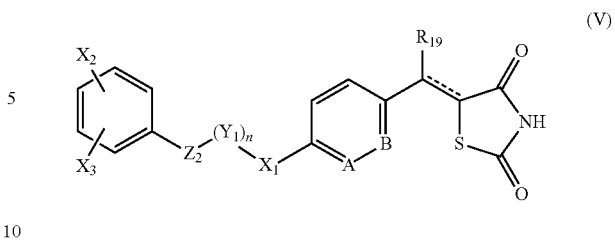
(V)

wherein the dotted line represents a bond or no bond; A and B are each independently CH or N. with the proviso that when A or B is N. the other is CH; X is S, SO, $SO_2$, $CH_2$, CHOH, or CO; n is 0 or 1; $Y_1$ is CHR$_{20}$ or R$_{21}$, with the proviso that when n is 1 and $Y_1$ is NR$_{21}$, $X_1$ is $SO_2$ or CO; $Z_2$ is CHR$_{22}$, $CH_2CH_2$, cyclic $C_2H_2O$, CH=CH, $OCH_2$, $SCH_2$, $SOCH_2$, or $SO_2CH_2$; $R_{19}$, $R_{20}$, $R_{21}$, and $R_{22}$ are each independently hydrogen or methyl; and $X_2$ and $X_3$ are each independently hydrogen, methyl, trifluoromethyl, phenyl, benzyl, hydroxy, methoxy, phenoxy, benzyloxy, bromo, chloro, or fluoro; a pharmaceutically acceptable cationic salt thereof; or a pharmaceutically acceptable acid addition salt thereof when A or B is N.

In some embodiments of the present invention, the PPARγ agonists can comprise compounds of Formula VI:

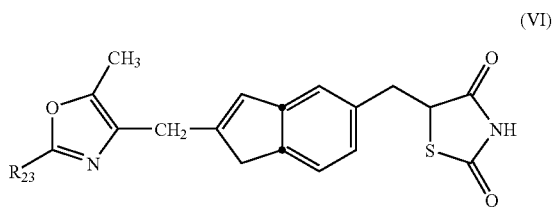
(VI)

or a pharmaceutically acceptable salt thereof, wherein $R_{23}$ is alkyl of 1 to 6 carbon atoms, cycloalkyl of 3 to 7 carbon atoms, phenyl or mono- or all-substituted phenyl wherein said substituents are independently alkyl of 1 to 6 carbon atoms, alkoxy of 1 to 3 carbon atoms, halogen, or trifluoromethyl.

In some embodiments of the present invention, the PPARγ agonists can comprise compounds of Formula VII:

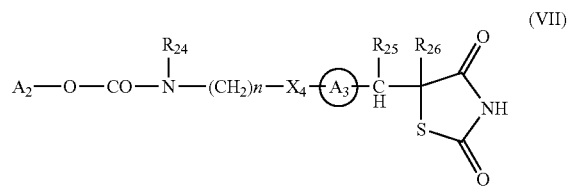
(VII)

or a tautomeric form thereof and/or a pharmaceutically acceptable salt thereof, and/or a pharmaceutically acceptable solvate thereof, wherein: $A_2$ represents an alkyl group, a substituted or unsubstituted aryl group, or an aralkyl group wherein the alkylene or the aryl moiety may be substituted or unsubstituted; $A^3$ represents a benzene ring having in total up to 3 optional substituents; $R_{24}$ represents a hydrogen atom, an alkyl group, an acyl group, an aralkyl group wherein the alkyl or the aryl moiety may be substituted or unsubstituted, or a substituted or unsubstituted aryl group; or $A_2$ together with $R_{24}$ represents substituted or unsubstituted $C_{2-3}$ polymethylene group, optional substituents for the polymethylene group being selected from alkyl or aryl or adjacent substituents together with the methylene carbon atoms to which they are attached form a substituted or unsubstituted phenylene group; $R_{25}$ and $R_{26}$ each represent hydrogen, or $R_{25}$ and $R_{26}$ together represent a bond; $X_4$ represents O or S; and n represents an integer in the range from 2 to 6.

In some embodiments of the present invention, the PPARγ agonists can comprise compounds of Formula VIII:

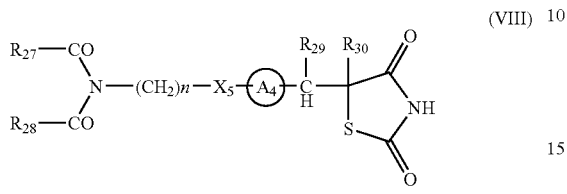

(VIII)

or a tautomeric form thereof and/or a pharmaceutically acceptable salt thereof, and/or a pharmaceutically acceptable solvate thereof, wherein: $R_{27}$ and $R_{28}$ each independently represent an alkyl group, a substituted or unsubstituted aryl group, or an aralkyl group being substituted or unsubstituted in the aryl or alkyl moiety; or $R_{27}$ together with $R_{28}$ represents a linking group, the linking group consisting or an optionally substituted methylene group or an O or S atom, optional substituents for the methylene groups including alkyl, aryl, or aralkyl, or substituents of adjacent methylene groups together with the carbon atoms to which they are attached form a substituted or unsubstituted phenylene group; $R_{29}$ and $R_{30}$ each represent hydrogen, or $R_{29}$ and $R_{30}$ together represent a bond; $A_4$ represents a benzene ring having in total up to 3 optional substituents; $X_5$ represents O or S; and n represents an integer in the range of 2 to 6.

In some embodiments of the present invention, the PPARγ agonists can comprise compounds of Formula IX:

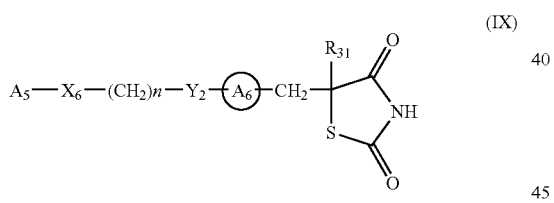

(IX)

or a tautomeric form thereof and/or a pharmaceutically acceptable salt thereof, and/or a pharmaceutically acceptable solvate thereof, wherein: $A_5$ represents a substituted or unsubstituted aromatic heterocyclyl group; $A_6$ represents a benzene ring having in total up to 5 substituents; $X_6$ represents O, S, or $NR_{32}$ wherein $R_{32}$ represents a hydrogen atom, an alkyl group, an acyl group, an aralkyl group, wherein the aryl moiety may be substituted or unsubstituted, or a substituted or unsubstituted aryl group; $Y_2$ represents O or S; $R_{31}$ represents an alkyl, aralkyl, or aryl group; and n represents an integer in the range from 2 to 6. Aromatic heterocyclyl groups include substituted or unsubstituted, single or fused ring aromatic heterocyclyl groups comprising up to 4 hetero atoms in each ring selected from oxygen, sulfur, or nitrogen. Aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2, or 3 heteroatoms, especially 1 or 2, selected from oxygen, sulfur, or nitrogen. Values for $A_5$ when it represents a 5-membered aromatic heterocyclyl group include thiazolyl and oxazoyl, especially oxazoyl. Values for $A_6$ when it represents a 6-membered aromatic heterocyclyl group include pyridyl or pyrimidinyl. $R_{31}$ represents an alkyl group, in particular a $C_{1-6}$ alkyl group (e.g., a methyl group).

A5 can represent a moiety of formula (a), (b), or (c), under Formula IX:

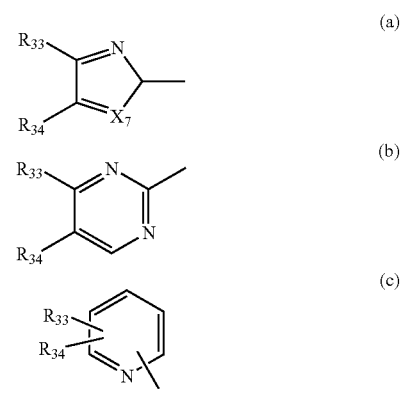

wherein, $R_{33}$ and $R_{34}$ each independently represents a hydrogen atom, an alkyl group, or a substituted or unsubstituted aryl group or when $R_{33}$ and $R_{34}$ are each attached to adjacent carbon atoms, then $R_{33}$ and $R_{34}$ together with the carbon atoms to which they are attached forth a benzene ring wherein each carbon atom represented by $R_{33}$ and $R_{34}$ together may be substituted or unsubstituted; and in the moiety of Formula (a), $X_7$ represents oxygen or sulfur.

In one embodiment of the present invention, $R_{33}$ and $R_{34}$ together present a moiety of Formula (d), under Formula IX:

(d)

wherein $R_{35}$ and $R_{36}$ each independently represent hydrogen, halogen, substituted or unsubstituted alkyl, or alkoxy.

In some embodiments of the present invention, the PPARγ agonists can comprise compounds of Formula X:

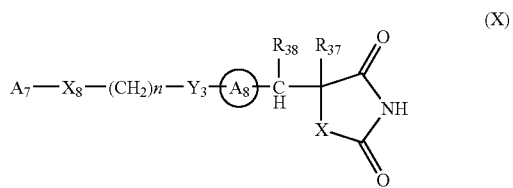

(X)

or a tautomeric form thereof and/or a pharmaceutically acceptable salt thereof, and/or a pharmaceutically acceptable solvate thereof, wherein: $A_7$ represents a substituted or unsubstituted aryl group; $A_8$ represents a benzene ring having in total up to 5 substituents; $X_8$ represents O, S, or $NR_9$, wherein $R_{39}$ represents a hydrogen atom, an alkyl group, an acyl group, an aralkyl group, wherein the aryl moiety may be substituted or unsubstituted, or a substituted or unsubstituted aryl group; $Y_3$ represents O or S; $R_{37}$ represents hydrogen; $R_{38}$ represents hydrogen or an alkyl, aralkyl, or aryl group or $R_{37}$ together with $R_{38}$ represents a bond; and n represents an integer in the range from 2 to 6.

In some embodiments of the present invention, the PPARγ agonists can comprise compounds of Formula XI:

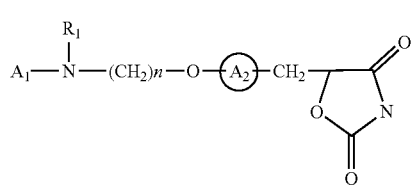
(XI)

or a tautomeric form thereof and/or a pharmaceutically acceptable salt thereof, and/or a pharmaceutically acceptable solvate thereof, wherein: $A_1$ represents a substituted or unsubstituted aromatic heterocyclyl group; $R_1$ represents a hydrogen atom, an alkyl group, an acyl group, an aralkyl group, wherein the aryl moiety may be substituted or unsubstituted, or a substituted or unsubstituted aryl group; $A_2$ represents a benzene ring having in total up to 5 substituents; and n represents an integer in the range of from to 6. Suitable aromatic heterocyclyl groups include substituted or unsubstituted, single or fused ring aromatic heterocyclyl groups comprising up to 4 hetero atoms in each ring selected from oxygen, sulfur, or nitrogen. Favored aromatic heterocyclyl groups include substituted or unsubstituted single ring aromatic heterocyclyl groups having 4 to 7 ring atoms, preferably 5 or 6 ring atoms. In particular, the aromatic heterocyclyl group comprises 1, 2, or 3 heteroatoms, especially 1 or 2, selected from oxygen, sulfur, or nitrogen. Values for $A_1$ when it represents a 5-membered aromatic heterocyclyl group can include thiazolyl and oxazolyl, especially oxazoyl. Values for $A_1$ when it represents a 6-membered aromatic heterocyclyl group can include pyridyl or pyrimidinyl.

In some embodiments of the present invention, the PPARγ agonists can comprise a compound of Formulas XII and XIII:

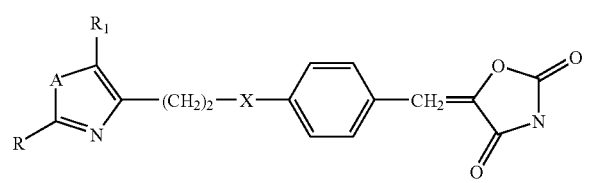
(XII)

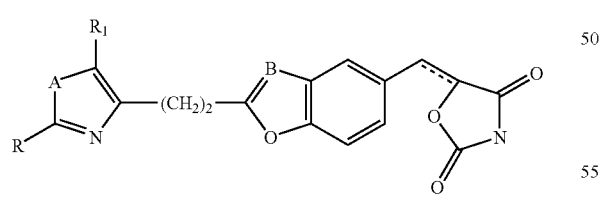
(XIII)

or pharmaceutically acceptable salts thereof wherein the dotted line represents a bond or no bond; R is cycloalkyl of three to seven carbon atoms, naphthyl, thienyl, furyl, phenyl, or substituted phenyl wherein the substituent is alkyl of one to three carbon atoms, alkoxy of one to three carbon atoms, trifluoromethyl, chloro, fluoro, or bis(trifluoromethyl); $R_1$ is an alkyl of one to three carbon atoms; X is O or C=O; A is O or S; and B is N or CH.

Some embodiments of the present invention include the use of the compounds of Formulas I through XIII are referred to as thiazolidine derivatives. Where appropriate, the specific names of thiazolidine derivatives may be used, including, for example, troglitazone, ciglitazone, pioglitazone, and rosiglitazone.

In certain embodiments, an activator of a PPARγ agonist may be used as described in U.S. Pat. No. 5,994,554, e.g., having a structure selected from the group consisting of formulas (XIV)-(XXVI):

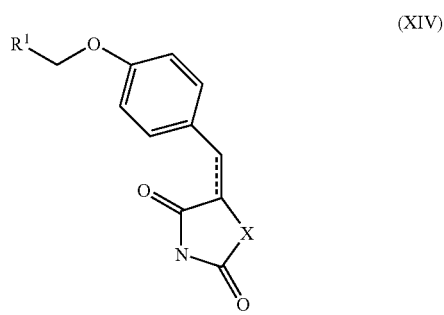
(XIV)

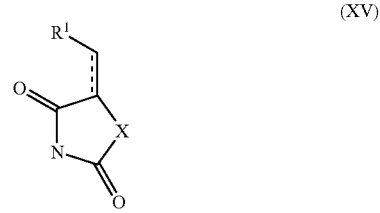
(XV)

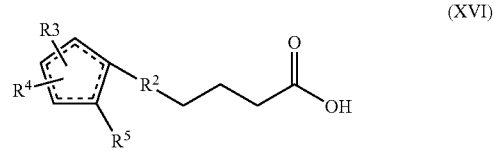
(XVI)

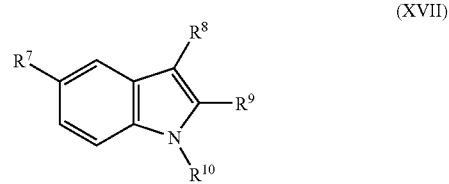
(XVII)

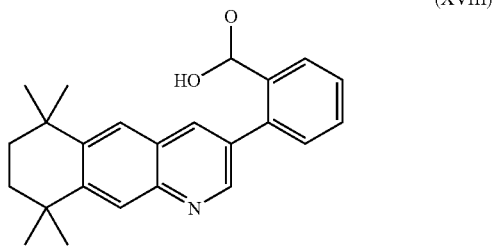
(XVIII)

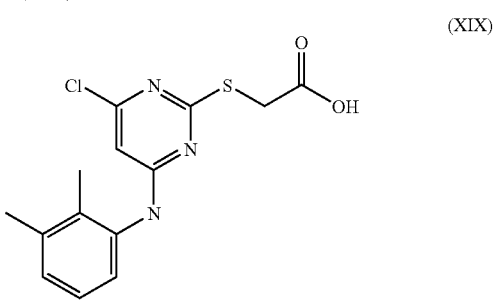
(XIX)

-continued

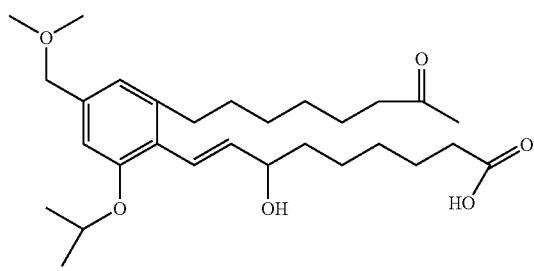
(XXII)

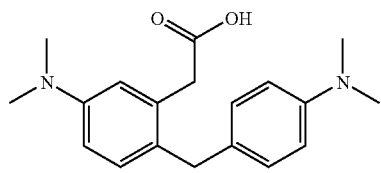
(XXIII)

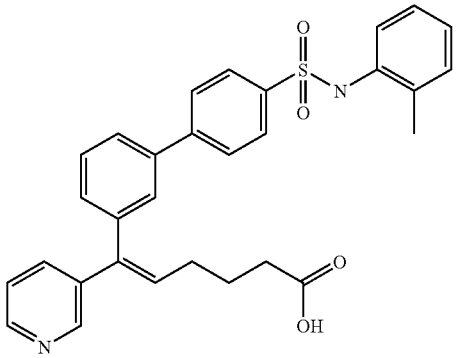
(XXIV)

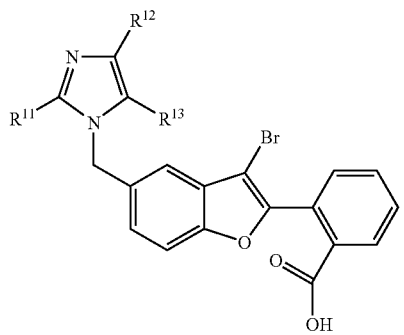
(XX)

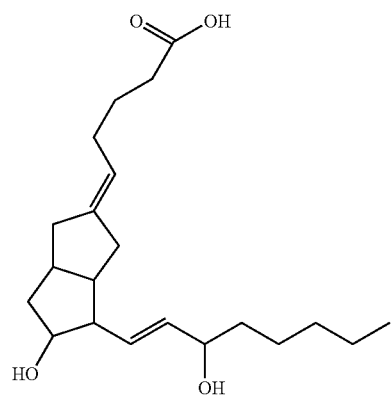
(XXI)

-continued

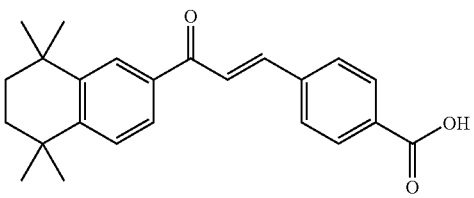
(XXV)

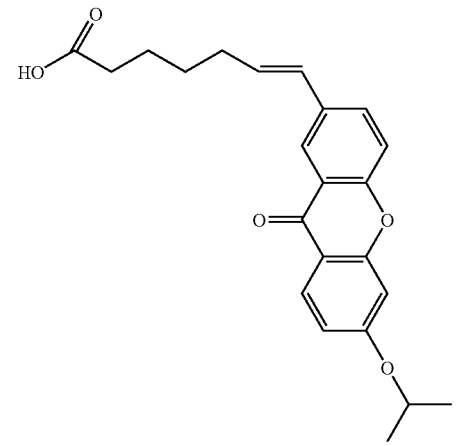
(XXVI)

wherein: $R^1$ is selected from the group consisting of hydrogen, $C_{1-8}$ alkyl, amino$C_{1-8}$ alkyl, $C_{1-8}$alkylamino $C_{1-8}$ alkyl, heteroarylamino $C_{1-6}$ alkyl, (heteroaryl)($C_{1-8}$alkyl)amino$C_{1-6}$ alkyl, ($C_{1-8}$ cycloalkyl) $C_{1-8}$ alkyl, $C_{1-8}$ alkylheteroaryl$C_{1-8}$ alkyl, 9- or 10-membered heterobicycle, which is partially aromatic or substituted 9- or 10-membered heterobicycle, which is partially aromatic; X is selected from the group consisting of S, NH, or O; $R^2$ is selected from the group consisting of hydrogen, $C_{1-8}$allyl or $C_{1-8}$alkenyl; $R^3$ and $R^4$ are independently selected from the group consisting of hydrogen, hydroxy, oxo $C_{1-8}$alkyl, $C_{1-8}$alkoxy or amino; $R^5$ is selected from the group consisting of hydrogen, $C_{1-8}$alkyl, $C_{1-8}$alkenyl, (carbonyl)alkenyl, (hydroxy)alkenyl, phenyl, $C_{1-8}$alkyl; $R^6$, (hydroxy) $C_{1-8}$alkyl; $R^6$, $C_{1-8}$alkyl $C_{1-8}$cycloallyl; $R^6$, (hydroxy) $C_1$-$C_{1-8}$cycloallyl; $R^6$ or $C_{1-8}$cycloallylthio$R^6$; $R_6$ is selected from the group consisting of phenyl or phenyl substituted with hydroxy, $C_{1-8}$alkyl or $C_{1-8}$alkoxy substituents; $R^7$ is selected from the group consisting of hydrogen, hydroxy, carboxy or carboxy $C_{1-8}$alkyl; $R^8$ is selected from the group consisting of hydrogen, $C_{1-8}$alkyl, phenyl, phenyl $C_{1-8}$alkyl, phenyl mono- or all-substituted with halo, hydroxy, and/or $C_{1-8}$alkoxy (e.g., methoxy) substituents or phenyl $C_{1-8}$alkyl wherein the phenyl is mono- or di-substituted with halo, hydroxy, and/or $C_{1-8}$alkoxy (e.g., methoxy) substituents; $R^9$ is selected from the group consisting of hydrogen, $C_{1-8}$alkyl, carboxy $C_{1-8}$alkenyl mono- or disubstituted with hydroxy, and/or $C_{1-8}$alkoxy (e.g., methoxy), phenyl or phenyl mono- or di-substituted with halo, hydroxy, and/or $C_{1-8}$alkoxy (e.g., methoxy); $R^{10}$ is hydrogen or $C_{1-8}$alkyl; $R^{11}$ is selected from the group consisting of hydrogen, $C_{1-8}$alkyl or cyclo$C_{1-8}$alkyl $C_{1-8}$alkyl; $R^{12}$ is selected from the group consisting of hydrogen, halo or fluorinated $C_{1-8}$alkyl; $R^{13}$ is selected from the group consisting of hydrogen, $C_{1-8}$alkoxycarbonyl or $C_{1-8}$alkoxycarbonyl $C_{1-8}$alkylaminocarbonyl; a dashed line (- - -) is none or one double bond between two of the carbon atoms; fluorinated alkyl can be an alkyl wherein one or more of the hydrogen atoms is replaced by a fluorine atom; heteroaryl can be 5-, 6- or 7-membered aromatic ring optionally interrupted by 1, 2, 3 or 4 N, S, or O heteroatoms, with the proviso that any two O or S atoms are not bonded to each other; substituted heteroaryl can be a 9- or 10-membered heterobicycle mono-, di-, or tri-substituted independently with hydroxy, oxo, $C_{1-6}$ alkyl, $C_{1-6}$ alkoxy or 9- or 10-membered heterobicycle, which is partially aromatic in more detail is a heterobicycle interrupted by 1, 2, 3, or 4 N heteroatoms; substituted 9- or 10-membered heterobicycle, which is partially aromatic in more detail is a 9- or 10-membered heterobicycle mono-, di-, tri- or tetra-substituted independently with hydroxy, oxo, $C_{1-8}$ alkyl, $C_{1-8}$ alkoxy, phenyl, phenyl $C_{1-8}$ alkyl; or a pharmaceutically acceptable acid-addition or base-addition salt thereof.

In yet other embodiments, the PPARγ agonists can comprise a compound as disclosed in U.S. Pat. No. 6,306,854, e.g., a compound having a structure of Formula (XXVII):

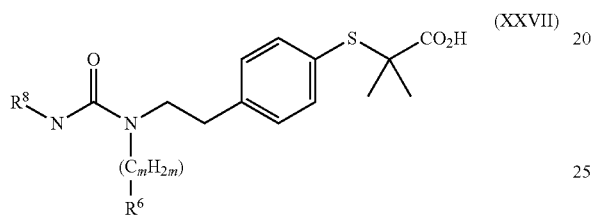

and esters, salts, and physiologically functional derivatives thereof; wherein m is from 0 to 20, $R^6$ is selected from the group consisting of hydrogen and

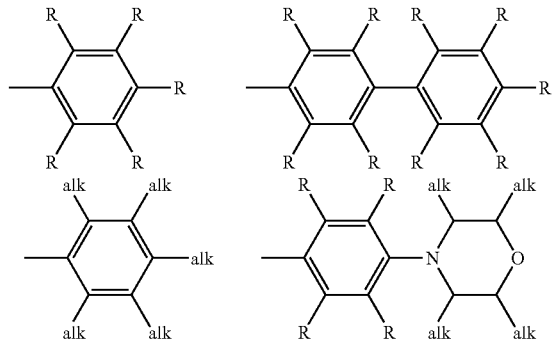

and $R^8$ is selected frown the group consisting of:

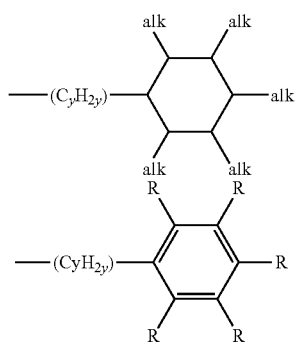

where y is 0, 1, or 2, each alk is independently hydrogen or alkyl group containing 1 to 6 carbon atoms, each R group is independently hydrogen, halogen, cyano, —$NO_2$, phenyl, straight or branched alkyl or fluoroalkyl containing 1 to 6 carbon atoms and which can contain hetero atoms such as nitrogen, oxygen, or sulfur and which can contain functional groups such as ketone or ester, cycloalkyl containing 3 to 7 carbon atoms, or two R groups bonded to adjacent carbon atoms can, together with the carbon atoms to which they are bonded, form an aliphatic or aromatic ring or multi ring system, and where each depicted ring has no more than 3 alk groups or R groups that are not hydrogen.

In yet other embodiments of the present invention, a PPARγ agonist can comprise a compound such as those disclosed in U.S. Pat. No. 6,294,580 and/or Liu et al., Biorg. Med. Chem. Lett. 11 (2001) 3111-3113, e.g., having a structure within Formula XXVIII:

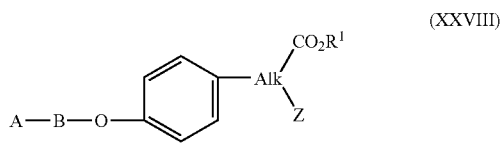

wherein A is selected from the group consisting of: (i) phenyl, wherein said phenyl is optionally substituted by one or more of the following groups; halogen atoms, $C_{1-6}$ alkyl, $C_{1-3}$ alkoxy, $C_{1-3}$ fluoroalkoxy, nitrite, or —$NR^7R^8$ where $R^7$ and $R^8$ are independently hydrogen or $C_{1-3}$ alkyl; (ii) a 5- or 6-membered heterocyclic group containing at least one heteroatom selected from oxygen, nitrogen and sulfur; and (iii) a fused bicyclic ring:

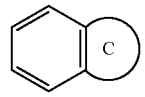

wherein ring C represents a heterocyclic group as defined in point (ii) above, which bicyclic ring is attached to group B via a ring atom of ring C; B is selected from the group consisting of: (iv) $C_{1-6}$ alkylene; (v)-M $C_{1-6}$ alkylene or $C_{1-6}$ alkyleneM $C_{1-6}$ alkylene, wherein M is O, S, or —$NR^2$ wherein $R^2$ represents hydrogen or $C_{1-3}$ alkyl; (vi) a 5- or 6-membered heterocyclic group containing at least one nitrogen heteroatom and optionally at least one further heteroaton selected from oxygen, nitrogen and sulfur and optionally substituted by $C_{1-3}$ alkyl; and (vii) Het-$C_{1-6}$ alkylene, wherein Het represents a heterocyclic group as defined in point (vi) above; Alk represents $C_{1-3}$ alkylene; Het represents hydrogen or $C_{1-3}$ alkyl; Z is selected from the group consisting of: (viii) nitrogen-containing heterocyclyl or heteroaryl, e.g., N-pyrrolyl, N-piperidinyl, N-piperazinyl, N-morpholinyl, or N-imidazolyl, optionally substituted with 1-4 $C_{1-6}$ alkyl or halogen substituents; (ix)-($C_{1-3}$ alkylene) phenyl, which phenyl is optionally substituted by one or more halogen atoms; and (x)—$NR^3R^4$, wherein $R^3$ represents hydrogen or $C_{1-3}$ alkyl, and $R^4$ represents $C_{1-6}$ alkyl, aryl or heteroaryl (e.g., phenyl, pyridinyl, pyrazinyl, pyrimidinyl, pyrrolyl, piperidinyl, piperazinyl, morpholinyl, imidazolyl), optionally substituted by 1-4 $C_{1-6}$ alkyl, halogen, $C_{1-6}$ alkoxyl, hydroxyl, nitro, cyano, or amino substituents, or —Y—(C═O)-T-$R^5$—Y—$SO_2$—$R^5$, or —Y— (CH(OH))-T-$R^5$, wherein: (a) Y represents a bond, $C_{1-6}$ alkylene, $C_{2-6}$ alkenylene, $C_{4-6}$ cycloalkylene or cycloalkenylene, a heterocyclic group as defined in point (vi) above, or phenyl optionally substituted by one or more $C_{1-3}$ alkyl groups and/or one or more halogen atoms; (b)

T represents a bond, $C_{1-3}$ alkyleneoxy, —O— or —N($R^6$)—, wherein $R^5$ represents hydrogen or $C_{1-3}$ alkyl; (c) $R^5$ represents $C_{1-6}$ alkyl, $C_{4-6}$ cycloalkyl or cycloalkenyl, phenyl (optionally substituted by one or more of the following groups; halogen atoms, $C_{1-3}$ alkyl, $C_{1-3}$ alkoxy groups, $C_{1-3}$ alkyleneNR$^9$R$^{10}$ (where each $R^9$ and $R^{10}$ is independently hydrogen, $C_{1-3}$ alkyl, —SO$_2$ $C_{1-3}$ alkyl, or —CO$_2$ $C_{1-3}$ alkyl, —SO$_2$ NH $C_{1-3}$ alkyl), $C_{1-3}$ alkyleneCO$_2$H, $C_{1-3}$alkyleneCO$_2$C$_{1-3}$ alkyl, or —OCH$_2$C(O)NH$_2$), a 5- or 6-membered heterocyclic group as defined in point (ii) above, a bicylic fused ring:

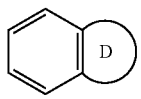

wherein ring D represents a 5- or 6-membered heterocyclic group containing at least one heteroatom selected from oxygen, nitrogen and sulfur and optionally substituted by (=O), which bicyclic ring is attached to T via a ring atom of ring D: or —C$_{1-6}$ alkyleneMR$^{11}$ M is O, S, or —NR$^{12}$ wherein $R^{11}$ and $R^{12}$ are independently hydrogen or $C_{1-3}$ alkyl, or a tautomeric form thereof, and/or a pharmaceutically acceptable salt or solvate thereof.

One specific group of compounds are those of Formula XI, wherein the dotted line represents no bond, $R^1$ is methyl, X is O and A is O. Examples of compounds in this group are those compounds where R is phenyl, 2-naphthyl and 3,5-bis(trifluoronethyl)phenyl. Another specific group of compounds are those of Formula XIII, wherein the dotted line represents no bond, $R^1$ is methyl and A is O. Particularly preferred compounds within this group are compounds where B is CH and R is phenol, p-tolyl, m-tolyl, cyclohexyl, and 2-naphthyl. In alternative embodiments of the present invention, the B is N and R is phenyl.

In still further embodiments, the present invention provides methods for the use of a pharmaceutical composition suitable for administering an effective amount of at least one composition comprising a PPARγ agonist or derivative thereof, such as those disclosed herein, in unit dosage form to treat a dermatological disorder. In alternative embodiments, the composition can further comprise a pharmaceutically acceptable carrier.

Specific examples of compounds of the present invention are given in the following list: (+)-5[[4-[(3,4-dihydro-6-hydroxy-2,5,7,8-tetramethyl-2H-1-benzopyran-2-yl)methoxy]phenyl]methyl]-2,4-thiazolidinedione; (troglitazone); 5-[4-[2-(5-ethylpyridin-2-yl)ethoxyl]benzyl]thiazolidine-2,4-dione; (pioglitazone); 5-[4-[(1-methylcyclohexyl)methoxy]benzyl]thiazolidine-2,4-dione; (ciglitazone); 4-(2-naphthylmethyl)-1,2,3,5-oxathiadiazole-2-oxide; 5-[4-[2-[(N-(benzoxazol-2-yl)-N-methylamino]ethoxy]benzyl]-5-methlthiazolidine-2,4-dione; 5-[4-[2-[2,4-dioxo-5-phenylthiazolidine-3-yl)ethoxy]benzyl]thiazolidine-2,4-dione; 5-[4-[2-[(N-methyl-N-(phenoxycarbonyl)amino]ethoxy]benzyl]thiazolidine-2,4-dione; 5-[4-[2-phenoxyethoxy)benzyl]thiazolidine-2,4-dione; 5-[4-[2-(4-chorophenyl)ethylsulfonyl]benzyl]thiazolidine-2,4-dione; 5-[4-[3-(5-methyl-2-phenyloxazol-4-yl)propionyl]benzyl]thiazolidine-2,4-dione; 5-[[4-(3-hydroxy-1-methylcyclohexyl)methoxy]benzyl]thiazolidine-2,4-dione; 5-[4-[2-(5-methyl-2-phenyloxazol-4-yl)ethoxyl]benzyl]thiazolidine-2,4-dione; 5-[(2-benzyl-2,3-dihydrobenzopyran)-5-ylmethyl]thiazolidine-2,4-dione; (englitazone); 5-[[2-(2-naphthylmethyl)benzoxazol]-5-ylmethyl]thiazolidine-2,4-dione; 5-[4-[2-(3-phenylureido)ethoxyl]benzyl]thiazolidine-2,4-dione; 5-[4-[2-(N-benzoxazol-2-yl)-N-metholamino]ethoxy]benzyl]thiazolidine-2,4-dione; 5-[4-[3-(5-methyl-2-phenyloxazol-4-yl)propionyl]benzyl]thiazolidine-2,4-dione; 5-[2-(5-methyl-2-phenyloxazol-4-ylmethyl)benzofuran-5-ylmethyl]oxazolidine-2,4-dione; 5-[4-[2-(N-methyl-N-(2-pyridyl)amino]ethoxy]benzyl]thiazolidine-2,4-dione (rosiglitazone); and 5-[4-[2-(N-(benzoxazol-2-yl)-N-methylamino]ethoxy]benzyl]oxazolidine-2,4-dione.

In yet other embodiments of the present invention, the PPARγ agonists can comprise compounds having the structure shown in Formula XXIX:

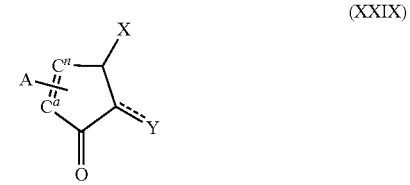

wherein: A is selected from hydrogen or a leaving group at the α- or β-position of the ring, or A is absent when there is a double bond between the Ca and Cn of the ring; X is an alkyl, substituted alkyl, alkenyl, substituted alkenyl, alkynyl, or substituted alkynyl group having in the range of 2 up to 15 carbon atoms; and Y is an alkyl, substituted alkyl, alkenyl, substituted alkenyl, alkynyl, or substituted alkynyl group having in the range of 2 up to 15 carbon atoms. As used herein, the term "leaving group" refers to functional groups which can readily be removed from the precursor compound, for example, by nucleophilic displacement, under E2 elimination conditions, and the like. Examples include, but are limited to, hydroxy groups, alkoxy groups, tosylates, brosylates, halogens, and the like.

The PPARγ agonists of the present invention (e.g., the compounds in Formulas I-XXIX and the others described above) are capable of further forming both pharmaceutically acceptable acid addition and/or base salts. All of these forms are within the scope of the present invention and can be topically administered to the subject to treat a dermatological disorder.

Pharmaceutically acceptable acid addition salts of the present invention can include, but are not limited to, salts derived from nontoxic inorganic acids such as hydrochloric, nitric, phosphohoric, sulfuric, hydrobromic, hydriodic, hydrofluoric, phosphorous, and the like, as well as the salts derived forth nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bissulfite, nitrate, phosphate, monoLydrogenphosphate, dihydrogenphosphate, metaphosphate, pyrophosphate, chloride, bromide, iodide, acetate, trifluoracetate, propionate, caprylate, isobutyrate, oxalate, malonate, succinate, suberate, sebacate, fumarate, malcate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like, as well as gluconate, galacturonate, and n-methyl glucamine.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner or as described above. The free base forms differ from their respective salt forms somewhat in certain physical properties such as solubility in polar solvents, but are otherwise equivalent to their respective free base for purposes of the present invention.

Pharmaceutically acceptable base addition salts are formed with metals or amides, such as alkali and alkaline earth metals or organic amines. Examples of metals used as cations include, but are not limited to, sodium, potassium, magnesium, calcium, and the like. Examples of suitable amines include, but are not limited to, $N_2$—N'-dibenzylethylenediamine, chloroprocaine, choline, diethanolamine, dicyclohexylamine, ethylenediamine, N-methylglucamine, and procaine.

The base addition salts of the acidic compounds are prepared by contacting the free acid form with a sufficient amount of the desired base to produce the salt in the conventional manner. The free acid form may be regenerated by contacting the salt form with an acid and isolating the free acid in the conventional manner or as described above. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including, but not limited to, hydrated forms. In general, the solvated forms, including hydrated forms, are equivalent to unsolvated forms and are intended to be encompassed within the scope of the present invention. Certain of the compounds of the present invention possess one or more chiral centers and each center may exist in different configurations. The compounds can, therefore, form stereoisomers. Although these are all represented herein by a limited number of molecular formulas, the present invention includes the use of both the individual, isolated isomers and mixtures, including racemates, thereof. Where stereo-specific synthesis techniques are employed or optically active compounds are employed as starting materials in the preparation of the compounds, individual isomers may be prepared directly. However, if a mixture of isomers is prepared, the individual isomers may be obtained by conventional resolution techniques, or the mixture may be used as is, with resolution.

Furthermore, the thiazolidene or oxazolidene part of the compounds of Formulas I through XIII can exist in the form of tautomeric isomers, and are intended to be a part of the present invention.

For preparing pharmaceutical compositions from the compounds of the present invention, pharmaceutically acceptable carriers can be in any suitable form (e.g., solids, liquids, gels, etc.). A solid carrier can be one or more substances which may also act as diluents, flavoring agents, binders, preservatives, and/or an encapsulating material.

The PPARγ agonists or derivatives thereof can be formulated for systemic administration and/or topical administration. Advantageously, the PPARγ agonists can be administered by local administered by topical administration to the site of the dermatological disorder. Topical administration is desirable because a lower dosage can be administered to the subject being treated to provide a therapeutically effective benefit. Additionally, administration of a lower topical dosage can mitigate adverse side-effects that may be associated with systemic administration.

Topical formulations include those for delivery via the mouth (buccal) and through the skin such that at least one layer of skin (i.e., the epidermis, dermis, and/or subcutaneous layer) is contacted with a PPARγ agonist or derivative thereof. Topical delivery systems may be used to administer topical formulations of the present invention. Topical delivery systems can include, for example, transdermal patches containing a PPARγ agonist or derivative thereof to be administered. Delivery through the skin can further be achieved by iontophoresis or electrotransport, if desired.

Formulations for topical administration in the mouth can include any one or combination of: lozenges comprising a PPARγ agonist or derivative thereof in a flavored basis, usually sucrose and acacia or tragacanth; pastilles comprising a PPARγ agonist or derivative thereof in an inert basis such as gelatin and glycerin or sucrose and acacia; and mouthwashes comprising a PPARγ agonist or derivative thereof to be administered in a suitable liquid carrier.

Formulations for topical administration to the skin can include ointments, creams, gels, and pastes comprising PPARγ agonists or derivatives thereof to be administered in a pharmaceutically acceptable carrier. Topical formulations for administration to the skin can include creams, ointments, and gels, for example, and can be prepared using oleaginous or water-soluble ointment bases, as is well known to those in the art. For example, these formulations may include vegetable oils, animal fats, and more preferably semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin, and glyceryl monostearate. Various water-soluble ointment bases may also be used including, for example, glycol ethers and derivatives, polyethylene glycols, polyoxyl 40 stearate, and polysorbates.

The dose, amount, and/or quantity of PPARγ agonists or derivatives thereof administered to the subject can depend on the specific PPARγ agonist or derivative thereof selected. It will be appreciated that the dosage amounts used will depend on the potency of the specific PPARγ agonist or derivative thereof and the therapeutic regimen employed.

In another aspect of the present invention, a variety of dermatological disorders can be treated by topically administering at least one PPARγ agonist or derivative thereof to a subject. A dermatological disorder can include any disorder of skin, hair or glands. A dermatological disorder can be manifest in the form of visible lesions, pre-emergent lesions, pain, sensitivity to touch, irritation, inflammation, or the like. Dermatological disorders can also include disorders of the cutaneous and pilosebaceous unit or the process of keratogenesis. For example, a dermatological disorder can be a disorder of the epidermis, dermis, subcutaneous layer, or combination thereof within and surrounding a pilosebaceous unit. Examples of dermatological disorders can include, but are not limited to, acne, alopecia, psoriasis, seborrhea, ingrown hairs and pseudofolliculitis barbae, hyperpigmented skin, cutaneous infections, lichen planus, Graham Little Syndrome, periorificial dermatitis, rosacea, hidradenitis suppurativa, dissecting cellulitis, systemic lupus erythematosus, discoid lupus erythematosus, and the like.

In another aspect of the present invention, at least one primary CA can be treated by topically administering at least one PPARγ agonist or derivative thereof to a subject. In general, CAs can be classified as lymphocytic, neutrophilic, and combinations thereof (i.e., "mixed"). Examples of lymphocytic CAs include lichen planopilaris, frontal fibrosing alopecia, chronic cutaneous lupus, erythematosus, pseudopelade, central centrifugal alopecia, alopecia mucinosa, and keratosis follicularis spinulosadecalvans. Examples of neutrophilic CAs include folliculitis decalvans, tufted folliculitis, and dissecting cellulitis. Examples of mixed CAs include folliculitis keloidalis and erosive dermatosis.

In an example of the present invention, a PPARγ agonist comprising a thiazolidinedione, such as rosiglitazone and/or pioglitazone, can be topically administered to treat a subject having a primary CA, such as LPP. A topical formulation comprising rosiglitazone and/or pioglitazone may be prepared in a gel or liquid, for example, and then administered to at least one region of the subject affected by LPP. The topical formulation may be administered to a portion of the subject's scalp exhibiting shiny, flat-topped bumps having an angular shape and a reddish-purplish color, for example Administering the topical formulation to the affected region may inhibit or decrease peroxisome loss in at least one cell, such as in a sebaceous stem cell, by increasing expression of the PEX genes and/or genes associated with lipid β-oxidation and desaturation. This, in turn, may decrease or inhibit lipid accumulation in the pilosebaceous unit and thereby channel the lipid stores to increase β-oxidation and abrogate the deleterious effects of lipid overload, i.e., inflammation, loss of hair follicles, and fibrosis.

The following examples are for the purpose of illustration only and are not intended to limit the scope of the claims, which are appended hereto.

EXAMPLE 1

Background

Figure 1:
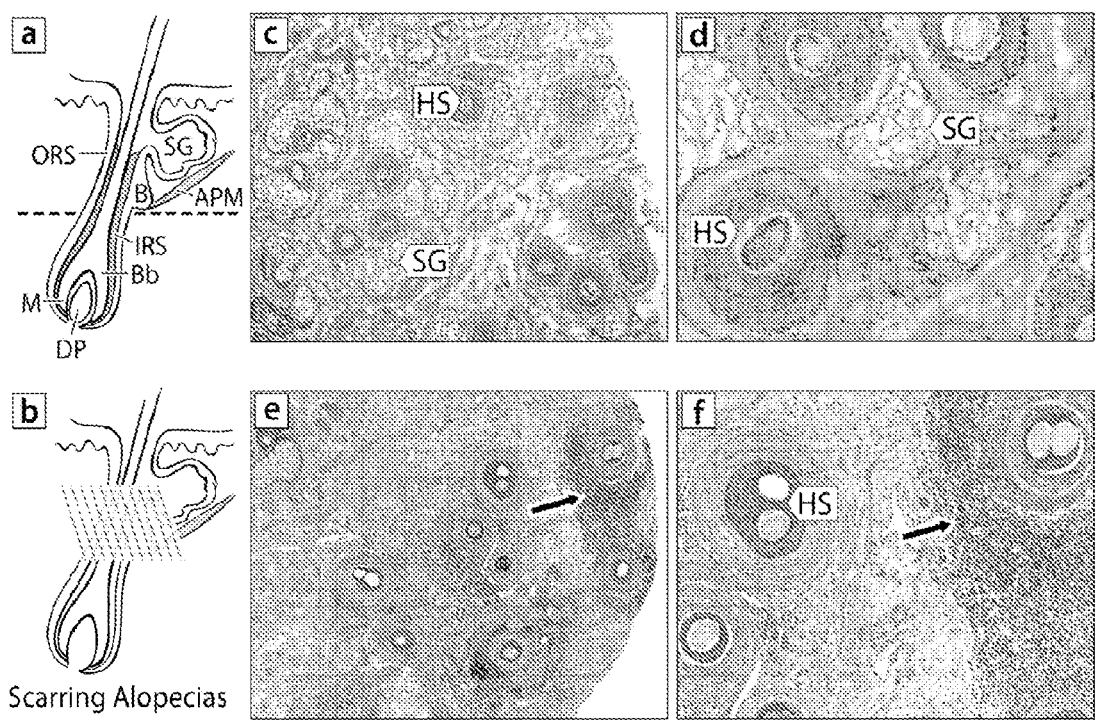
FIG. 1 illustrates histology of normal and LPP scalp tissue. a) Structure of the human hair follicle and the sebaceous glands (the pilosebaceous unit). The hair follicle stem cells are located in the hair follicle bulge region (B) between the arrector pili muscle (APM) and the sebaceous gland (SG). Other parts of the hair follicle depicted are the outer root sheath (ORS), inner root sheath (IRS), bulb (Bb), dermal papilla (DP) and matrix (M). b) In scarring alopecias, inflammation occurs in the permanent portion of the hair follicle where the bulge stem cells are located (striped area). Hematoxylin-eosin (H&E) staining of scalp biopsy sections of Normal at c) (10×) and d) (20×) show well formed pilosebaceous units. LPP tissue at e) (10×) and f) (20×) has very few hair follicles, loss of sebaceous glands and arrows indicate dense lymphocytic infiltrate around many hair follicles.

Cicatricial or scarring alopecia are a diverse group of hair disorders that cause permanent destruction of the pilosebaceous unit (PSU). Cicatricial alopecias that result from follicular loss due to thermal burns, metastatic cancer, trauma, and radiation are referred to as secondary (Stenn, K. S., Sundberg, J. P., and Sperling, L. C. 1999. Hair follicle biology, the sebaceous gland, and scarring alopecias. Arch Dermatol 135: 973-974; Price V H. 2006. The Medical Treatment of Cicatricial Alopecia. Seminars in Cutaneous Medicine and Surgery 25:56-59). Primary cicatricial alopecias (CA) are characterized by a folliculocentric inflammation with the ultimate replacement of the follicle with fibrous tissue and progressive and permanent hair loss (Arch Dermatol 135:973-974; Seminars in Cutaneous Medicine and Surgery 25: 56-59). The etiology and pathogenesis of CA remains unclear and they are currently treated as inflammatory disorders. Depending on the inflammatory cells detected during the active phase of the disease, CA are classified as lymphocytic (lichen planopilaris (LPP), frontal fibrosing alopecia, chronic cutaneous lupus erythematosus, pseudopelade (Brocq), central centrifugal alopecia, alopecia mucinosa, and keratosis follicularis spinulosadecalvans), neutrophilic (folliculitis decalvans, tufted folliculitis and dissecting cellulities) and mixed (folliculitis keloidalis and erosive pustular dermatosis) (Mirmirani, P., Willey, A., Headington, J. T., Stenn, K., McCalmont, T. H., and Price, V. H. 2005. Primary cicatricial alopecia: histopathologic findings do not distinguish clinical variants. J Am Acad Dermatol 52:637-643). The clinical features of all these disorders include destruction of hair follicles, progressive hair loss, and permanent replacement of the follicle with fibrous tissue. The destructive inflammatory changes are believed to occur in the follicular bulge region where the hair follicle stem cells are located (FIGS. 1a & 1b). If the stem cells are destroyed the affected follicles fail to re-grow and permanent hair loss ensues (Cotsarelis, G., and Millar, S. E. 2001. Towards a molecular understanding of hair loss and its treatment. Trends Mol Med 7:293-301).

The sebaceous glands (SG) are common victims along with the hair follicle in CA (Stenn, K. S., Sundberg, J. P., and Sperling, L. C. 1999. Hair follicle biology, the sebaceous gland, and scarring alopecias. Arch Dermatol 135:973-974). SG are appendages connected to the hair follicle to form the pilosebaceous unit (FIG. 1a). The function of SG in humans is obscure, although, it is known to secrete sebum composed of a unique mixture of lipid metabolic products (Downie, M. M., and Kealey, T. 1998. Lipogenesis in the human sebaceous gland: glycogen and glycerophosphate are substrates for the synthesis of sebum lipids. J Invest Dermatol 111:199-205). The SG are thought to facilitate the coordinated breakdown of the inner root sheath (IRS) during the hair cycle, and thus may be critical for follicular regeneration (Stenn, K. S. 2001. Insights from the asebia mouse: a molecular sebaceous gland defect leading to cicatricial alopecia. J Cutan Pathol 28:445-447). Spontaneous mouse mutants, Asebia (Josefowicz, W. J., Hardy, M. H. 1978. The expression of the gene asebia in the laboratory mouse. I. Epidermis and dermis. Genet Res. 31(1): 53-65) and Defolliculated (Porter, R. M., Jahoda, C. A. B., Lunny, D. P., Henderson, G., Ross, J., McLean, W. H. I., Whittock, N. V., Wilson, N. J., Reichelt, J., Magin T. M., and Lane, E. B. 2002. Defolliculated (Dfl): A Dominant Mouse Mutation Leading to Poor Sebaceous Gland Differentiation and Total Elimination of Pelage Follicles. Journal of Invest. Derm. 119, 32-37) harbor hypo-plastic sebaceous glands which may be the pathological cause of scarring alopecia in these models. Similar observations have been made with sebaceous adenitis with hyperkeratosis in dogs and cats (Stenn, K. S., Sundberg, J. P., and Sperling, L. C. 1999. Hair follicle biology, the sebaceous gland, and scarring alopecias. Arch Dermatol 135:973-974). In humans, the extent of sebaceous gland atrophy varies in different patients. Therefore, it is unclear as to whether CA results primarily from an abnormality or loss of sebaceous glands or from a deregulated inflammatory attack on follicular stem cells, although these two possibilities are not mutually exclusive. Thus, a molecular mechanism linking permanent loss of the hair follicle, sebaceous gland atrophy and inflammation is warranted to develop effective new therapy for CA.

Peroxisome Proliferator Activated Receptors (PPARγ, PPARα and PPARδ) are members of the nuclear receptor super-gene family that regulate the expression of genes involved in inflammation and lipid homeostasis (Wahli, W. 2002. Peroxisome Proliferator-Activated Receptors (PPARS): from metabolic control to epidermal wound healing. Swiss Med Wkly 132:83-91). They exhibit unique expression patterns within vertebrate tissues and are central regulators of gene expression and differentiation in several tissues including skin (Kuenzli, S. and J. H. Saurat 2003. Peroxisome proliferator-activated receptors in cutaneous biology. Br J. Dermatol. 149 (2): 229-36), sebaceous glands (Rosenfield, R. L., Kentsis A, Deplewski D, Ciletti N. 1999. Rat preputial sebocyte differentiation involves peroxisome proliferator-activated receptors. J Invest Dermatol, 112(2): 226-32), and the immune system (Cabrero, A., J. C. Laguna, and M. Vazquez 2002. Peroxisome Proliferator-Activated Receptors and the control of inflammation. Curr. Drug Targets Inflamm. Allergy, 1:243-8). Previous studies on PPAR protein expression suggest that the epidermis normally expresses predominantly PPARα, while sebocytes express more PPARγ than PPARα. These expression patterns may change during hyperplasia, differentiation and inflammation. While PPARγ plays a unique role in initiating the differentiation of sebocytes in the sebaceous gland, PPARδ is believed to induce sebocyte maturation (Rosenfield, R. L., Kentsis A, Deplewski D, Ciletti N. 1999. Rat preputial sebocyte differentiation involves peroxisome proliferator-activated receptors. J Invest Dermatol, 112(2): 226-32). PPARγ also interferes with many components of the inflammatory response by altering the expression of cytokines, receptors and adhesion molecules (Cabrero, A., J. C. Laguna, and M. Vazquez 2002. Peroxisome Proliferator-Activated Receptors and the control of inflammation. Curr. Drug Targets Inflamm. Allergy, 1:243-8). The broad spectrum regulatory potential of PPARγ in lipid metabolism and in controlling the inflammatory response suggests a crucial role for this nuclear receptor in the maintenance of the pilosebaceous unit.

Here, we report for the first time that PPARγ regulated pathways are deficient in the lymphocytic CA, Lichen planopilaris (LPP). PPARγ agonists can induce the expression of these down-regulated genes in human keratinocytes. Finally, targeted deletion of the PPARγ gene in the stem cells of the follicular bulge in mice causes scarring alopecia that resembles human disease. These findings reveal a novel role for PPARγ in maintenance of healthy pilosebaceous units and suggest that the loss of this function likely triggers the pathogenesis of LPP.

Results

Increased Expression of Apoptotic, Tissue Remodeling and Inflammatory Genes in LPP The lymphocytic CA, Lichen planopilaris (LPP), is the focus of our study here. In LPP, the scalp is often the only site of involvement with patchy or diffuse hair loss. In the active stage of disease, the histology is very characteristic with dense lymphocytic infiltrate around many follicular epithelia (FIGS. 1e & f). The end stage is characterized by perifollicular fibrosis, scarring and replacement of pre-existing follicles with fibrotic tracts. Patients selected for scalp biopsies had a clinical diagnosis of LPP with early active lesions that were judged clinically representative of primary CA. Hematoxylineosin (H&E) staining of affected tissue showed isthmic lymphocytic inflammation, atrophy of sebaceous glands and loss of hair follicles, consistent with LPP histopathology (FIGS. 1e & 1f). Normal controls examined had no evidence of hair or skin disorders, their scalp biopsies showed well-formed sebaceous glands and were devoid of inflammatory lesions (FIGS. 1c & 1d).

For microarray analysis, cRNA prepared from scalp biopsies of normal controls and from LPP patients (N=20), and from paired unaffected and affected scalp biopsies of LPP patients (N=10) was hybridized to Affymetrix HG-U133 Plus 2.0 chips. Of the ~47,000 genes and ESTs represented on these chips, 569 genes were differentially expressed (182 upregulated & 387 downregulated) in unaffected tissue and 425 genes were differentially expressed (205 upregulated & 219 genes downregulated with >2-fold changes) in affected LPP tissue compared to normal scalp. The microarray data was analyzed using Netaffx (Affymetrix) and Ingenuity Pathways Analysis (IPA) (Ingenuity Systems) for identifying gene annotations and affected biochemical pathways. The majority of up-regulated genes in affected LPP tissue were either required for tissue remodeling and apoptosis or were inflammatory genes as anticipated from histopathology.

Figure 2:
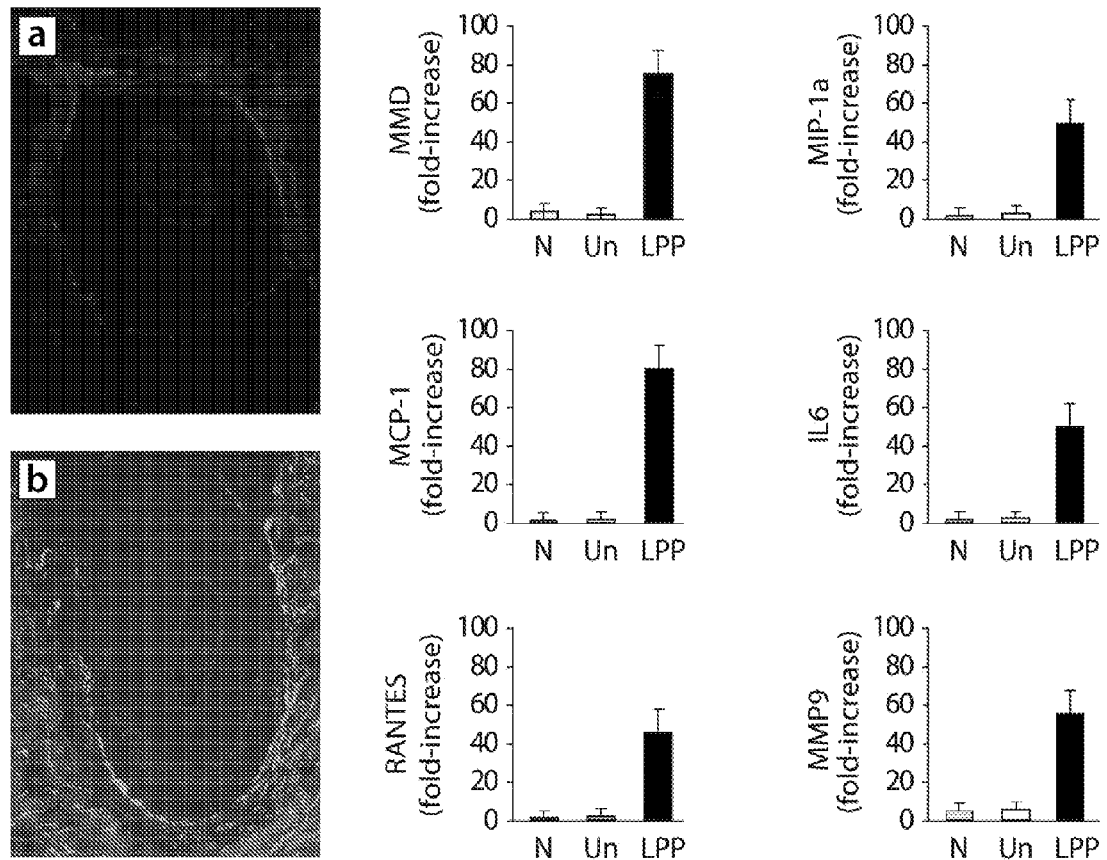
FIG. 2 illustrates inflammatory response in LPP. Immunofluorescence staining of horizontal sections of the isthmic region of the hair follicle in a) Normal and b) LPP scalp with CD68 antibodies. Positive CD68 staining in the isthmic region of the hair follicle in LPP suggests macrophage activation. Real-time PCR confirmed these observations and showed the upregulation of chemokines (MCP-1, MMD, MIP1a, RANTES), cytokines (IL6) and matrix metalloproteinases (MMP9) in affected but not in unaffected LPP tissue. The fold changes represent average values from 10 different patients (paired unaffected and affected tissue).

As shown in Table 1, we observed a dramatic increase in gene expression of cytokines/chemokines (MIP1, MCP1, CCL27, MMD, IL6, RANTES), extracellular matrix associated proteins (MMP1, MMP9, MMP10, MMP28, TIMP4, ADAMTS1), apoptosis-related genes (CASP1, GADD45B, PDCD6, PDCD4, CASP8) and cell surface antigens like CD 68 and CD 69 suggesting the activation and involvement of Macrophages and T lymphocytes in LPP. Osteopontin or Eta-1, for'early T lymphocyte activation 1', one of the key cytokines for type 1 immune responses mediated by macrophages and IL6 an immunoregulatory cytokine are both upregulated. SCYA27 is a cutaneous chemokine that has a pivotal role in T cell-mediated skin inflammation. The chemokine SCYA2 has a role in monocyte recruitment to sites of injury and infection. Two members of the chemokine beta family namely macrophage inflammatory protein 1 alpha (MIP-1 alpha) and RANTES (regulated on activation, normal T expressed and secreted) are also upregulated. Another gene that is upregulated is MMD (Monocyte-to-Macrophage Differentiation-associated protein), that converts circulating monocytes that emigrate into tissues either at random or in reaction to an inflammatory process, into the different types of mature macrophages. Indeed, immunofluorescence staining for the macrophage antigen CD68 demonstrated a marked increase in macrophage accumulation in the isthmic region of the hair follicles in LPP (FIG. 2b) compared to normal scalp biopsy sections (FIG. 2a). The microarray based gene expression changes in inflammatory genes described in Table 1 have been independently validated for the majority of the genes by real-time PCR analysis using RNAs used to generate microarray data as well as an independent set of paired patient samples. FIG. 2 shows a few representative examples.

TABLE 1

Upregulated transcripts in unaffected and affected LLP tissue

| GO Biological Process/Molecular Pathway | Upregulated transcripts in unaffected LLP | Up-regulated transcripts in affected LLP | Number of genes affected |
|---|---|---|---|
| 1 Immune Function | CD40 (TNFRSF5) (3.8), SPG21(10.9), ARTS-1 (4.15) | NR4A1 (22), MIP3A (SCYA20) (20), OPN (ETA1)(17), CD69 (14.5), RANTES* (SCYA5)(14), CD68 (6.9), IL6* (6), MIP2 (SCYB2)(5.7), MIP1a* (SCYA3)(5.3), MIP1b (SCYA4)(5.3), MSR1 (SCARA1) (5), CD14 (3.3), MCP2 (3), MCP1* (SCYA2)(2.8), MMD* (2.7), SCYA27 (CTACK)(2.7), HLA-C (9.2), HLA-A (5.3), B2M (5.3), HLA-G (3.3) HLA-DQB1 (18.4), HLA-DRB1 (4.6), CD74 (3.73) | 26 |

TABLE 1-continued

Upregulated transcripts in unaffected and affected LLP tissue

| GO Biological Process/Molecular Pathway | Upregulated transcripts in unaffected LLP | Up-regulated transcripts in affected LLP | Number of genes affected |
|---|---|---|---|
| 2 Tissue Remodeling | NONE | MMP3 (128), MMP1 (52), MMP1 (45), MMP9* (22), MMP12 (13), CYR61 (11), ADAMTS1 (5), PAI2 (3), TIMP4 (2.8), MMP28 (2) | 10 |
| 3 Apoptosis | NONE | CASP1 (17.2), GADD45B (10), PDCD6 (8.6), DUSP2 (7), DUSP6 (7), PDCD4 (5.7), CASP8 (2.5), CIDEA (2.64) | 8 |
| 4 Eicosanoid (Prostaglandins/Leukotrienes) signaling | | PTGER4 (55.72), PTGS2 (COX2)(6.52), PTGDS (4.3), Dicer 1 (3.8), ALOX5AP (2.9), PTGFR (2.14) | 6 |
| 5 Xenobiotic Metabolism | CYP1A1(9) | CYP1A1 (6.8), CYP2B7P1 (280) | 2 |

*indicates gene expression confirmed by real-time PCR fold changes for each gene are shown in brackets.

In addition to cytokines and chemokines, MHC Class I (2-microglobulin) & II genes are upregulated in affected LPP compared to unaffected and normal tissue (Table 1). Prior studies suggest that the human hair follicle appears to have "immune privilege" with major histocompatibility complex (MHC) class I negativity and an immunosuppressive cytokine milieu (Paus, R., Nickoloff, B J., Ito, T. 2005. A 'Hairy' Privilege. Trends Immunol. 26:32-40). The upregulation of MHC Class I & II genes raises the possibility that there is a collapse of "immune privilege" in the hair follicles of LPP patients. However, this complex issue is beyond the scope of this study and is currently being investigated in detail.

As shown in Table 1, several matrix metalloproteinases (MMP1, MMP9, MMP10, MMP28, ADAMTS1) are upregulated from ~5 to 100-fold in LPP. MMPs have been implicated in both physiological and pathological tissue remodeling, wound healing and inflammation. The angiogenic factor Cyr61 is more than 10 fold upregulated. This p53-regulated protein is capable of many functions including induction of MMP's and angiogenesis. We also identified eight apoptosis-related genes, including CASP1, CASP8, PDCD6 and PDCD4 that are upregulated ~2 to 18-fold. DUSP2 (Dual specificity phosphatase 2), a p53-target gene that is necessary and sufficient for p53-mediated apoptosis, is upregulated 6.9 fold. The other apoptosis-related genes that are upregulated in LPP are BCL2A1, GADD45B (Growth arrest and DNA-damage inducible gene), BTG2 (B-cell translocation gene 2) and KLF (kruppel-like factor 2). These data suggest that apoptosis and substantial matrix remodeling may characterize the programmed deletion of the hair follicle in LPP.

Intriguingly, another set of genes upregulated in LPP belong to the arachidonic acid/COX/prostaglandin pathway that is known to exert numerous immunoregulatory and proinflammatory activities. The prostaglandin EP4 receptor (PTGER4) is upregulated ~55 fold in LPP. PTGER4 receptors play an important role in antigen-specific immune responses in the skin by stimulating Langerhans cells mobilization, migration and maturation. Another gene that is upregulated more than 6 fold in LPP is prostaglandin synthase (PTGS2 or COX2). A major mechanism for the regulation of prostaglandin synthesis occurs at the level of cyclooxygenase. PTGS2 (COX2) is associated with biologic events such as injury, inflammation, and proliferation. Interestingly, we also observed a threefold increase in the expression of the lipid oxidation enzyme 5-lipoxygenase (5-LO) activating protein (ALOX5AP). The 5-LO pathway is the major source of potent proinflammatory leukotrienes (LTs) issued from the metabolism of arachidonic acid (AA). The 5-LO activating protein (ALOX5AP) binds arachidonic acid before transferring it to 5-LO which then catalyzes the initial enzymatic step in the formation of leukotrienes by the oxidation of arachidonic acid.

In stark contrast to the large number of inflammatory genes upregulated in affected LPP tissue, only three pro-inflammatory genes are upregulated in the paired unaffected tissue from LPP patients. These are CD40 (TNFRSF5), SPG21 and ARTS-1, genes required for activation of the pro-inflammatory cytokine Tumor Necrosis Factor-alpha (TNFα) (Table 1). CD40 is a cell surface receptor belonging to the TNF receptor family. It is an important co-stimulatory molecule in the development of cytotoxic T cell memory, T cell-dependent antibody responses and is also a potent survival signal for dendritic cells. The observation that the majority of inflammatory genes are upregulated in affected LPP but not unaffected tissue suggests that although the components of the immune signaling cascade, such as cytokines, chemokines and adhesion receptors, play an important role in disease progression, they may not represent primary events in the pathogenesis of LPP.

Decreased Expression of Lipid Metabolic and Peroxisomal Genes in LPP

Figure 13:
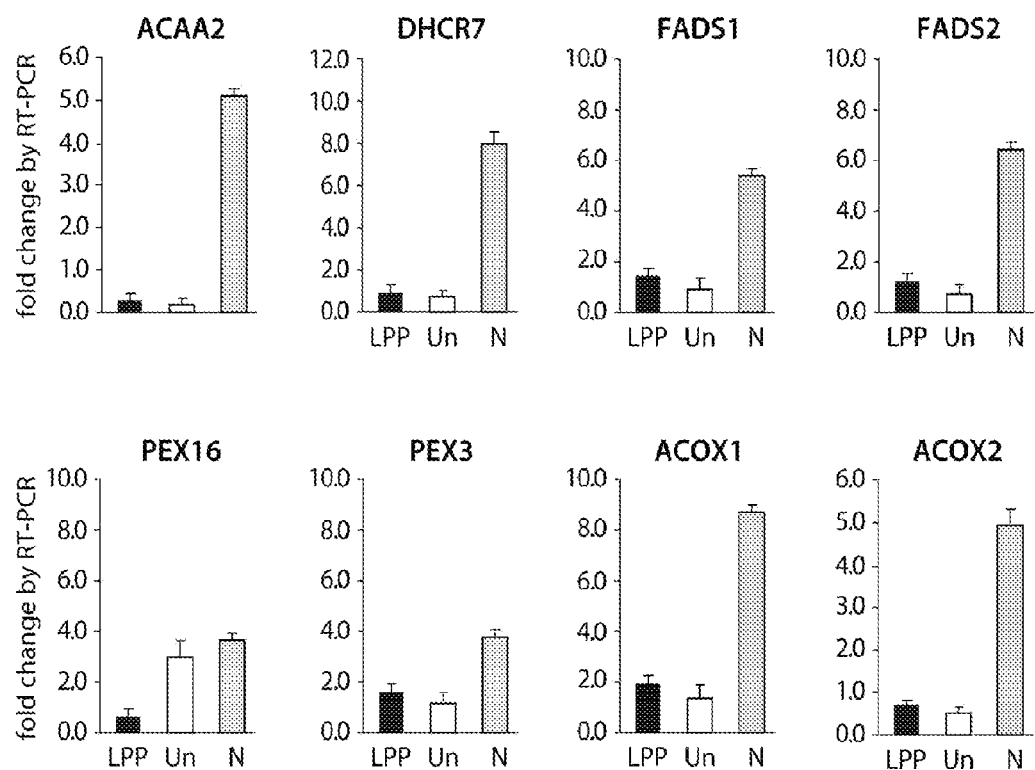
FIG. 13 illustrates lipid metabolic and peroxisomal genes are downregulated in LPP. Changes in gene expression of representative genes of fatty acid β-oxidation (ACAA2, ACOX1, ACOX2), fatty acid desaturation (FADS1-Delta 5-desaturase and FADS2-Delta 6-desaturase), peroxisome biogenesis (PEX3 and PEX16) and cholesterol/steroid biosynthesis (DHCR7) in unaffected tissue compared to paired affected tissue from LPP patients and normal controls. Real-time PCR analysis showed that the lipid metabolic are significantly decreased in unaffected tissue suggesting that these must represent early or primary events in disease pathogenesis and are not due to loss of sebaceous glands or scarring (histological changes that take place in affected LPP).

The majority of down-regulated genes in LPP were required for lipid metabolism and peroxisome biogenesis (Table 2). In addition, genes required for hair development and function were also downregulated in affected LPP tissue. Of the two hundred and nineteen genes that were downregulated in LPP, the largest group represented cellular lipid metabolic genes (42 genes) and included those involved in fatty acid β-oxidation and metabolism (22 genes), fatty acid desaturation, elongation and transport (10 genes) and cholesterol biosynthesis (10 genes) (Table 2). Surprisingly, data analysis of unaffected tissue revealed that the expression of the majority of lipid metabolic genes is already decreased significantly in unaffected tissue compared to normal or affected LPP tissue (Table 2). The microarray based gene expression changes were independently validated for representative genes by real-time PCR analysis in normal, unaffected and affected LPP tissue (FIG. 13). The effect of these transcriptional changes in lipid metabolic genes could result in deregulated lipid metabolism in the pilosebaceous gland of LPP patients. The decreased expression of lipid metabolic genes in unaffected tissue, including delta-6 desaturase (FADS2) (Table 2), a gene whose expression is restricted to differentiating sebocytes located in the suprabasal layers of the sebaceous gland (Ge L, Gordon J S, Hsuan C, Stenn K, Prouty S M. 2003. Identification of the delta-6 desaturase of human sebaceous glands: expression and enzyme activity. J Invest Dermatol. 120:707-14), suggests that these changes do not simply reflect the loss of the sebaceous glands but most likely represent early or primary events in the pathogenesis of LPP.

droplets, is upregulated by ~10-fold in affected tissue compared to ~2-3 fold in unaffected LPP. As shown in FIG. 3e, real-time PCR confirmed that perilipin gene expression is increased by over 5-fold in affected (N=10, pooled) compared to unaffected (N=10, pooled). These results validate our microarray data and immunohistochemical observations of lipid accumulation in LPP tissue.

We suspected that the effects of altered expression of lipid metabolism genes would be reflected in the lipid composition of scalp tissue (sebum) in LPP. We therefore analyzed the lipid profiles of paired unaffected and affected scalp biopsies

TABLE 2

Downregulated transcripts in unaffected and affected LLP tissue

| GO Biological Process/Molecular Pathway | Down-regulate transcripts in unaffected tissue of LLP patients | Down-regulated transcripts in affected tissue of LLP patients | Number of genes affected |
|---|---|---|---|
| 1 Fatty Acid metabolism | PPARγ (27), ACAA1 (8.7), ACAA2* (9.2), ACAD8 (8.7), ACADM(5.9), ACSBG1(7.6), ACSL1 (8.9), ACOT2 (17.5), ACOX2* (5.5), ACOX1* (22), ALOX15B (6.1), SOAT1 (7.5), AGPAT3 (10.4), ZAP128 (17.5), FABP7 (7), MLSTD1 (9) | PPARγ (19), ACAA2*(2.8), ACAD8 (2.46), ACADM(4), ACSBG1(2.5), ACSL1(2.8), ACOT2(4), ZAP128 (5), ACOX2*(6), ACOX1* (3), SLC27A2(4), AMACR(2.5), CRAT(2.8), ACAT2 (6.9), CYP4F8(6.9), GK(4), ACSL5(2.5), ALOX15B(6.9), HAO2(2), HSD11B1(3), PECR(6.9), SOAT1(2.8), AGPAT1(2.6), etc. | 60 |
| 2 Cholesterol Biosynthesis | HMGCR (34.5), HMGCS1 (8.4), SOAT (7.5,), FDPS (5.6), DHCR7* (5.8) | HMGCR (2.8), HMGCS1 (5), SOAT1 (2.8), MVD (3), PMVK (2.4), DHCR7* (5), MVK(3), FDPS (6), NSDHL(2.6), EBP(4), | 10 |
| 3 Fatty Acid desaturation, elongation and transport | FADS1* (8.9), FADS2* (21.5), FADS6 (14), ELOVL4 (27.8), INSIG1 (4.5,) | FADS1*(6.9), FADS2*(6), ELOVL4(4), INSIG1(2.8), ELOVL 5(8.5), ELOVL1(2.8), FACVL1(2), PCTP(2), LASS4(3), SCARB2(4) | 10 |
| 4 Perxisome biogenesis | PEX3* (3.5), PEX16* (2.8)) | PEX3*(10), PEX16*(6.9), PXMP2 (2.8), PEX 7 (5.8), PEX 11 (9) | 5 |
| 8 Hair follicle genes | NONE | KRT 15 (7.5), (KRT6B(4), KRT16(6.9), KRT84(8.5), KAP9-5(2.8), KAP9-9(2.6) etc. | 48 |

*indicates gene expression confirmed by real-time PCR fole changes for each gene are shown in brackets.

Abnormal Buildup of Lipids in LPP Biopsies

Figure 14:
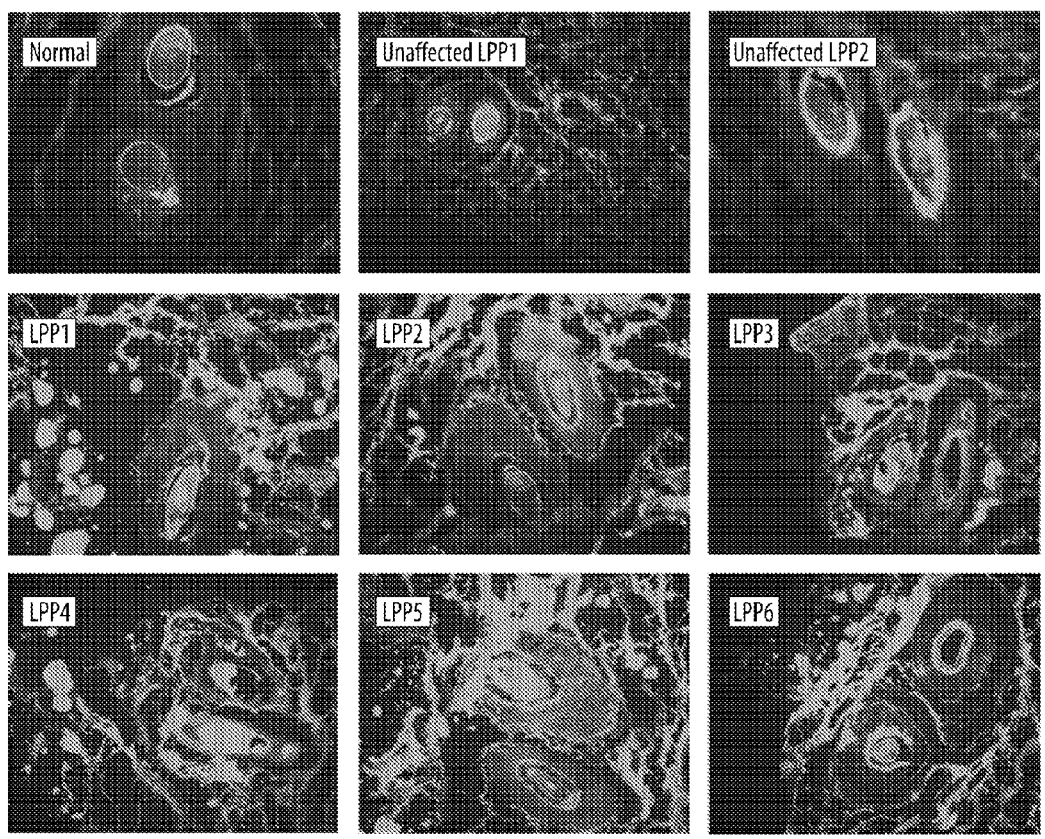
FIG. 14 illustrates Nile Red staining showed increased lipid accumulation in LPP suggesting deregulated lipid metabolism. LPP1-LPP6 show sections from six different patients with high lipid staining. Unaffected tissue (unaffected LPP1 and LPP2) shows dense lipid staining in the outer and inner root sheaths but not in the interstitial region. In normal tissue, lipid staining is restricted to the sebaceous glands.

To confirm that the down regulation of lipid metabolic genes has perturbed lipid homeostasis in the pilosebaceous units, we stained horizontal sections of scalp biopsies from normal and paired unaffected and affected LPP(N=10) with the lipid-staining dye Nile Red. We found abnormally high lipid staining of LPP tissue with the presence of large lipid droplets in the extracellular region of the perifolliculum in all samples tested (FIGS. 3c & 3d and FIG. 14). In contrast, in normal scalp biopsies (FIG. 3a) lipid staining was localized to the sebaceous glands and there were no lipid droplets in the perifollicular region. Unaffected tissue from LPP patients showed higher lipid staining in the outer and inner root sheaths of the hair follicle (ORS & IRS) than normal tissue with isolated lipid droplets in the perifolliculum (FIG. 3b). Our microarray data revealed that Perilipin A (Akimoto, N., Sato, T., Iwata, C., Koshizuka, M., Shibata, F., Nagai, A., Sumida, M., and Ito, A. Expression of perilipin A on the surface of lipid droplets increases along with the differentiation of hamster sebocytes in vivo and in vitro. J Invest Dermatol 124:1127-1133), a protein that coats the surface of lipid droplets (N=5) by gas chromatography. As shown in Table 3, lipid analysis demonstrated a 43% decrease in cholesterol esters and a 110% increase in triacylglycerols in affected scalp compared to unaffected scalp biopsies (Table 3) from the same patients. The fatty acid profile in all lipid fractions were also altered with a significant increase in arachidonic acid and a decrease in sapienic acid in affected LPP tissue (Table 3) in all lipid fractions tested (free fatty acids, triacylglycerols and phospholipids). Sapienic Acid is the major fatty acid in human sebum (J Invest Dermatol. 120:707-14) and is synthesized from linoleic acid by peroxisomal and mitochondrial β-oxidation followed by desaturation (Delta 6 and Delta 5-desaturase) pathways. The decrease in biosynthesis of Sapienic acid is probably caused by decreased expression of genes required for fatty acid β-oxidation and desaturation. These data validate microarray and real-time PCR observations (FIG. 13) and suggest that deregulated lipid metabolism in the pilosebaceous units of LPP patients, results in the increased production of bioactive arachidonic acid which is a precursor of pro-inflammatory lipids the leukotrienes and prostaglandins.

TABLE 3

Lipid Analysis* of unaffected and affected tissue from LPP patients

| Phospholipids | FA type | Unaffected | Affected | % change | Total Free Fatty Acid Profile | FA Type | Unaffected | Affected | % Change |
|---|---|---|---|---|---|---|---|---|---|
| 14:00 | | 1.18 | 0.85 | | 14:00 | | 3.68 | 2.9 | |
| 16:00 | Palmitic Acid | 23.24 | 23.01 | | 16:00 | Palmitic Acid | 26.67 | 25.65 | |
| 16:01 | Sapienic Acid | 4.55 | 3.3 | 27% | 16:01 | Sapienic Acid | 6.21 | 3.32 | 47% |
| 18:00 | Stearic Acid | 18.58 | 16.17 | 13% | 18:00 | Stearic Acid | 7.13 | 6.35 | |
| 18:01 | Elaidic Acid | 23.53 | 22.26 | 5% | 18:01 | Elaidic Acid | 38.73 | 43.6 | |
| 18.02 | Linoleic Acid | 17.71 | 18.22 | 2.80% | 18:02 | Linoleic Acid | 14.53 | 15.68 | 7.91% |
| 20:03 | | | | | 18:3w3 | | .71 | .08 | |
| 20:04 | Arachidonic Acid | 9.66 | 13.46 | 39% | 20:03 | | | | |
| 20:05 | | | | | 20:04 | Arachidonic Acid | 1 | 1.44 | 44% |
| 22:04 | | | | | 20:05 | | | | |
| 22:05 | Docosapentanoic acid | | 0.79 | | 22:04 | | 0.38 | 0.31 | |
| 22:06 | Docosahexanoic Acid | 1.93 | 1.56 | 24% | 22:05 | | 0.19 | 0.17 | |
| | | | | | 22:06 | | 0.33 | 0.22 | |
| Total μg | | 188.1 | 170.7 | | | | | | |
| Mg sample | | 58 | 78.6 | | | | | | |
| μg/mg Sample | | 3.2 | 2.2 | | | | | | |

| Triacyclglycerols | FA type | Unaffected | Affected | % change | Cholesterol esters | FA Type | Unaffected | Affected | % Change |
|---|---|---|---|---|---|---|---|---|---|
| 14:00 | | 4.46 | 3.3 | | 14:00 | | 3.12 | 3.99 | |
| 16:00 | Palmitic Acid | 30:88 | 29:55 | | 16:00 | Palmitic Acid | 21.37 | 20.36 | |
| 16:01 | Sapienic Acid | 3.014 | 3.53 | | 16:01 | Sapienic Acid | 44.25 | 31.64 | 28% |
| 18:00 | Stearic Acid | 7.32 | 6.82 | | 18:00 | Steric Acid | 4.37 | 5.08 | |
| 18:01 | Elaidic Acid | 39.62 | 40.82 | | 18:01 | Elaidic Acid | 11.07 | 20.29 | |
| 18.02 | Linoleic Acid | 14.2 | 15.38 | 8% | 18:02 | Linoleic Acid | 15.82 | 18.64 | 17.82% |
| 20:03 | | | | | 20:03 | | | | |
| 20:04 | Arachidonic Acid | 0.5 | 0.61 | 22% | 20:04 | | | | |
| 20:05 | | | | | 20:05 | | | | |
| 22:04 | | | | | 22:04 | | | | |
| 22:05 | | | | | 22:05 | | | | |
| 22:06 | | | | | 22:06 | | | | |
| Total μg | | 1461 | 4169.1 | | Total μg | | 81.8 | 59.2 | |
| mg Sample | | 58 | 78.6 | | Mg sample | | 58 | 78.6 | |
| μg/mg Sample | | 25.2 | 53.0 | 110% | μg/mg sample | 1.4 | 0.8 | 43% | |

Total lipids were extracted from paired unaffected and affected scalp tissue and lipid profiles determined by gas chromatography A representation example is shown Deficiency of Peroxisomes in LPP Peroxisomes are ubiquitous cell organelles that contain over 50 biochemical pathways known to play a role in oxygen, glucose, hydrogen peroxide and lipid metabolism (Wanders, R. J. 2004. Peroxisomes, lipid metabolism, and peroxisomal disorders. Mol Genet Metab 83:16-27). Genetic and proteomic studies in yeast and mammalian cell systems have led to the identification of up to 32 proteins (collectively called peroxins or PEX) involved in peroxisome biogenesis. In mammalian cells, three of these peroxins (PEX3, PEX16, and PEX19) are specifically involved in peroxisomal membrane protein (PMP) import (Schliebs, W., and W. H. Kunau 2004. Peroxisome membrane biogenesis: the stage is set. Curr. Biol. 14:R397-R399; Heiland, I., and R. Erdmann 2005. Biogenesis of peroxisomes. Topogenesis of the peroxisomal membrane and matrix proteins. FEBS J. 272:2362-2372). Previous studies have shown that when PEX3 or PEX16 proteins are absent or mutated in cells, peroxisomes disappear (Shimozawa, N., Suzuki, Y., Zhang, Z., Imamura, A., Ghaedi, K., Fujiki, Y., and Kondo, N. 2000. Identification of PEX3 as the gene mutated in a Zellweger syndrome patient lacking peroxisomal remnant structures. Hum Mol Genet. 9:1995-1999; Gould, S. J., and Valle, D. 2000. Peroxisome biogenesis disorders: genetics and cell biology. Trends Genet. 16:340-

Figure 4:
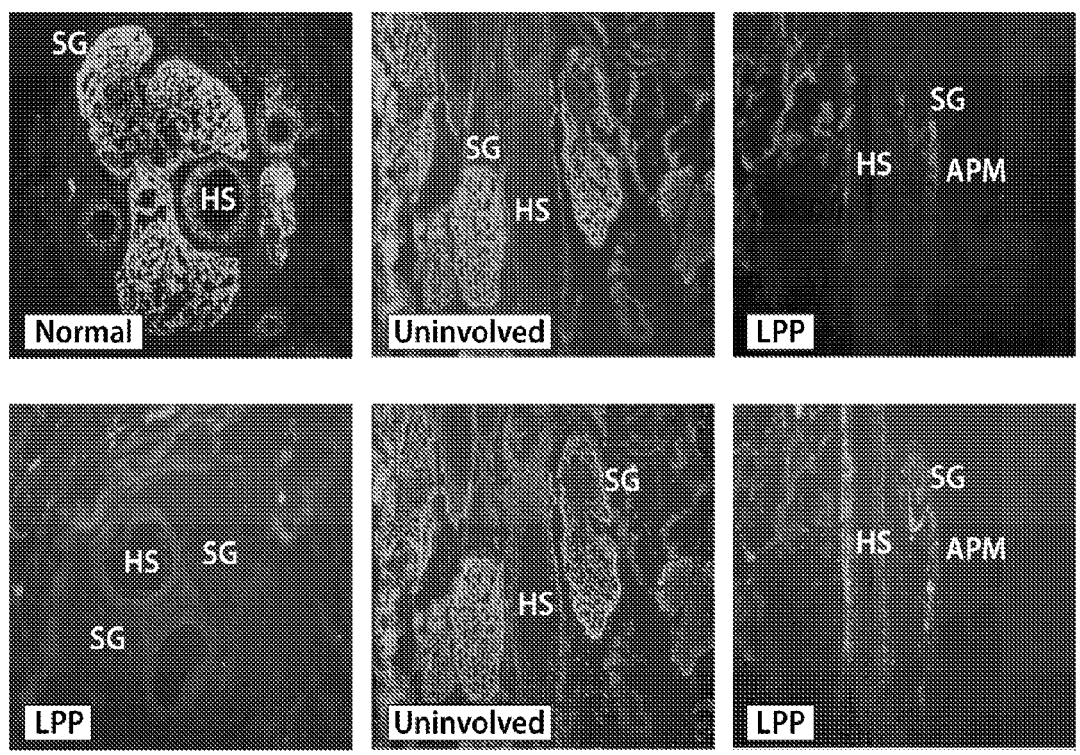
FIG. 4 illustrates peroxisome deficiency in LPP. Staining of peroxisomes with the anti-PMP70 primary antibody for the peroxisomal membrane protein and Alexa 488 labeled secondary antibodies. a) In normal scalp tissue, a characteristic "punctate" pattern of peroxisome staining is seen specifically in the sebaceous glands (SG) and in the ORS and IRS surrounding the hair shaft (HS). b) In unaffected tissue peroxisome staining is lost in the ORS and IRS cells surrounding the hair shaft but not in sebaceous glands e) Double staining the unaffected tissue sections for peroxisomes and nuclei (DAPI) shows that the ORS and IRS cells around the hair shaft are intact but they have lost peroxisomes. c) and d) LPP tissue shows a complete lack of staining for peroxisomes in the sebaceous glands and in the ORS and IRS cells surrounding the hair shaft. In LPP tissue, peroxisome staining is not seen in both the sebaceous gland and the hair shaft f) double staining for peroxisomes and nuclei reveals the presence of an intact sebaceous gland and hair follicle in LPP tissue suggesting the specific loss of peroxisomes.
Figure 15:
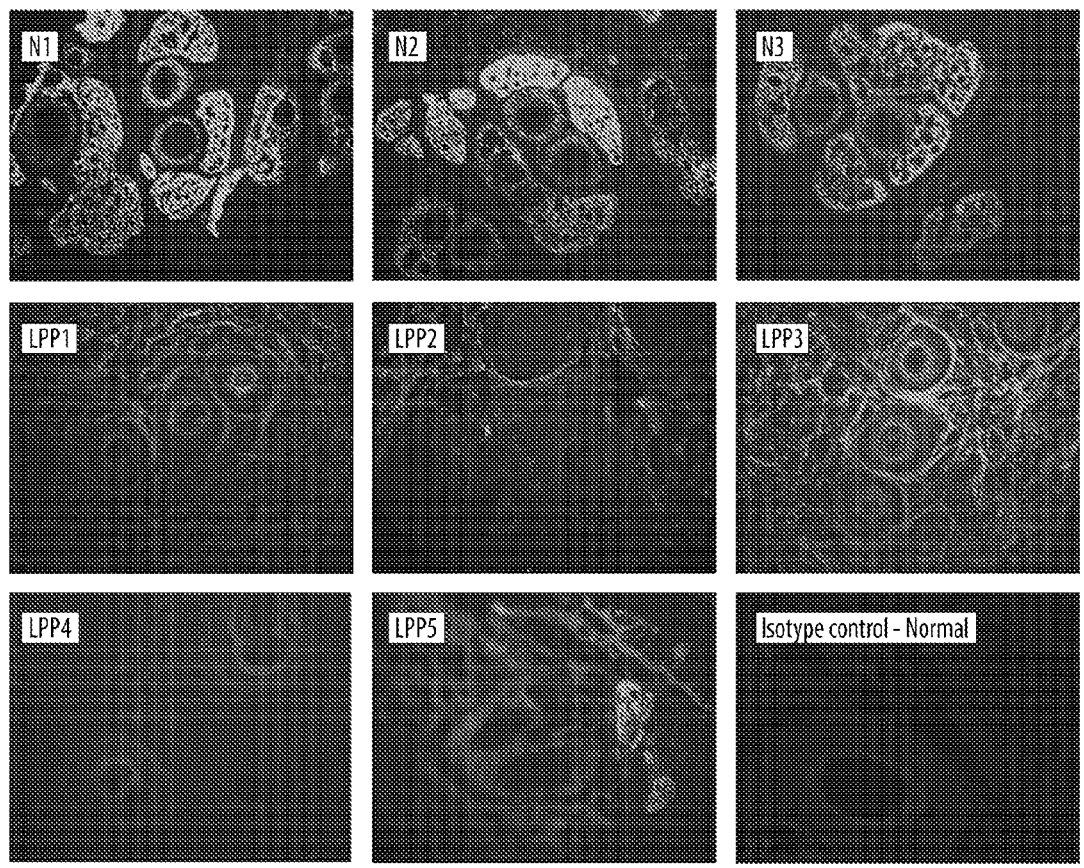
FIG. 15 illustrates the absence of peroxisome staining in LPP scalp sections. Staining of peroxisomes with the anti-PMP70 primary antibody for the peroxisomal membrane protein and Alexa 488 labeled secondary antibodies in normal scalp tissue, (N1, N2, N3) showed a characteristic "punctate" pattern of peroxisome staining in the sebaceous glands (SG)

345). Our microarray data (Table 2) showed that PEX3, PEX16 and PMP22 and other peroxin genes are downregulated in affected LPP. Again, as in the case of lipid metabolic genes, we show that PEX 3 gene is decreased significantly in unaffected LPP tissue as well, suggesting that peroxisomal changes are early events in LPP disease pathogenesis. Since many genes required for peroxisomal lipid metabolism are also downregulated in LPP, we speculated that these cell organelles may be defective in LPP. For visualization of peroxisomes, scalp biopsy sections from normal controls (N=10) and paired unaffected and affected LPP(N=10) were stained with the peroxisomal membrane protein PMP-70 and Alexa 488 labeled secondary antibodies (See also FIGS. 15 & 16). Normal scalp sections show PMP-70 positive "punctate" staining pattern characteristic of peroxisomes (Shimozawa, N., Suzuki, Y., Zhang, Z., Imamura, A., Ghaedi, K., Fujiki, Y., and Kondo, N. 2000. Identification of PEX3 as the gene mutated in a Zellweger syndrome patient lacking peroxisomal remnant structures. Hum Mol Genet. 9:1995-1999; Gould, S. J., and Valle, D. 2000. Peroxisome biogenesis disorders: genetics and cell biology. Trends Genet. 16:340-345). FIG. 4*a* shows abundant staining of peroxisomes specifically in normal sebaceous glands and in the inner (IRS) and outer (ORS) root sheaths of the hair follicles. In contrast, scalp sections from LPP patients lack PMP-70 positive peroxisome staining (FIGS. 4*b* & 4*e*). Double staining these tissue sections with the nuclear stain DAPI, verified the presence of sebaceous glands, IRS and ORS in LPP (FIG. 4*f*). Intriguingly, unaffected tissue from LPP patients already begins to show loss of peroxisomes in the IRS and ORS, although, sebaceous glands still show peroxisome staining (FIGS. 4*c* & 4*d*). This suggests that peroxisomes may be lost before sebaceous glands and demonstrates for the first time that LPP tissue displays peroxisomal deficiency.

Peroxisomal staining and confocal microscopy of the ORS and IRS of hair follicle at higher magnification (40×) shows numerous PMP-70 positive particles in normal tissue (FIG. 5*a*), but a complete absence of peroxisomal staining in LPP tissue. The PMP-70 immunoreactivity in normal tissue was significantly higher compared to LPP when the differences were quantified by Surface Plot Analysis (ImageJ NIH software) which provides a 3-D visualization of the intensity of PMP-70 staining particles. Thus, the lack of identifiable peroxisomal structures in LPP scalp tissue together with the downregulation of PEX3, PMP22 and PEX16 suggests that peroxisome deficiency may be due to an impairment of peroxisome biogenesis in LPP.

PPARγ Regulates Lipid Metabolic and Peroxisomal Gene Expression

Since a large number of inflammatory, lipid metabolic and peroxisomal genes are differentially expressed in LPP, we used the Ingenuity Pathways Analysis (IPA) Knowledge Base a comprehensive knowledge base of biological findings for genes of human, mouse, and rat, to determine functional associations between these genes and construct pathways and functional modules.

IPA analysis of microarray data from unaffected LPP tissue revealed that several of the downregulated genes (Table 2) including FADS1, ACOX1, ACAA1 and ACSL1 are directly regulated by PPARγ. We also observed a functional interaction between PPARγ and several of the upregulated genes in affected LPP including CD36, SLC27A1 and PTGS2 (COX2). Interestingly, these data also show that there is a functional negative regulatory loop between PPARγ and PTGS2 (COX2). As shown in Table 1, PTGS2 (COX2) gene expression is significantly increased (~6.5 fold) in affected tissue of LPP patients (N=20).

Figure 5:
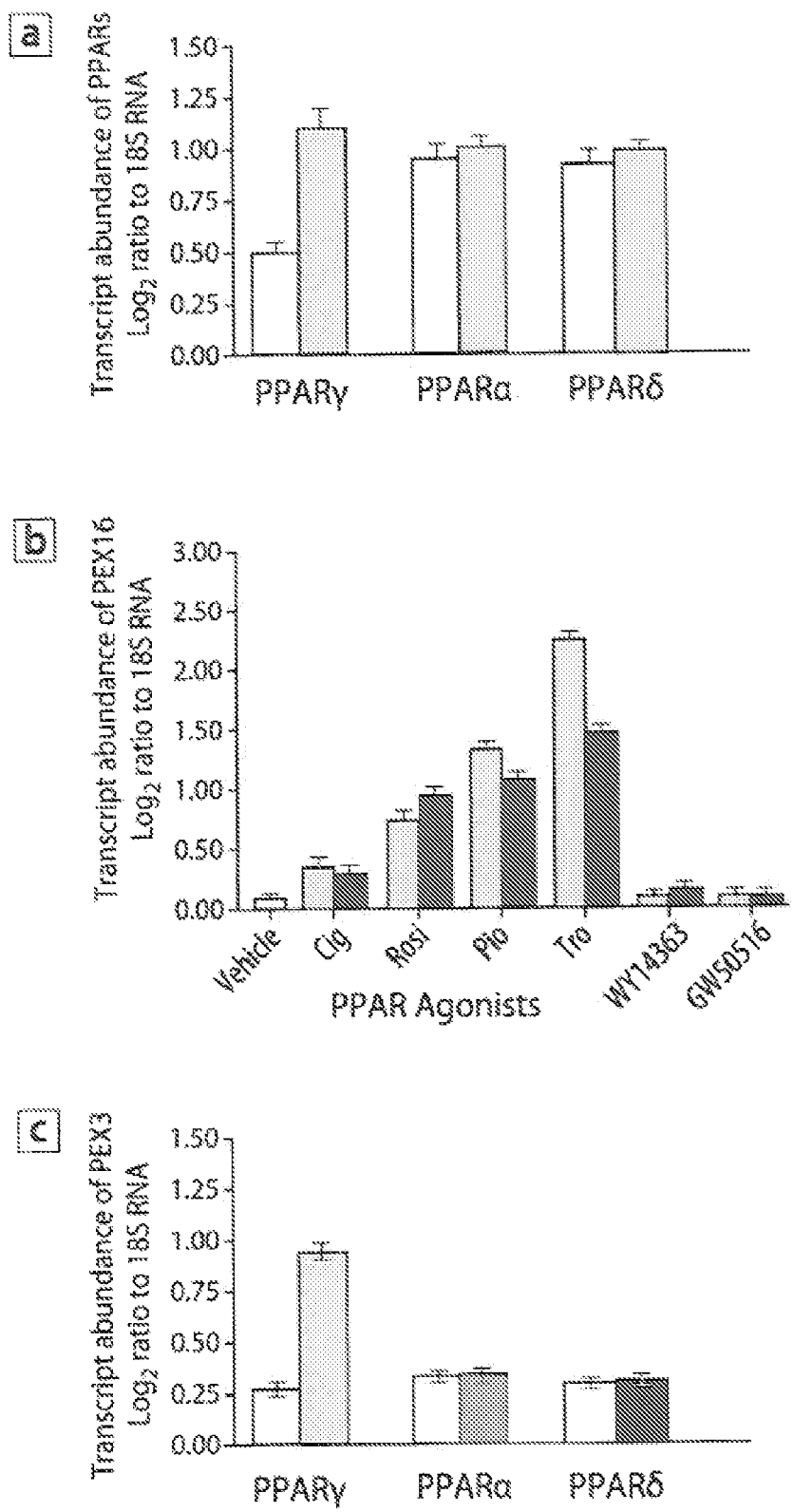
FIG. 5 illustrates altered PPARγ gene expression in LPP and its effect on PEX genes. a) Total RNA was isolated from control (N=20) and LPP scalp tissue (N=20) and PPARγ, PPARα and PPARδ gene expression was measured by real-time PCR. PPARγ expression was decreased by ~50% in LPP tissue. PPARγ gene expression was also decreased significantly in unaffected tissue (data not shown). However, the expression of PPARα and PPARδ remained unchanged in LPP compared to control samples. b) PPARγ modulation affects PEX 16 gene expression in vitro. HaCaT keratinocytes were treated with vehicle alone (0.1% DMSO) or with specific agonists (1 µM and 5 µM in 0.1% DMSO) of PPARγ-Ciglitazone (Cig), Rosiglitazone (Rosi), Pioglitazone (Pio) and Troglitazone (Tro), PPARα-WY-14363 and PPARδ-GW50516. After 48 hours, PEX16 gene expression was measured by real-time PCR. PPARγ agonists induced the expression of PEX16 gene; however, PPARα and PPARδ agonists had minimal effect. c) PPARγ modulation affects PEX 3 gene expression in outer root sheath (ORS) keratinocytes in vitro. In ORS cells, PPARγ agonist (Pioglitazone) induced PEX3 gene expression by ~4-fold compared to vehicle alone (0.1% DMSO). In contrast, PPARα-(WY-14363) and PPARδ (GW50516) agonists had minimal effect suggesting that PPARg regulates peroxisome biogenesis in the pilosebaceous units.

In-silico promoter analysis (5 kb upstream of the transcriptional start site) of differentially expressed genes in LPP with MAPPER (Multi-genome Analysis of Positions and Patterns of Elements of Regulation), a platform for computational identification of transcription factor binding sites (TFBSs) (Marinescu, V. D., Kohane, I. S., and Riva, A. 2005. MAPPER: a search engine for the computational identification of putative transcription factor binding sites in multiple genomes. BMC Bioinformatics 6:79) revealed peroxisome proliferator activated receptor gamma response elements (PPRE) on all downregulated genes (data not shown). This further suggested that the lipid metabolic and peroxisomal genes downregulated in LPP are regulated by PPARγ. We therefore analyzed the gene expression of the three PPAR isoforms in LPP and control tissue. Real-time PCR showed that there was a ~50% decrease in PPARγ (FIG. 5*a*). In contrast, the expression of PPARα and δ remained unchanged in LPP compared to normal controls (FIG. 5*a*). Thus, isoform-specific modulation of PPAR expression in LPP is suggestive of a functional role for this master regulator in LPP disease pathogenesis.

We directly assessed the role of PPARγ in modulating peroxisomal gene expression by growing HaCat cells (human keratinocyte cell line) in the presence of PPAR agonists (1 μM and 5 μM concentrations in 0.1% DMSO) and monitoring gene expression by real-time PCR (FIG. 5*b*). The agonists tested were Ciglitazone (Cig), Rosiglitazone (Rosi), Pioglitazone (Pio) and Troglitazone (Tro) specific for PPARγ, WY-14363 specific for PPARα and GW50516 specific for PPARδ. Remarkably, WY-14363 and GW50516 had minimal effect on PEX 16 gene expression at any concentration tested. In contrast, Ciglitazone, Rosiglitazone, Pioglitazone and Troglitazone induced an ~2-10 fold increase in PEX gene expression respectively (FIG. 5*b*). We also examined whether expression of the PEX3 gene is modulated by the PPAR agonist Pioglitazone (Pio) in cultured outer root sheath keratinocytes. Cells were grown in the presence or absence of Pio and PEX3 gene expression was monitored by real-time PCR. As observed with HaCaT cells (FIG. 5*b*), PPARα (WY-14363) and PPARδ (GW50516) had minimal effect on PEX3 gene expression in cultured outer root sheath keratinocytes (FIG. 5*c*). In contrast, Pio induced a 4-fold increase in PEX3 gene expression at a concentration of 1 μM (FIG. 5*c*). We have similarly observed that PPARγ agonists can induce the expression of lipid metabolic genes in human keratinocytes (data not shown). These results suggest that in human keratinocytes, it is the activation of PPARγ and not PPARα or PPARδ that induces PEX16 and PEX3 gene expression. Thus, deregulated lipid metabolism and the deficiency of peroxisomes in LPP may be directly related to the loss of PPARγ signaling.

Together, these results suggest that PPARγ is a master regulator that controls complex functional networks linking lipid metabolism and the immune response in the pilosebaceous units. It is likely that the loss of PPARγ gene expression in the pilosebaceous units, deregulates lipid metabolism and elevates the expression of proinflammatory pathways such as COX2 and 5-lipoxygenase (Table 1) thereby inducing an inflammatory response in LPP.

PPARg Gene Knockout Targeted to Stem Cells of the Follicular Bulge Causes Scarring Alopecia in Mice To uncover the function of PPARg in the pilosebaceous unit and its linkage to scarring alopecia-associated defects, we used Cre-loxP mediated gene targeting to delete PPARγ in stem cells of the hair follicle bulge using a stem cell specific promoter Keratin 15 (Liu Y, Lyle S, Yang Z, Cotsarelis G. 2003 Keratin 15 promoter targets putative epithelial stem cells in the hair follicle bulge. J Invest Dermatol. 121(5): 963-8; Cotsarelis, G., Sun, T. T., and Lavker, R. M. 1990. Label-retaining cells reside in the bulge area of pilosebaceous unit: implications for follicular stem cells, hair cycle, and skin carcinogenesis. Cell 61:1329-1337). Floxed PPARγ mice (PPARγ (f/f)) (He W; Barak Y; Hevener A; Olson P; Liao D; Le J; Nelson M; Ong E; Olefsky J M; 32 Evans R M. 2003. Adipose-specific peroxisome proliferator-activated receptor gamma knockout causes insulin resistance in fat and liver but not in muscle. Proc Natl Acad Sci USA 100(26):15712-7) contain loxP sites on either side of the exons 1 and 2 of the PPARγgene. Cre-mediated deletion of these exons is predicted to result in loss of PPARγ1 and a nonfunctional, N-terminal, 43-aa translational product of PPARγ2 that misses the partial AF1 domain and the first zinc finger of the DNA binding domain (Zhu, Y., Qi, C., Korenberg, J. R., Chen, X. N., Noya, D., Rao, M. S. & Reddy, J. K. 1995. Structural Organization of Mouse Peroxisome Proliferator-Activated Receptor (mPPAR) Gene: Alternative Promoter Use and Different Splicing Yield Two mPPAR Isoforms. Proc. Natl. Acad. Sci. USA 92, 7921-7925). The floxed PPARγ mice were crossed with a line of mice that express Cre under control of the keratin 15 promoter (K15-Cre) to yield the follicular stem cell specific PPARγ knockout mouse, PPARγ (f/f)/Cre. Homozygous PPARγ-stem cell KO mice (PPARγ (f/f)/Cre) were born at the expected Mendelian frequency, suggesting normal early development. Control mice were fl/fl littermates not expressing Cre.

Figure 6:
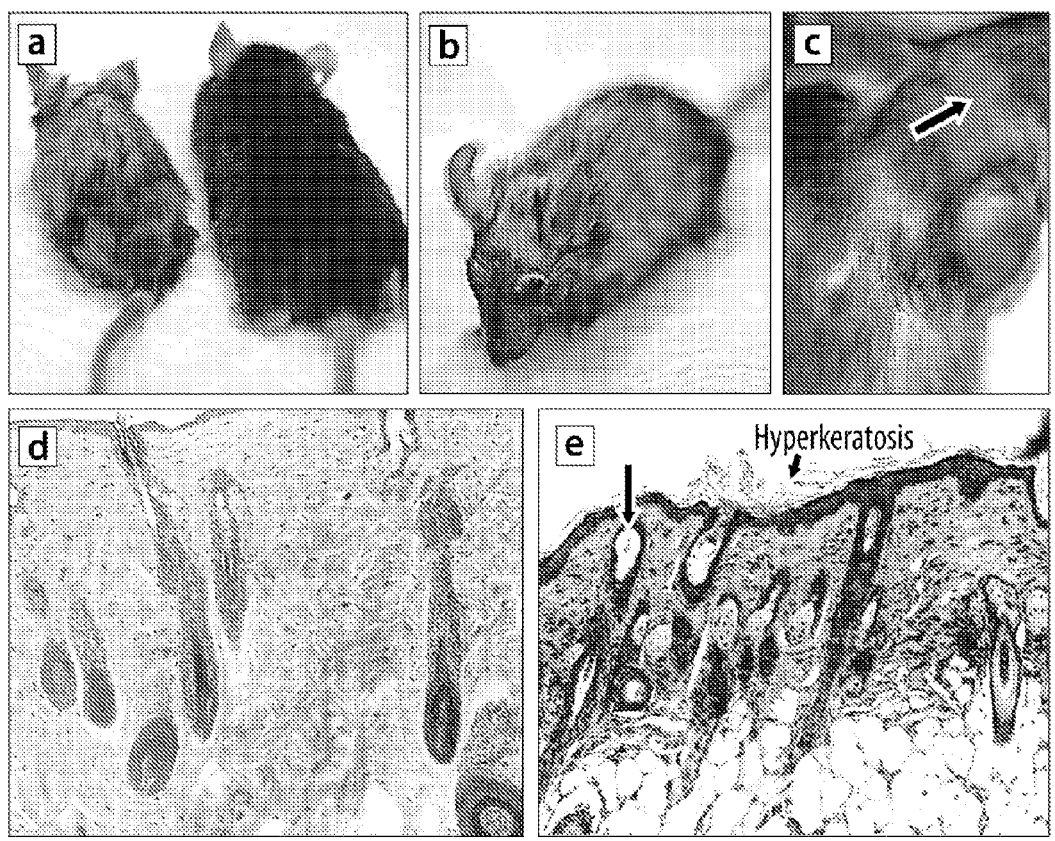
FIG. 6 illustrates targeted disruption of PPARγ in stem cells of the bulge resulted in scarring alopecia. a) and b) PPARγ$^{fl/fl}$/Cre mice (females, 3 months) with PPARγ$^{fl/fl}$ littermate (male). Hair loss occurs in a random patchy and progressive manner. The mice display severe pruritus and are smaller than their normal littermates. c) A close-up of the PPARγ$^{fl/fl}$/Cre mice shows a region with absence of follicular markings (indicated by arrow) and erythema suggesting the presence of inflammation. The PPARγ$^{fl/fl}$ littermates have normal skin and hair phenotype. Histology of skin of PPARγ$^{fl/fl}$ and PPARγ$^{fl/fl}$/Cre mice by Hematoxylin and eosin (H&E) staining of d) PPARγ$^{fl/fl}$ mice shows normal hair follicles and sebaceous glands. e) H&E staining of a PPARγ$^{fl/fl}$/Cre mouse shows hyperkeratosis and follicular plugging (indicated by arrow). The sebaceous glands appeared normal in the early stage disease (2-3 months).

As shown in FIG. 6a, floxed mice without Cre (PPARgfl/fl) (male) had normal skin and hair phenotypes. In contrast, PPARγ (f/f)/Cre mice (PPARγ stem cell KO mice) (FIGS. 6a and 6b) (female mice) displayed progressive hair loss and increasing pruritus. A close-up of the skin of PPARγ KO mouse (FIG. 6c) displays flakiness, mild erythema and a region with complete loss of follicular orifices. In advanced stage of disease, the skin of PPARγ KO mice appeared flaky and crusty and the remaining sparse hair was matted and often difficult to remove at the time of necropsy (data not shown). Affected animals were slightly smaller than their normal littermates.

Figure 7:
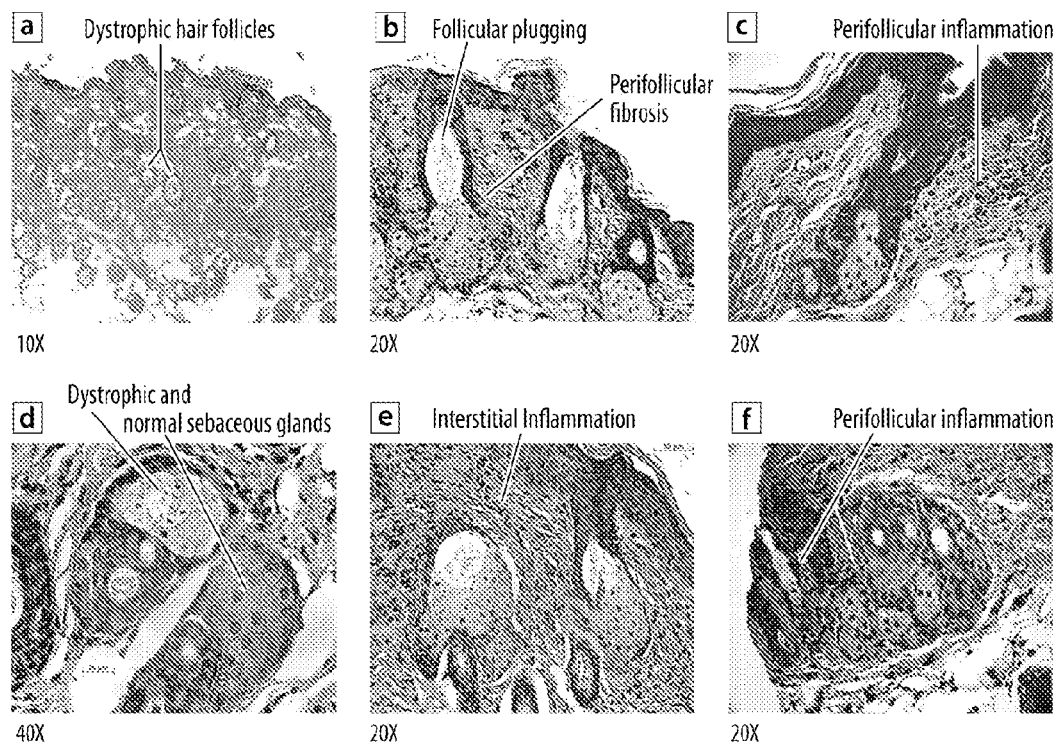
FIG. 7 illustrates PPARγ$^{fl/fl}$/Cre mice show histopathological features of scarring alopecia. H&E staining of the skin of PPARγ$^{fl/fl}$/Cre mice showed a) dystrophic hair follicles, b) follicular plugging, c), f) & e) perifollicular and interstitial inflammation and d) dystrophic sebaceous glands.
Figure 8:
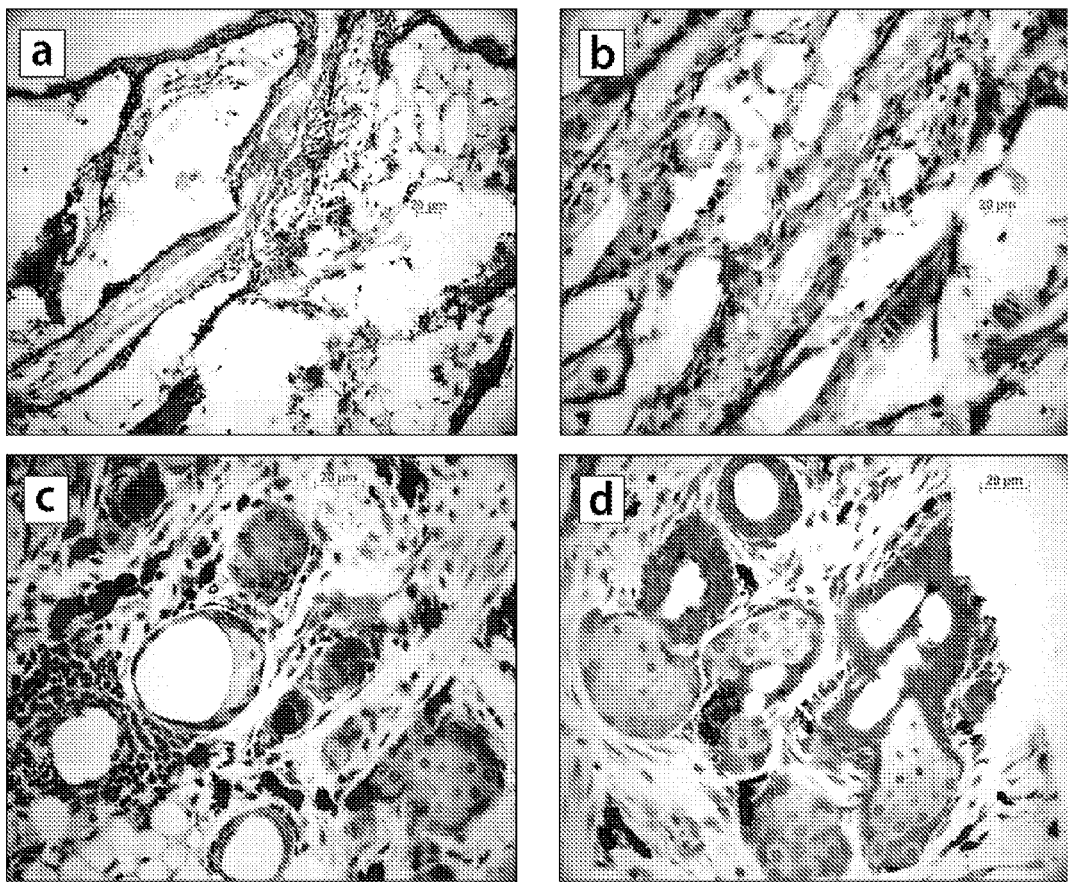
FIG. 8 illustrates PPARγ$^{fl/fl}$/cre mouse skin shows increased infiltration of macrophages and mast cells. Immunofluorescence staining of the skin PPARγ$^{fl/fl}$/cre mouse with F4/80 antibodies, a marker for macrophage activation showed increased a) F4/80 positive cells in the isthmic region of the hair follicle and in the b) perifollicular regions. c & d) Increased mast cells were detected in PPARγ$^{fl/fl}$/Cre mouse skin by Toluidine blue staining.
Figure 9:
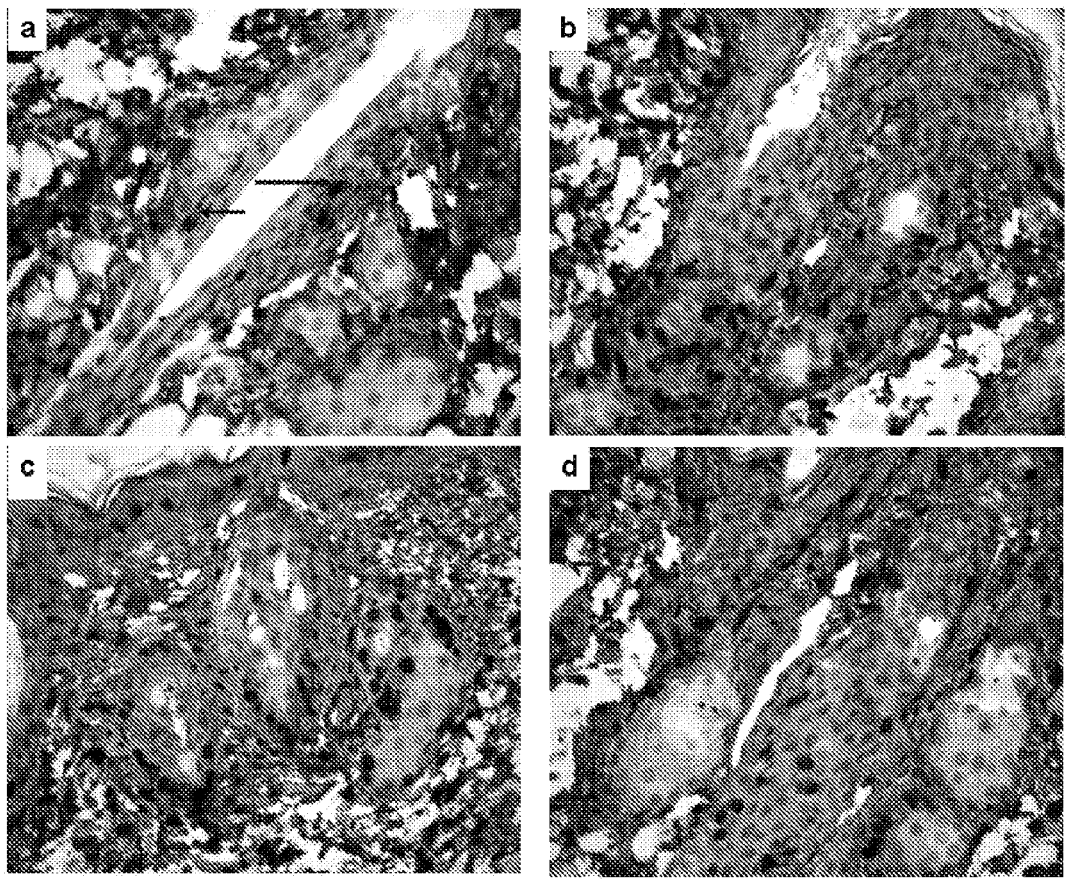
FIG. 9 illustrates infiltration of T lymphocytes in PPARγ$^{fl/fl}$/cre mouse skin. Immunofluorescence staining of the skin PPARγ$^{fl/fl}$/cre mouse with CD3 antibodies, shows the dense infiltration of T cells a) in the isthmic region of the hair follicle, b & d) in the perifollicular regions c) and surrounding the sebaceous glands.

Hematoxylin—eosin stained paraffin sections of the skin from control littermates showed normal skin and hair follicle histology (FIG. 6d). In contrast, the PPARγ KO mice (FIG. 6e), showed an obvious difference in the morphology of hair follicles. H&E stained sections of the skin of these mice showed hyperkeratosis and follicular ostia that appeared dilated and plugged. There was increased interstitial inflammation. As shown in FIG. 7, the PPARg KO mice display several histopathological features of scarring alopecia. Dystrophic hair follicles, follicular plugging and perifollicular fibrosis were observed. In some cases, the sebaceous glands appeared dystrophic and contiguous with the follicular plugs. The dermis had progressively increasing cellularity with interstitial inflammation. Perifollicular inflammation in the form of a mixed mononuclear infiltrate consisting of lymphocytes, plasma cells, macrophages and mast cells was also observed (FIG. 7). Immunofluorescent and histochemical staining confirmed the histopathology and showed that frozen and/or paraffin sections of skin from PPARγ KO and control mice were positive for macrophages (F4/80), mast cells (Toluidine blue) (FIG. 8) and T cells (CD3) (FIG. 9). The F4/80+ cells were detected around the isthmic region of the hair follicle (FIGS. 8a & b) in the affected skin of PPARγ KO mice. Mast cells were detected in the interstitial and perifollicular region (FIGS. 8c & d). CD3-positive T lymphocytes were detected in the isthmic region (FIG. 9) of the hair follicles. In more advanced disease, dense lymphocytic staining was seen in the perifollicular and interstitial regions of the dermis (FIG. 9c).

Figure 10:
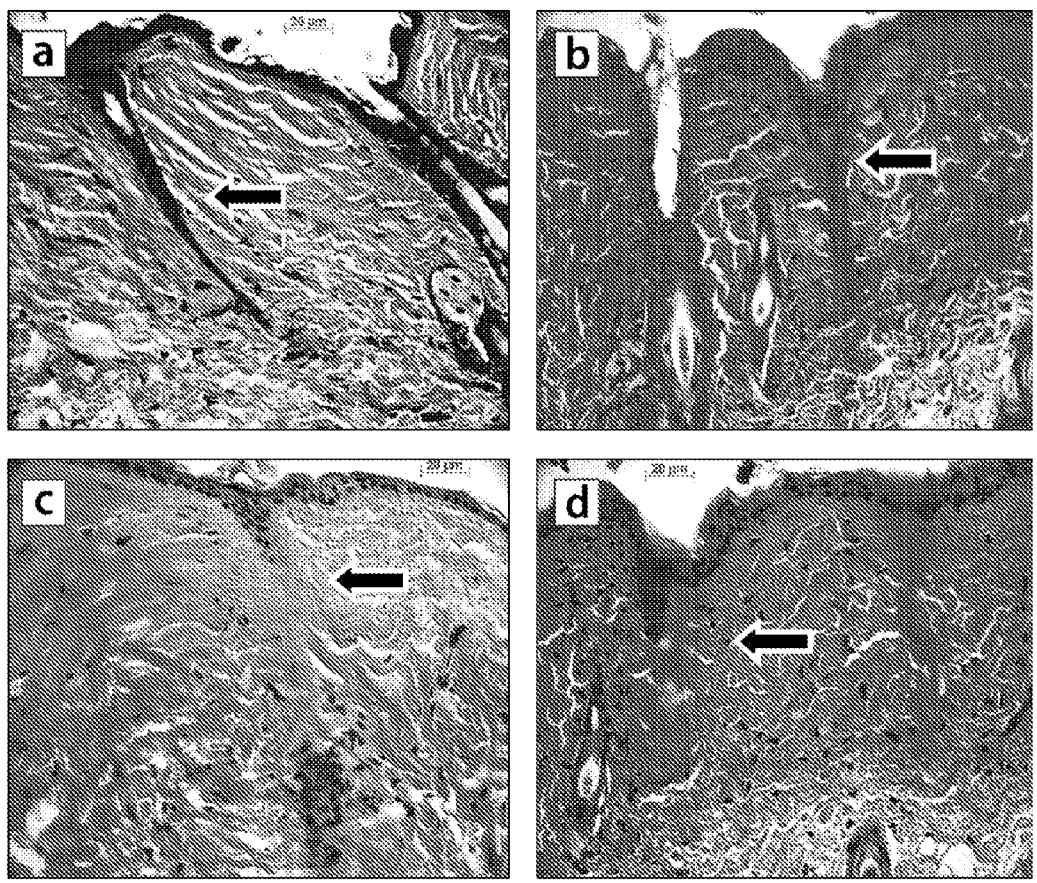
FIG. 10 illustrates PPARγ$^{fl/fl}$/cre mouse skin shows scarring. a) Dystrophic hair follicle with sebaceous gland atrophy b), c) & d) follicular scarring, in which fibrous connective tissue strands run perpendicular to the epidermis from remnants of dystrophic hair follicles, was found in PPARγ$^{fl/fl}$/cre mouse>4 months of age (H&E; 40×).

In advanced disease, the skin of PPARγ KO mice showed dystrophic hair follicles with sebaceous gland atrophy (FIG. 10a). Follicular scarring, in which fibrous connective tissue strands run perpendicular to the epidermis from remnants of dystrophic hair follicles, was also observed (FIGS. 10b, c & d). Microarray analysis of PPARγ KO mice confirmed the immunohistochemical data and showed a dramatic increase in gene expression of chemokines (MIP1a, MIP1b, CCR1, CD14), extracellular matrix associated proteins (MMP12, MMP8, TIMP2) and apoptosis-related genes (CASP3, DUSP11) (Table 4) suggesting the activation and involvement of Macrophages and T-lymphocytes. The data also suggest that apoptosis and substantial matrix remodeling may characterize the loss of hair follicles in PPARγ KO mice.

Figure 3:
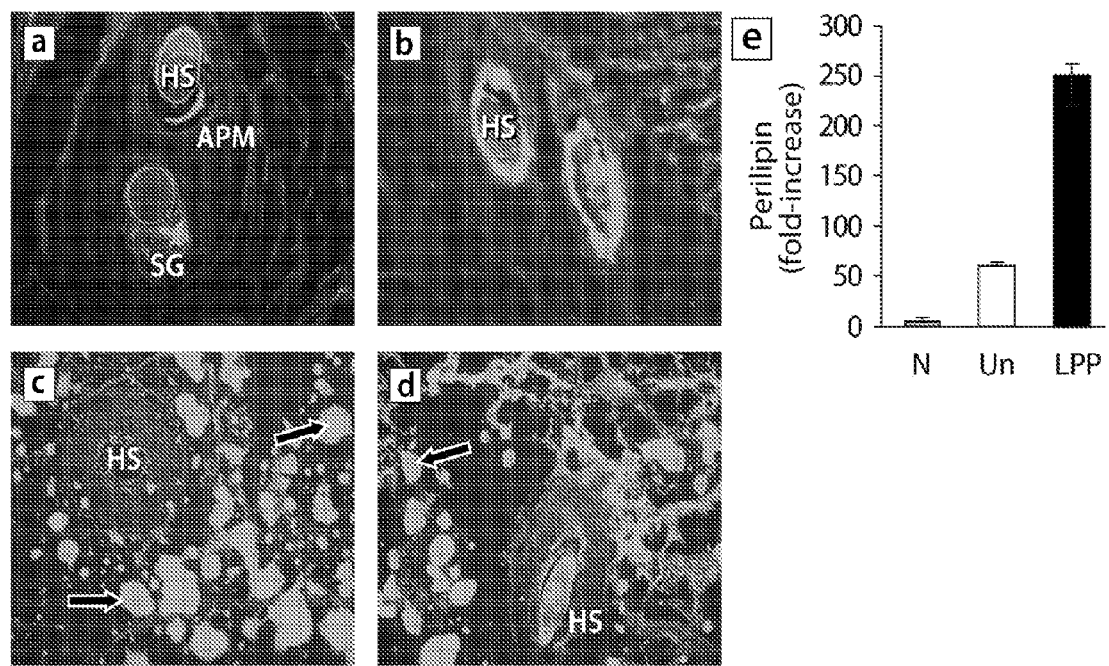
FIG. 3 illustrates lipid accumulation in LPP. Nile Red staining of a) normal, b) unaffected and c & d) LPP tissue. Droplets of lipids were seen in the perifollicular region of LPP tissue but not in normal scalp biopsy sections. b) Unaffected tissue showed intense lipid staining in the outer and inner root sheaths surrounding the hair shaft and less intense staining than affected LPP in the perifollicular region. HS-hair shaft, APM-arrector pili muscle, SG-sebaceous gland. Arrows indicate lipid droplets. e) To quantitate the lipid droplets, we measured gene expression changes of Perilipin A, a lipid droplet protein by real-time PCR. A five-fold increase in Perilipin gene expression is seen in affected compared to unaffected LPP which correlates with the lipid staining data.
Figure 11:
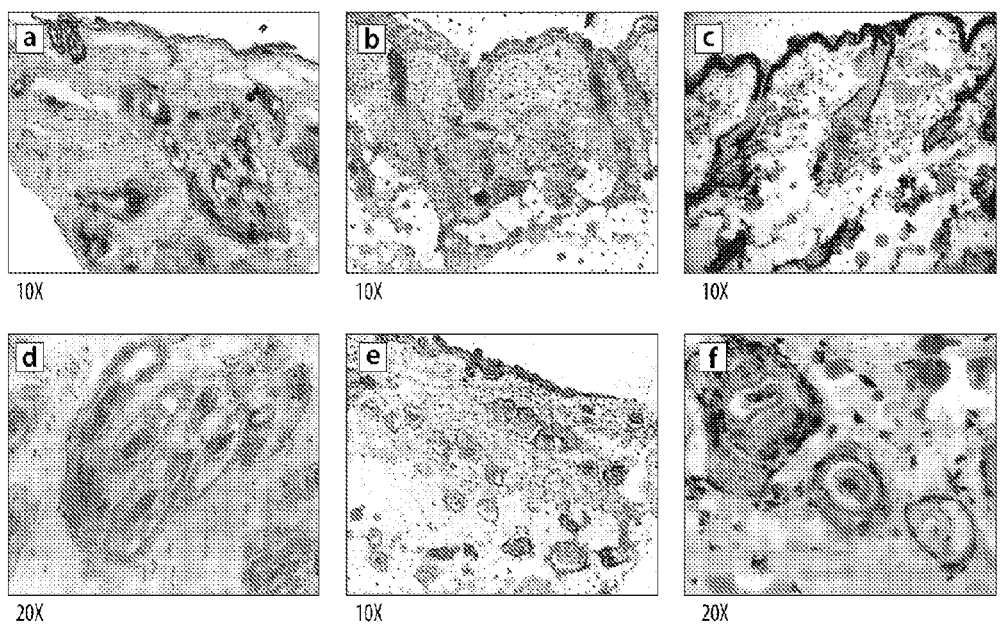
FIG. 11 illustrates follicular plugging in PPARγ$^{fl/fl}$/Cre mice caused by lipid accumulation. Oil Red staining of skin of PPARγ$^{fl/fl}$/Cre mice (b, c & e) show lipid accumulation in the follicular ostia and in the interstitial region f) at higher magnification (20×), horizontal sections show lipid accumulation around the hair shaft. a) & d) PPARγ$^{fl/fl}$ mice show little lipid accumulation around the hair shaft or in the interstitial region and the lipid staining is restricted to the sebaceous glands.

To determine if follicular plugging may be caused by deregulated lipid metabolism, we stained vertical and horizontal sections of skin biopsies of PPARγ KO mice with the lipid staining dye Oil Red 'O' (FIG. 11). Oil Red staining of skin sections revealed lipid accumulation in the follicular ostia, around the hair shaft and in the interstitial region of PPARg KO mice (FIGS. 11b, c, e and f). This is reminiscent of lipid accumulation seen in scalp biopsies of LPP patients (FIG. 3 and FIG. 14). In normal controls, the lipid staining was restricted to the sebaceous glands and there was very little interstitial lipid accumulation (FIGS. 11a and d). Intriguingly, as seen with LPP tissue, microarray data of PPARγ KO mice showed a sixty fourfold increase in expression of prostaglandin synthase (PTGS2 or COX2) and a ninety seven fold increase in the expression of the lipid oxidation enzyme 5-lipoxygenase (5-LO) activating protein (ALOX5AP) (Table 4). These data support the IPA data and suggests the existence of a negative feed-back loop between PPARγ and COX2 or ALOX5A.

TABLE 4

Upregulate transcripts in PPARγ KO mouse
Fold changes for each gene are shown in brackets

| | GO Biological Process/Molecular Pathway | Up-regulated transcripts in affected LLP | Number of genes affected |
|---|---|---|---|
| 1 | Immune Function | MIP2A (CXCL2) (111.5), MIP1a* (SCYA3)(97), CD14 (39.4), MIP3b (SCYA19)(9.2), CXCL14 (SCYB14)(5.66), MIP1b (SCYA4) (4.6), CCR1 (MIP1aR)(4) H2-D1 (119), B2M (34.3), H2-L (24.3), H2-Q6 (8) | 8 |
| 2 | Tissue remodeling | MMP12 (34.3,) MMP8 (5.66), TIMP2 (3.73) | 3 |

TABLE 4-continued

Upregulate transcripts in PPARγ KO mouse
Fold changes for each gene are shown in brackets

| | GO Biological Process/Molecular Pathway | Up-regulated transcripts in affected LLP | Number of genes affected |
|---|---|---|---|
| 3 | Apoptosis | CASP3 (20), DUSP11 (17) | 2 |
| 4 | Eicosanoid (Prostaglandins/Leukotrienes signaling) | PTGS2 (COX2)(64), ALOX5AP (97) | 2 |

The animal data confirms our observations in LPP tissue and suggest that the loss of PPARγ expression activates the proinflammatory lipid metabolic pathways that in turn induce the inflammatory response and permanent hair loss in scarring alopecia. The similarity in histopathology between the PPARγ KO mice and human LPP (perifollicular lymphocytic inflammation, fibrosis, scarring and permanent hair loss) suggests a crucial role for PPARγ in the pathogenesis of scarring alopecia.

Discussion

Primary cicatricial alopecias (CA) are viewed as immune disorders caused by an inflammatory attack on the stem cells of the bulge required for regeneration of follicles during the hair growth cycle (Stenn, K. S., Sundberg, J. P., and Sperling, L. C. 1999. Hair follicle biology, the sebaceous gland, and scarring alopecias. Arch Dermatol 135:973-974; Price V H. 2006. The Medical Treatment of Cicatricial Alopecia. Seminars in Cutaneous Medicine and Surgery 25: 56-59; Mirmirani, P., Willey, A., Headington, J. T., Stenn, K., McCalmont, T. H., and Price, V. H. 2005. Primary cicatricial alopecia: histopathologic findings do not distinguish clinical variants. J Am Acad Dermatol 52:637-643; Cotsarelis, G., and Millar, S. E. 2001. Towards a molecular understanding of hair loss and its treatment. Trends Mol Med 7:293-301). To understand the molecular pathogenesis of these poorly understood hair disorders, we carried out global gene expression analysis of paired unaffected and affected scalp biopsies from LPP patients compared to normal controls. The majority of up-regulated genes in affected LPP tissue were either required for tissue remodeling and apoptosis or were inflammatory genes as anticipated from histopathology. The microarray data also revealed decreased expression of multiple genes required for fatty acid β-oxidation, fatty acid desaturation, cholesterol biosynthesis and peroxisome biogenesis in LPP scalp tissue. Intriguingly, the increase in expression of inflammatory genes was seen in affected and not in unaffected tissue. In contrast, the decreased expression of lipid metabolic genes was seen to a greater extent in unaffected compared to affected LPP tissue. These data suggest that the lipid metabolic changes likely represent early or primary events in disease pathogenesis and do not simply reflect the loss of sebaceous glands. Our data also suggests that the lipid metabolic changes may be the cause rather than the effect of the inflammatory response in LPP. Lipid analysis by gas chromatography showed a significant increase in arachidonic acid in affected LPP compared to unaffected tissue, thereby raising the possibility of arachidonate metabolites such as leukotrienes and prostaglandins acting as proinflammatory signals in LPP.

Indeed, biochemical pathway and promoter analysis of the differentially regulated genes identified PPARγ as an upstream regulator of the changes in LPP. These data also revealed a negative regulatory loop between PPARγ and prostaglandin endoperoxide synthase 2 (COX2). We identified a similar negative feed-back loop between PPARγ and 5-lipoxygenase (data not shown). Interestingly, both COX2 and ALOX5AP are significantly upregulated in both LPP and in the PPARγ KO mouse suggesting a role for these pathways in the pathogenesis of scarring alopecia. The first rate-limiting step in the conversion of arachidonic acid to prostaglandins is catalyzed by PTGS2 (COX2), an enzyme that is associated with biologic events such as injury, inflammation, and proliferation. The 5-lipoxygenase activating protein (ALOX5AP) is necessary for activation of 5-lipoxygenase that converts arachidonic acid into leukotrienes, which are eicosanoid lipid mediators of inflammation. Thus, elevated COX2 and 5-LO may lead to the increased production and secretion of prostaglandins and leukotrienes.

We have shown that there is a significant decrease in expression of PPARγ but not PPARα or PPARδ in LPP. In vitro studies in cultured human keratinocytes showed that specific PPARγ agonists induced the expression of peroxisomal genes that are down-regulated in LPP. Finally, hair follicle stem cell specific deletion of PPARγ in mice causes scarring alopecia with symptoms that parallel human disease. Previous studies (Cotsarelis, G. 2007. Hair Follicle Stem Cells—Epithelial. S-1-B, Fifth International Congress on Hair Research, Vancouver) have shown that ablation of bulge cells using K15 thymidine kinase mice induces hair loss but not inflammation. However, our data shows that targeted knockout of PPARγ in the stem cells of the bulge causes scarring alopecia. These results demonstrate that it is the dysfunction of stem cells caused by loss of PPARγ signaling rather than the deletion of stem cells per se that likely triggers the pathogenesis of CA. Together, these data provide compelling evidence that PPARγ deficiency leads to the accumulation of proinflammatory lipids generated by 5-LO and COX2 pathways that trigger the pathogenesis of scarring alopecia.

Figure 12:
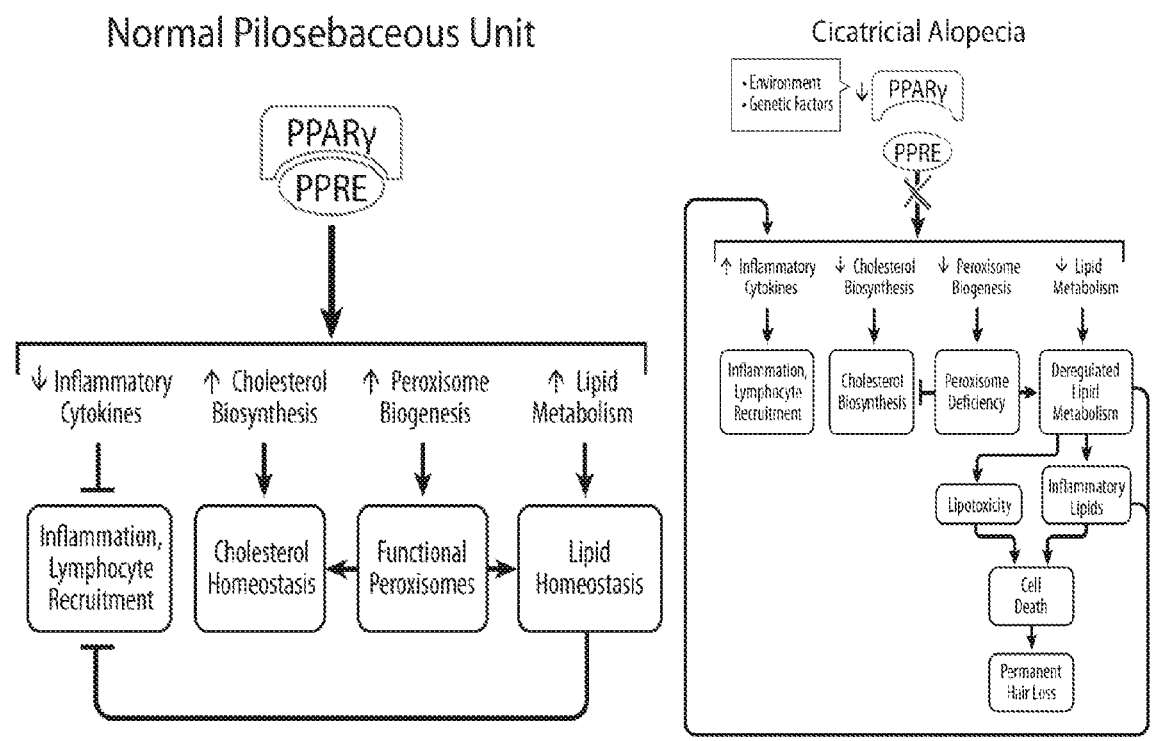
FIG. 12 illustrates the proposed model for the pathogenesis of primary cicatricial alopecia. In normal pilosebaceous units, PPARγ binds to PPAR response elements (PPRE) on target genes and maintains lipid homeostasis by regulating peroxisome biogenesis and lipid metabolism. PPARγ also modulates the inflammatory response by regulating the expression of cytokine genes. In primary CA, PPARg deficiency causes loss of peroxisome biogenesis, deregulates lipid metabolism and produces pro-inflammatory lipids that trigger an inflammatory response that in turn causes tissue damage and permanent hair loss in CA.

A likely model for pathogenesis of primary CA is shown (FIG. 12). In normal pilosebaceous units, PPARγ binds to PPRE and regulates peroxisome biogenesis and lipid metabolic genes thereby maintaining lipid homeostasis. PPARγ also has anti-inflammatory effects and modulates the inflammatory response by regulating the expression of proinflammatory lipid synthetic enzymes (COX2, 5-LO), cytokines, chemokines and adhesion molecules. In primary CA, environment, diet or genetic factors likely suppress PPARγ expression. The PPARγ deficiency or dysfunction in LPP patients induces peroxisome loss, disturbs lipid homeostasis and deregulates lipid metabolism in the pilosebaceous unit. This causes the accumulation of proinflammatory lipids that in turn trigger chemokine/cytokine expression, recruit lymphocytes and macrophages and causes tissue damage (lipotoxicity) and activates a lipid-mediated programmed cell death (lipoapoptosis) thereby contributing to permanent hair loss and scarring in LPP. Altered sebaceous and epidermal lipids have been suggested to be the cause of skin lesions seen in the Asebia mouse (Brown W R, Hardy M H. 1988. A hypothesis on the cause of chronic epidermal hyperproliferation in asebia mice. *Clin Exp Dermatol.* 13:74-77; Wilkinson D I, Karasek M A. 1966. Skin lipids of a normal and a mutant (asebic) mouse strain. J Invest Dermatol. 47:449-455; Sundberg J P, Boggess D, Sundberg B A, Eilertsen K, Parimoo S, Filippi M and Stenn K. 2000. Asebia-2J (Scd1ab2J): A New Allele and a Model for Scarring Alopecia. *Am J Path* 156: 2067-2075). Thus, the accumulation of proinflammatory lipids in the pilosebaceous units of LPP tissue and PPARγ KO mice may induce an inflammatory response due to lipotoxicity and contribute to CA pathogenesis. Recent studies (Wan Y, Saghatelian A, Chong L W, Zhang C L, Cravatt B F, Evans R M. 2007. Maternal PPAR gamma protects nursing neonates by suppressing the production of inflammatory milk. Genes Dev. 21:1895-908) have shown that PPARγ deficiency causes lipid accumulation in the lactating mammary gland. These studies also showed that PPARγ deficiency induces the production of inflammatory lipids in milk that causes alopecia in nursing pups.

The genetic or environmental mechanisms that initiate loss of PPARγ signaling in LPP are not understood. However, the skin as the outermost barrier of the body is exposed to various sources of environmental toxins such as dioxin or dioxin like compounds that are known to inhibit the expression of PPARγ and all lipogenic genes that are transcriptionally activated by PPARγ (Liu X and Jefcoate C. 2006 2,3,7,8-tetrachlorodibenzo-p-dioxin and EGF cooperatively suppress PPARg1 stimulation and restore focal adhesion complexes during adipogenesis: Selective contributions of Src, Rho and Erk distinguish these overlapping processes in C3H10T1/2 cells. Mol. Pharmacol. 70(6):1902-15). Dioxins exert their biologic effects via the aryl-hydrocarbon receptor (AhR), a ligand dependent transcription factor. Although epidemiologic or experimental links between dioxins and scarring alopecia are lacking, it is interesting to note that our microarray data showed the increased expression of dioxin-inducible Cytochrome P1-450 (CYP1A1) gene in both unaffected and affected LPP tissue (Table 1), suggesting the constitutive activation of AhR. Low-levels of dioxin exposure have become a focus of interest in the context of other PPARγ—involved diseases such as adult-onset diabetes (Remillard R B, Bunce N J. 2002. Linking dioxins to diabetes: epidemiology and biologic plausibility. Environ Health Perspect. 110: 853-8). Chronic low-dose exposure may cause the accumulation of dioxins in lipid-rich regions such as sebaceous glands and at a certain threshold level (which may be reached at middle-age) may cause the loss of PPARγ expression and scarring alopecia in susceptible individuals.

Whether the decrease in PPARγ expression in LPP is the result of exposure to an environmental toxin or is induced by dietary or genetic factors will require further study. However, activation of PPARγ signaling by PPAR agonists could be effective in alleviating the deleterious effects of inflammatory lipid accumulation in the pilosebaceous unit. Thiazolidinediones, that influence free fatty acid flux, are known to activate PPARγ (Berger, J. P., Akiyama, T. E., and Meinke, P. T. 2005. PPARs: therapeutic targets for metabolic disease. Trends Pharmacol Sci 26:244-251). Our data shows that rosiglitazone, ciglitazone, troglitazone and pioglitazone, induce the expression of peroxisomal gene expression in LPP. Thus, it seems likely that the stimulation of PPARγ-activity by specific agonists could potentially inhibit the deleterious effects of proinflammatory lipids such as inflammation, loss of hair follicles and scarring seen in LPP. Synthetic PPARγ ligands are currently used therapeutically in the treatment of dyslipidemias, type 2-diabetes, cardiovascular disease and metabolic syndrome (Morrison W R and Smith L M. 1964. Preparation of fatty acid methyl esters and dimethyl acetals from lipids with boron fluoride-methanol. J. Lipid Res. 5:600-8). Alternatively, specific inhibitors of 5-LO pathway or specific COX2 inhibitors may provide novel therapeutic strategies for the treatment of scarring alopecias.

In summary, we show here that the loss of PPARγ expression in the stem cells of the bulge results in progressive hair loss, sebaceous gland atrophy, scarring, and inflammation in a mouse model. These observations clearly implicate primary defects of PPARγ in the generation of scarring alopecia. We believe the human disorder is a consequence of PPARγ deficiency that in turn induces a series of changes in key metabolic pathways that induce the production of proinflammatory lipids. We have shown that perturbation of lipid metabolism induced by PPARγ deficiency, most likely an acquired condition, results in inflammation-induced destruction of the pilosebaceous gland in CA. These effects reveal a crucial role for PPARγ in the maintenance and normal functioning of the pilosebaceous unit and suggest that loss of this signaling pathway may be responsible for the pathogenesis of CA. This is the first report that suggests a link between PPARγ deficiency, deregulated lipid metabolism and hair disorders in humans.

These observations provide a novel framework for understanding the role of PPARγ in the pathophysiology of primary cicatricial alopecia. Indeed, PPARγ agonists may represent a potential new therapeutic strategy in the treatment of these disorders.

Methods

Human tissue. Scalp biopsies were obtained from patients with a clinical diagnosis of lymphocyte mediated lichen planopilaris (LPP) and who were seen at the clinics and University Hospitals of Cleveland. All patients had active disease with symptoms of itching, burning, or pain, and with progressive hair loss, positive pull test, and evidence of inflammation. Patients were 18 years or older and were able to give informed consent. These patients were evaluated in a standard manner. This evaluation included a medical history, detailed hair questionnaire, treatment history, examination of hair, scalp, and skin, scalp photographs, and two 4 mm scalp biopsies—one from affected and another from clinically unaffected scalp. Scalp biopsy specimens from healthy volunteers were included as controls. All biopsies were done under the approval of the Institutional Review Board and with appropriate consents of patients and volunteers. All tissue samples were stored at −80° C. until processed. These biopsies were utilized for total RNA extraction, microarray analysis, real-time PCR and immunofluorescence.

RNA isolation and Microarray analysis. Total RNA from each biopsy was extracted using Trizol (Life Technologies, Inc., Gaithersburg, Md., USA) as per the manufacturer's instructions, followed by purification using RNeasy Mini columns (Qiagen, Inc., Valencia, Calif., USA). The RNA was quantitated by spectrometry and used for microarray and realtime PCR experiments.

We analyzed samples of fresh frozen scalp tissue biopsied from patients with LPP (n=20, pooled) and compared the pattern of gene expression against normal (control) scalp tissue (n=20, pooled) by interrogating the Affymetrix GeneChip oligonucleotide array Human U133A 2.0 (Affymetrix, Santa Clara, Calif., USA). This array represents 18,400 transcripts and variants, including 14,500 well-characterized human genes. Fluorescent Cy3-or Cy5-labeled cDNA (Amersham Pharmacia Biotech) was synthesized from 50-100 µg total RNA, using oligo-dT-primed polymerization with SuperScript II reverse transcriptase (Life Technologies).

Hybridization to the oligonucleotide arrays and subsequent washing and detection was performed as described in the Affymetrix Expression Analysis Technical Manual (Affymetrix, Santa Clara, Calif., USA). Array images were acquired using a GeneChip Scanner 3000 (Affymetrix, Santa Clara, Calif., USA) and analysed with Genechip Operating Software (GCOS). The image from each GeneChip was scaled such that the average intensity value for all of the arrays is adjusted to a target intensity of 500 to take into account the inherent differences between the chips and their hybridization efficiencies. The Affymetrix program Netaffyx and the Online Mendelian Inheritance In Man (OMIM) were used to identify the functional significance, cellular location and the role of genes in various biological and metabolic processes.

Pathway analysis. Biologically relevant pathways were constructed using Ingenuity Pathways Analysis (IPA) application. The two gene lists, up-and down-regulated genes in LPP, were combined together and a final list containing Affymetrix identifiers and associated fold-change values were uploaded for IPA analysis. The genes which had a fold change greater than 2.0 were included in this analysis. Each gene identifier was mapped to its corresponding gene object in the Ingenuity Pathways Knowledge Base. These genes, called focus genes, were overlaid onto a global molecular network developed from information contained in the Ingenuity Pathways Knowledge Base. Networks of these focus genes were then algorithmically generated based on their connectivity. The Functional Analysis of a network identified the biological functions and/or diseases that were most significant to the genes in the network. Fischer's exact test was used to calculate a p-value determining the probability that each biological function and/or disease assigned to that data set is due to chance alone. The program also computes a score for each network according to the fit of the network to the set of focus genes.

Quantitative real-time RT-PCR. FAM labeled PCR primers and TaqMan hydrolysis probes for all target genes and 18S rRNA were purchased from Perkin-Elmer Applied Biosystems (Foster City, Calif.). Real-time PCR was performed on an ABI Prism 7700 Sequence Detection System (PE Biosystems) according to the recommendation of the manufacturer. The target gene expression in LPP and control samples was quantitated by the comparative CT method as described in the ABI Prism 7700 Sequence Detection System manual (PE Biosystems).

Immunohistochemistry. Scalp tissue specimens were cut horizontally or vertically and serial sections were prepared using a cryostat (Leica Microsystems Inc.). The slides were fixed in acetone and stored at −80° C. until immunostaining was performed. For the morphological detection of peroxisomes, horizontal and vertical sections of scalp biopsies were stained using the SelectFX Alexa Fluor 488 peroxisome labeling kit (Invitrogen-Molecular Probes) following the recommendation of the manufacturer and visualized by indirect immunofluorescence light microscopy. The kit utilizes rabbit antibodies directed against the peroxisomal membrane protein 70 (PMP 70), which is a high abundance integral-membrane component of peroxisomes. In some instances, the slides were counterstained with the nuclear stain DAPI. Antigen-antibody complexes were detected under a Carl Zeiss Axioskop FL microscope, using Alexa Fluor 488 goat anti-rabbit IgG antibody (Invitrogen-Molecular Probes). The approximate absorption and fluorescence emission peaks of the Alexa Fluor 488 dye conjugate are 495 nm and 519 nm and the labeling was observed using standard fluorescein filter sets. The slides were cover-slipped with Vectashield mounting medium (Vector Labs. Inc. Burlingame, Calif.). For immunofluorescence staining, frozen OCT sections were fixed in acetone for 10 min. and stained with rat anti-mouse F4/80 antigen, pan macrophage marker, 1:2000 for 1 h and binding was detected using the Vector ABC kit. For detection of T-lymphocytes, formalin fixed tissues were stained with DAKO, rabbit anti-human CD3 antigen which has been successfully used by NIH for mouse sections (DAKO) at 1:400 for 1 h.

Nile Red and Oil Red 'O' Fluorescent Staining. Stock solutions of Nile Red (Sigma Chemicals, St. Louis, Mo.) 1 mg/ml in DMSO were prepared and stored at −20° C. Slides containing vertical or horizontal sections of scalp biopsies were incubated in 0.5 μg/ml working solution of Nile red (Fowler, S. D., and Greenspan, P. Application of Nile red, a fluorescent hydrophobic probe, for the detection of neutral lipid deposits in tissue sections: comparison with oil red O. J Histochem Cytochem 33:833-836, (1985)) in PBS for 30 minutes, washed in PBS three times, rinsed with distilled water and cover-slipped with Crystal Mount (Biomedia, Foster City, Calif.). Tissue sections were assessed by Oil-Red-O staining of intracytoplasmic lipid droplets, essentially as described (Lillie R D and Ashburn L L. 1943. Supersaturated solutions of fat stains in dilute isopropanol for demonstration of acute fatty degeneration not shown by Herxheimer's technique. Archs. Path. 36,432). Oil-Red-O-stained cells were imaged by rinsing thoroughly with $H_2O$. The sections were examined under a Carl Zeiss Axioskop FL microscope.

Lipid analysis. Tissue lipids were extracted by the Folch method (Folch J, L. M., Soane G H. 1957. A simple method for the isolation and purification of total lipids from animal tissues. J Biol. Chem. 226: 497-509). The chloroform phase containing lipids was collected, dried under nitrogen and subjected to methylation. Fatty acid methyl esters were prepared by standard methods using BF3/methanol reagent (14% Boron Trifluoride). Fatty acid methyl esters were analyzed by gas chromatography using a fully automated HP5890 system equipped with a flameionization detector (J. Lipid Res. 5:600-8). The chromatography utilized an Omegawax 250 capillary column. Peaks were identified by comparison with fatty acid standards (Nu-chek-Prep, Elysian, Minn.), and the area and its percentage for each resolved peak were analyzed using a Perkin-Elmer M1 integrator.

Effect of PPARg agonists and antagonists on PEXgenes. Human Hair Follicle Outer Root Sheath Cells (ORS cells) were obtained from ScienCell™ (San Diego, Calif.) and grown in Mesenchymal Stem Cell Medium (MSCM) consisting of 500 ml of basal medium, 25 ml of fetal bovine serum, 5 ml of mesenchymal stem cell growth supplement and 5 ml of penicillin/streptomycin solution. HaCaT cells were cultured in Dulbecco's modified Eagle's medium containing 10% fetal bovine serum under 5% CO2 at 37° C. The different PPAR agonists were added in triplicate in dimethylsulfoxide (<0.1% by volume) for 48 hours to evaluate their effects on PEX gene expression by real-time PCR.

Generation of PPARγ stem cell KO mice. PPARγ stem cell KO mice (PPARγ (f/f)/Cre) mice were generated by intercrossing mice carrying floxed alleles of PPARγ (Cell 61:1329-1337) were crossed with a Cre-transgenic line K15-CrePR1 (BMC Bioinformatics 6:79) expressing Cre recombinase under the control of mouse keratin complex 1, acidic, gene 15 promoter. Both mouse strains were purchased from Jackson laboratories. Littermates lacking the K15-Cre transgene were used as controls. All experimental procedures were conducted in accordance with the Guide for care and Use of laboratory Animals of the national Institutes of Health, and were approved by the Case Western Reserve University IACUC.

PCR genotyping was carried out by using the following primers: for the Cre transgene, the following primers: oIMR1084 (5'-GCG GTC TGG CAG TAA AAA CTA TC-3') (SEQ. ID NO:1) and oIMR1085 (5'-GTG AAA CAG CAT TGC TGT CAC TT-3') (SEQ. ID NO:2) yields a 100 base pair fragment. For identifying the floxed allele, the following primers were used: oIMR1934 (5'-TGT AAT GGA AGGGCA AAA GG-3') (SEQ. ID NO:3) oIMR1935 (5'-TGG CTT CCA GTGCAT AAGTT-3') (SEQ. ID NO:4) amplify a 214 bp product from the wildtype and a 250 bp product from the mutant (floxed) allele. Genomic DNA was amplified by 35 cycles of 94° C. for 20 s, 60° C. for 30 s, and 72° C. for 55 s.

Total RNA isolated from mouse tissues by using TRIzol (Invitrogen). Reverse transcription was performed with SuperScript (Invitrogen). Sense (5'-GTCACGTTCTGA-CAGGACTGTGTGAC-3') (SEQ. ID NO:5) and antisense (5'-TATCACTGGAGATCTCCGCCAACAGC-3') (SEQ. ID NO:6) primers were designed to anneal to regions in exons A1 and 4 of PPARγ1, respectively, which distinguish the full-length (700-bp) and recombined (300-bp) transcripts. PCR was performed by 40 cycles of 94° C. for 20 s, 60° C. for 30 s, and 72° C. for 60 s.

Histochemistry. Tissues were fixed in Bouins' buffer and paraffin-embedded. Sections were subjected to standard hematoxylin/eosin staining. For oil red O staining, skin biopsies were embedded in OCT and cryosectioned.

EXAMPLE 2

Patients were treated with Actos (Pioglitazone), a PPARγ agonist that is currently used to treat diabetes.

Patients with LLP were given a low dose of Actos, i.e., less than about 15 mg/daily. All (5) patients reported a significant decrease in itching, burning and pain associated with lichen planopilaries. The histology of scalp biopsy of one of the patients before, after one year of treatment, and after two years of treatment are shown in FIGS. 18-20. At two years, there is complete clearing of inflammatory cells. Reduction is already seen after 1 year. Therefore, PPAR agonist is effective in reducing symptoms.

From the above description of the invention, those skilled in the art will perceive improvements, changes and modifications. Such improvements, changes and modifications within the skill of the art are intended to be covered by the appended claims. All patents, publications, and reference cited in the application are herein incorporated by reference in their entirety.

Having described the invention, the following is claimed:

1. A method of ameliorating lichen planopilaris in a subject, the method comprising the step of administering a therapeutically effective amount of at least one PPARγ agonist to the subject, wherein the PPARγ agonist inhibits or decreases peroxisome loss in at least one cell of the subject.

2. The method of claim 1, the PPARγ agonist or a derivative thereof comprising a compound of Formula I or pharmaceutically acceptable salt of a compound of Formula I, wherein Formula I is:

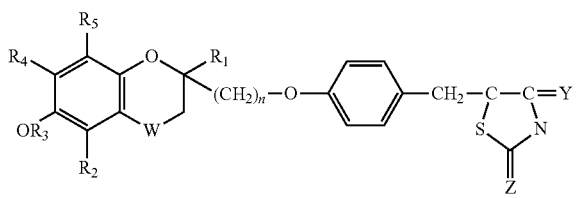

(I)

wherein $R_1$ and $R_2$ are the same or different, and each represents a hydrogen atom or a $C_1$-$C_5$ alkyl group;

$R_3$ represents a hydrogen atom, a $C_1$-$C_6$ aliphatic acyl group, an alicyclic acyl group, an aromatic acyl group, a heterocyclic acyl group, an araliphatic acyl group, a ($C_1$-$C_6$ alkoxy)carbonyl group, or an aralkyloxycarbonyl group;

$R_4$ and $R_5$ are the same or different, and each represents a hydrogen atom, a $C_1$-$C_6$ alkyl group or a $C_1$-$C_6$ alkoxy group, or $R_4$ and $R_5$ together represent a $C_1$-$C_6$ alkylenedioxy group;

n is 1, 2, or 3;

W represents the $CH_2$, CO, or $CHOR_6$ group in which $R_6$ represents any one of the atoms or groups defined for $R_3$; and Y and Z are the same or different and each represents an oxygen atom or an imino (—NH) group; and pharnaceutically acceptable salts thereof.

3. The method of claim 1, the PPARγ agonist or a derivative thereof comprising a compound of Formula II or pharmaceutically acceptable salt of a compound of Formula II, wherein Formula II is:

(II)

wherein $R_{11}$ is a substituted or unsubstituted alkyl, alkoxy, cycloalkyl, phenylalkyl, phenyl, aromatic acyl group, a 5- or 6-membered heterocyclic group including 1 or 2 heteroatoms selected from the group consisting of nitrogen, oxygen, and sulfur, or a group of the formula indicated in:

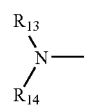

wherein $R_{13}$ and $R_{14}$ are the same or different and each is lower alkyl;

and wherein $L^1$ and $L^2$ are the same or different and each is hydrogen or lower alkyl or $L^1$ and $L^2$ are combined to form an alkylene group.

4. The method of claim 1, the PPARγ agonist or a derivative thereof comprising a compound of Formula III or pharmaceutically acceptable salt of a compound of Formula III, wherein Formula III is:

(III)

wherein $R_{15}$ and $R_{16}$ are independently hydrogen, lower alkyl containing 1 to 6 carbon atoms, alkoxy containing 1 to 6 carbon atoms, halogen, ethyl, nitrite, methylthio, trifluoromethyl, vinyl, nitro, or halogen substituted benzyloxy;

and n is 0 to 4.

5. The method of claim 1, the PPARγ agonist or a derivative thereof comprising a compound of Formula IV or pharmaceutically acceptable salt of a compound of Formula IV, wherein Formula IV is:

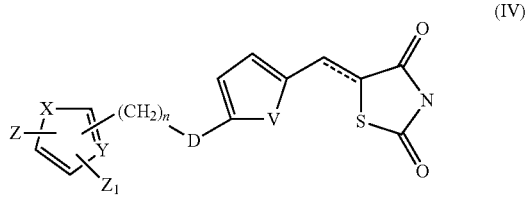

(IV)

wherein the dotted line represents a bond or no bond; V is HCH—, —NCH—, —CH=N—, or S;

D is $CH_2$, CHOH, CO, C=NOR$_{17}$, or CH=CH; X is S, SO, NR$_{18}$, —CH=N, or 13 N=CH;

Y is CH or N;

Z is hydrogen, $(C_1-C_7)$alkyl, $(C_1-C_7)$cycloalkyl, phenyl, naphthyl, pyridyl, furyl, thienyl, or phenyl mono- or di-substituted with the same or different groups which are $(C_1-C_3)$alkyl, trifluoromethyl,$(C_1-C_3)$alkoxy, fluoro, chloro, or bromo $Z_1$ is hydrogen or $(C_1-C_3)$alkyl;

$R_{17}$ and $R_{18}$ are each independently hydrogen or methyl; and n is 1, 2, or 3.

6. The method of claim 1, the PPARγ agonist or a derivative thereof comprising a compound of Formula V or pharmaceutically acceptable salt of a compound of Formula V, wherein Formula V is:

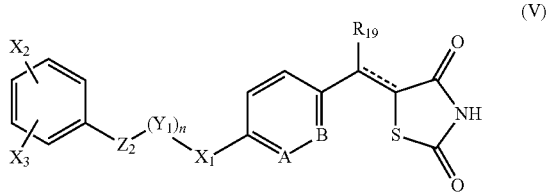

(V)

wherein the dotted line represents a bond or no bond;

A and B are each independently CH or N with the proviso that when A or B is N the other is CH; X is S, SO, $SO_2$, $CH_2$, CHOH, or CO;

n is 0 or 1;

$Y_1$ is CHR$_{20}$ or R$_{21}$, with the proviso that when n is 1 and $Y_1$ is NR$_{21}$, $X_1$is $SO_2$ or CO; $Z_2$ is CHR$_{22}$, $CH_2CH_2$, cyclic $C_2H_2O$, CH=CH, $OCH_2$, $SCH_2$, $SOCH_2$, or $SO_2CH_2$;

$R_{19}$, $R_{20}$, $R_{21}$, and $R_{22}$ are each independently hydrogen or methyl; and $X_2$ and $X_3$ are each independently hydrogen, methyl, trifluoromethyl, phenyl, benzyl, hydroxy, methoxy, phenoxy, benzyloxy, bromo, chloro, or fluoro.

7. The method of claim 1, the PPARγ agonist or a derivative thereof comprising a compound of Formula II or pharmaceutically acceptable salt of a compound of Formula VI, wherein Formula VI is:

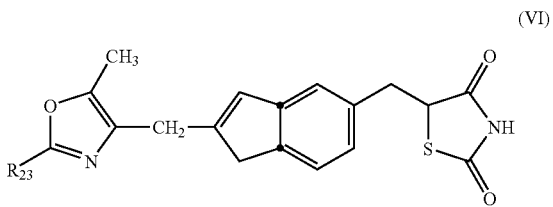

(VI)

wherein $R_{23}$ is alkyl of 1 to 6 carbon atoms, cycloalkyl of 3 to 7 carbon atoms, phenyl or mono- or all-substituted phenyl wherein the substituents are independently alkyl of 1 to 6 carbon atoms, alkoxy of 1 to 3 carbon atoms, halogen, or trifluoromethyl.

8. The method of claim 1, the PPARγ agonist or a derivative thereof comprising a compound of Formula VII or pharmaceutically acceptable salt of a compound of Formula VII, wherein Formula VII is:

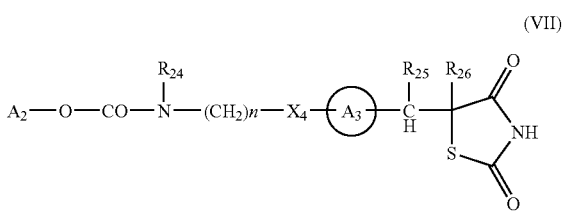

(VII)

wherein $A^2$ represents an alkyl group, a substituted or unsubstituted aryl group, or an aralkyl group wherein the alkylene or the aryl moiety is substituted or unsubstituted;

$A^3$ represents a benzene ring having in total up to 3 optional substituents;

$R_{24}$ represents a hydrogen atom, an alkyl group, an acyl group, an aralkyl group wherein the alkyl or the aryl moiety is substituted or unsubstituted, or a substituted or unsubstituted aryl group; or $A^2$ together with $R_{24}$ represents substituted or unsubstituted $C_{2-3}$ polymethylene group;

$R_{25}$ and $R_{26}$ each represent hydrogen, or $R_{25}$ and $R_{26}$ together represent a bond; $X_4$ represents O or S; and n represents an integer in the range from 2 to 6.

9. The method of claim 1, the PPARγ agonist or a derivative thereof comprising a compound of Formula VIII or pharmaceutically acceptable salt of a compound of Formula VIII, wherein Formula VIII is:

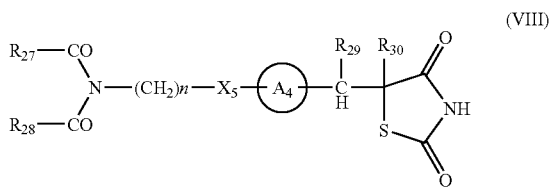

(VIII)

wherein: $R_{27}$ and $R_{28}$ each independently represent an alkyl group, a substituted or unsubstituted aryl group, or an aralkyl group being substituted or unsubstituted in the aryl or alkyl moiety;

or $R_{27}$ together with $R_{28}$ represents a linking group, the linking group consisting or an optionally substituted methylene group or an O or S atom; $R_{29}$ and $R_{30}$ each represent hydrogen, or $R_{29}$ and $R_{30}$ together represent a bond;

$A_4$ represents a benzene ring having in total up to 3 optional substituents;

$X_5$ represents O or S; and n represents an integer in the range of 2 to 6.

10. The method of claim 1, the PPARγ agonist or a derivative thereof comprising a compound of Formula IX or pharmaceutically acceptable salt of a compound of Formula IX, wherein Formula IX is:

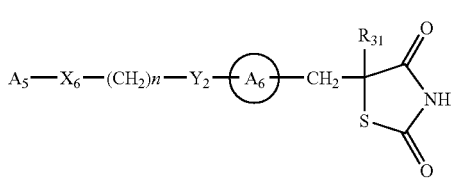

(IX)

wherein: $A_5$ represents a substituted or unsubstituted aromatic heterocyclyl group; $A_6$ represents a benzene ring having in total up to 5 substituents;

$X_6$ represents O, S, or N $R_{32}$ wherein $R_{32}$ represents a hydrogen atom, an alkyl group, an acyl group, an aralkyl group, wherein the aryl moiety may be substituted or unsubstituted, or a substituted or unsubstituted aryl group;

$Y_2$ represents O or S;

$R_{31}$ represents an alkyl, aralkyl, or aryl group; and n represents an integer in the range from 2 to 6.

11. The method of claim 1, the PPARγ agonist or a derivative thereof comprising a compound of Formula X or pharmaceutically acceptable salt of a compound of Formula X, wherein Formula X is:

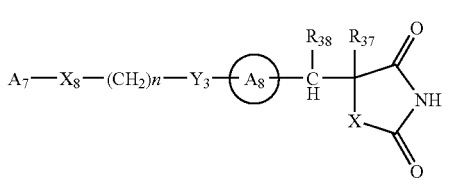

(X)

wherein: $A_7$ represents a substituted or unsubstituted aryl group;

$A_8$ represents a benzene ring having in total up to 5 substituents;

$X_8$ represents O, S, or N $R_9$, wherein $R_{39}$ represents a hydrogen atom, an alkyl group, an acyl group, an aralkyl group, wherein the aryl moiety may be substituted or unsubstituted, or a substituted or unsubstituted aryl group;

$Y_3$ represents O or S;

$R_{37}$ represents hydrogen;

$R_{38}$ represents hydrogen or an alkyl, aralkyl, or aryl group or $R_{37}$ together with $R_{38}$ represents a bond; and n represents an integer in the range from 2 to 6.

12. The method of claim 1, the PPARγ agonist or a derivative thereof comprising a compound of Formula II or pharmaceutically acceptable salt of a compound of Formula XI, wherein Formula XI is:

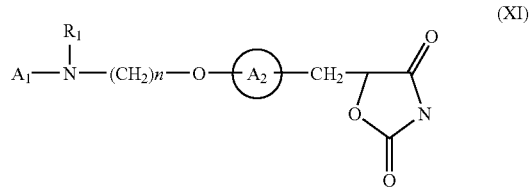

(XI)

wherein $A_l$ represents a substituted or unsubstituted aromatic heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$A^2$ represents a benzene ring having in total 1 up to 5 substituents; and n represents an integer in the range of from to 6.

13. The method of claim 1, the PPARγ agonist or a derivative thereof comprising a compound of Formula XII or Formula XIII or pharmaceutically acceptable salt of a compound of Formula XII or Formula XIII, wherein Formula XII and Formula XIII are:

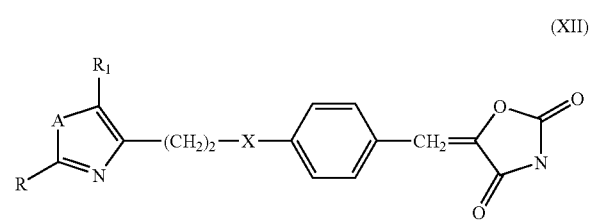

(XII)

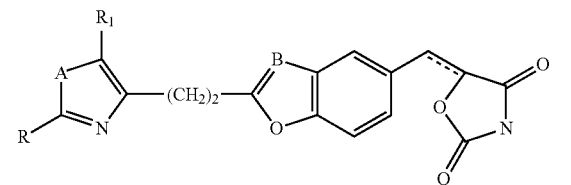

(XIII)

wherein the dotted line represents a bond or no bond;

R is cycloalkyl of three to seven carbon atoms, naphthyl, thienyl, furyl, phenyl, or substituted phenyl wherein the substituent is alkyl of one to three carbon atoms, alkoxy of one to three carbon atoms, trifluoromethyl, chloro, fluoro, or bis(trifluoromethyl);

R, is alkyl of one to three carbon atoms;

X is O or C=O;

A is O or S; and

B is N or CH.

14. The method of claim 1, the PPARγ agonist being locally administered to the subject and comprising at least one compound or a pharmaceutically salt thereof selected from the group consisting of:

(+)-5[[4-[(3,4-dihydro-6-hydroxy-2,5,7,8-tetramethyl-2H-1-benzopyran-2-yl)methoxy]phenyl]methyl]-2,4thiazolidinedione; 5-[4-[2-(5-ethylpyridin-2-yl)ethoxyl]benzyl]thiazolidine-2,4-dione; 5-[4-[(1-methylcyclohexyl)methoxy]benzyl]thiazolidine-2,4-dione; (ciglitazone); 4-(2-naphthylmethyl)-1,2,3,5- oxathiadiazole-2-oxide; 5-[4-[2-[(N-(benzoxazol-2-yl)-N-methylamino]ethoxy]benzyl]-5-methlthiazolidine-2,4-dione; 5-[4-[2-[2,4dioxo-5-phenylthiazolidine-3-yl)ethoxy]benzyl]thiazolidine-2,4- dione; 5-[4[2-[(N-methyl-N-(phenoxycarbonyl)amino]ethoxy]benzyl]thiazolidine-2,4- dione; 5-[4-[2-phenoxyethoxy)benzyl]thiazolidine-2,4-dione; 5-[4-[2-(4-chorophenyl)ethylsulfonyl]benzyl]thiazolidine-2,4-dione; 5-[4-[3-(5-methyl-2-phenyloxazol-4-yl)propionyl]benzyl]thiazolidine-2,4-dione; 5-[[4-(3-hydroxy-1-methylcyclohexyl)methoxy]benzyl]thiazolidine-2,4-dione; 5-[4-[2-(5-methyl-2-phenyloxazol-4-yl)ethoxyl]benzyl]thiazolidine-2,4-dione; 5-[(2-benzyl-2,3-dihydrobenzopyran)-5-ylmethyl]thiazolidine-2,4-dione; 5-[[2-(2-naphthylmethyl)benzoxazol]-5-ylmethyl]thiazolidine-2,4-dione; 5-[4-[2-(3-phenylureido)ethoxyl]benzyl]thiazolidine-2,4-dione; 5-[4-[2-(N-benzoxazol-2-yl)-N-metholamino]ethoxy]benzyl]thiazolidine-2,4-dione; 5-[4[3-(5-methyl-2-phenyloxazol-4yl)propiony]benzyl]thiazolidine-2,4-dione; 5-[2-(5-methyl-2-phenyloxazol-4-ylmethyl)benzofuran-5-ylmethyl]oxazolidine-2,4-dione; 5-[4-[2-(N-methyl-N-(2-pyridyl)amino]ethoxy]benzyl]thiazolidine-2,4-dione; and 5-[4-[2-(N-(benzoxazol-2-yl)-N-methylamino]ethoxy]benzyl]oxazolidine2,4-dione.

15. The method of claim 14, the at least one PPARγ agonist inhibits or decreases lipid accumulation in at least one pilosebaceous unit in the subject.

16. A method of ameliorating lichen planopilaris in a subject, the method comprising the step of topically administering to the subject a therapeutically effective amount of at least one PPARγagonist, wherein the PPARγ agonist inhibits or decreases peroxisome loss in at least one cell of the subject.

17. The method of claim 1, the PPARγ agonist or a derivative thereof comprising a compound of Formula I or pharmaceutically acceptable salt of a compound of Formula I, wherein Formula I is:

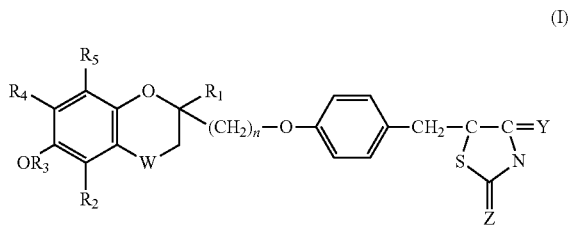

(I)

wherein $R_1$ and $R_2$ are the same or different, and each represents a hydrogen atom or a $C_1$-$C_5$ alkyl group;

$R_3$ represents a hydrogen atom, a $C_1$-$C_6$ aliphatic acyl group, an alicyclic acyl group, an aromatic acyl group, a heterocyclic acyl group, an araliphatic acyl group, a ($C_1$-$C_6$ alkoxy)carbonyl group, or an aralkyloxycarbonyl group;

$R_4$ and $R_5$ are the same or different, and each represents a hydrogen atom, a $C_1$-$C_5$ alkyl group or a $C_1$-$C_5$ alkoxy group, or $R_4$ and $R_5$ together represent a $C_1$-$C_5$ alkylenedioxy group;

n is 1, 2, or 3;

W represents the $CH_2$, CO, or $CHOR_6$ group in which $R_6$ represents any one of the atoms or groups defined for $R_3$; and Y and Z are the same or different and each represents an oxygen atom or an imino (—NH) group; and phamaceutically acceptable salts thereof.

18. The method of claim 16, the PPARγ agonist or a derivative thereof comprising a compound of Formula II or pharmaceutically acceptable salt of a compound of Formula II, wherein Formula II is:

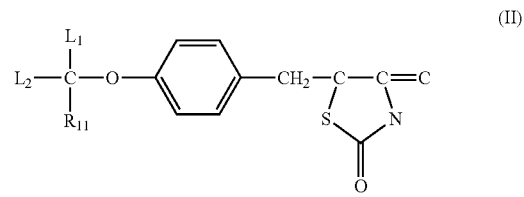

(II)

wherein $R_{11}$ is a substituted or unsubstituted alkyl, alkoxy, cycloalkyl, phenylalkyl, phenyl, aromatic acyl group, a 5- or 6-membered heterocyclic group including 1 or 2 heteroatoms selected from the group consisting of nitrogen, oxygen, and sulfur, or a group of the formula indicated in:

wherein $R_{13}$ and $R_{14}$ are the same or different and each is lower alkyl;

and wherein $L^1$ and $L^2$ are the same or different and each is hydrogen or lower alkyl or $L^1$ and $L^2$ are combined to form an alkylene group.

19. method of claim 16, the PPARγ agonist or a derivative thereof comprising a compound of Formula III or pharmaceutically acceptable salt of a compound of Formula III, wherein Formula III is:

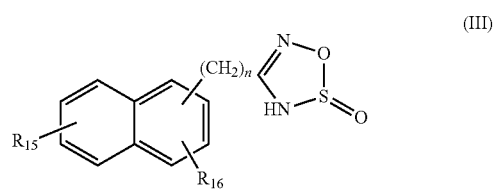

(III)

wherein $R_{15}$ and $R_{16}$ are independently hydrogen, lower alkyl containing 1 to 6 carbon atoms, alkoxy containing 1 to 6 carbon atoms, halogen, ethyl, nitrite, methylthio, trifluoromethyl, vinyl, nitro, or halogen substituted benzyloxy;

and n is 0 to 4.

20. The method of claim 16, the PPARγ agonist or a derivative thereof comprising a compound of Formula IV or pharmaceutically acceptable salt of a compound of Formula IV, wherein Formula IV is:

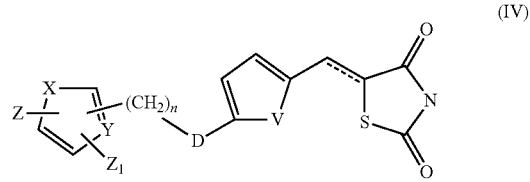

(IV)

wherein the dotted line represents a bond or no bond; V is HCH—, —NCH—, —CH=N—, or S;

D is $CH_2$, CHOH, CO, C=$NOR_{17}$, or CH=CH; X is S, SO, $NR_{18}$, —CH=N, or —N=CH;

Y is CH or N;

Z is hydrogen, ($C_1$-$C_7$)alkyl, ($C_1$-$C_7$)cycloalkyl, phenyl, naphthyl, pyridyl, furyl, thienyl, or phenyl mono- or di-substituted with the same or different groups which are ($C_1$-$C_3$)alkyl, trifluoromethyl,($C_1$-$C_3$)alkoxy, fluoro, chloro, or bromo $Z_1$ is hydrogen or ($C_1$-$C_3$)alkyl;

$R_{17}$ and $R_{18}$ are each independently hydrogen or methyl; and n is 1, 2, or 3.

21. The method of claim 16, the PPARγ agonist or a derivative thereof comprising a compound of Formula V or pharmaceutically acceptable salt of a compound of Formula V, wherein Formula V is:

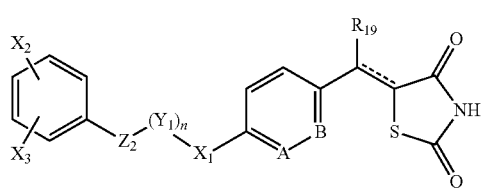

wherein the dotted line represents a bond or no bond;

A and B are each independently CH or N with the proviso that when A or B is N the other is CH; X is S, SO, $SO_2$, $CH_2$, CHOH, or CO;

n is 0 or 1;

$Y_1$ is $CHR_{20}$ or $R_{21}$, with the proviso that when n is 1 and $Y_1$ is $NR_{21}$, $X_1$ is $SO_2$ or CO; $Z_2$ is $CHR_{22}$, $CH_2CH_2$, cyclic $C_2H_2O$, CH=CH, $OCH_2$, $SCH_2$, $SOCH_2$, or $SO_2CH_2$;

$R_{19}$, $R_{20}$, $R_{21}$, and $R_{22}$ are each independently hydrogen or methyl; and $X_2$ and $X_3$ are each independently hydrogen, methyl, trifluoromethyl, phenyl, benzyl, hydroxy, methoxy, phenoxy, benzyloxy, bromo, chloro, or fluoro.

22. The method of claim 16, the PPARγ agonist or a derivative thereof comprising a compound of Formula II or pharmaceutically acceptable salt of a compound of Formula VI, wherein Formula VI is:

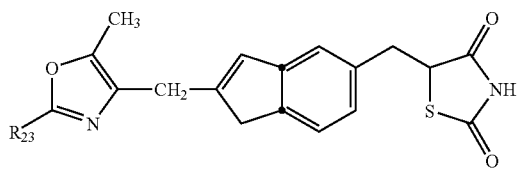

wherein $R_{23}$ is alkyl of 1 to 6 carbon atoms, cycloalkyl of 3 to 7 carbon atoms, phenyl or mono- or all-substituted phenyl wherein the substituents are independently alkyl of 1 to 6 carbon atoms, alkoxy of 1 to 3 carbon atoms, halogen, or trifluoromethyl.

23. The method of claim 16, the PPARγ agonist or a derivative thereof comprising a compound of Formula VII or pharmaceutically acceptable salt of a compound of Formula VII, wherein Formula VII is:

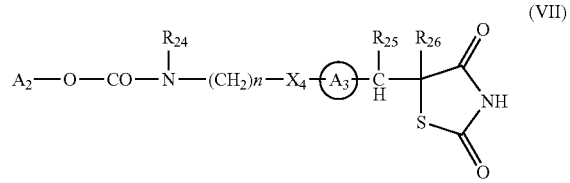

wherein $A^2$ represents an alkyl group, a substituted or unsubstituted aryl group, or an aralkyl group wherein the alkylene or the aryl moiety is substituted or unsubstituted;

$A^3$ represents a benzene ring having in total up to 3 optional substituents;

$R_{24}$ represents a hydrogen atom, an alkyl group, an acyl group, an aralkyl group wherein the alkyl or the aryl moiety is substituted or unsubstituted, or a substituted or unsubstituted aryl group; or $A^2$ together with $R_{24}$ represents substituted or unsubstituted $C_{2-3}$ polymethylene group;

$R_{25}$ and $R_{26}$ each represent hydrogen, or $R_{25}$ and $R_{26}$ together represent a bond; $X_4$ represents O or S; and n represents an integer in the range from 2 to 6.

24. The method of claim 16, the PPARγ agonist or a derivative thereof comprising a compound of Formula VIII or pharmaceutically acceptable salt of a compound of Formula VIII, wherein Formula VIII is:

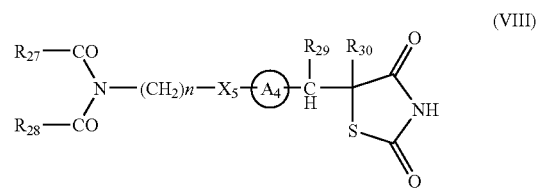

wherein: $R_{27}$ and $R_{28}$ each independently represent an alkyl group, a substituted or unsubstituted aryl group, or an aralkyl group being substituted or unsubstituted in the aryl or alkyl moiety;

or $R_{27}$ together with $R_{28}$ represents a linking group, the linking group consisting or an optionally substituted methylene group or an O or S atom; $R_{29}$ and $R_{30}$ each represent hydrogen, or $R_{29}$ and $R_{30}$ together represent a bond;

$A_4$ represents a benzene ring having in total up to 3 optional substituents;

$X_5$ represents O or S; and n represents an integer in the range of 2 to 6.

25. The method of claim 16, the PPARγ agonist or a derivative thereof comprising a compound of Formula IX or pharmaceutically acceptable salt of a compound of Formula IX, wherein Formula IX is:

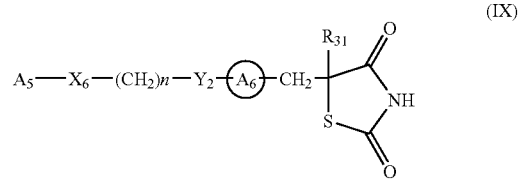

wherein: $A_5$ represents a substituted or unsubstituted aromatic heterocyclyl group; $A_6$ represents a benzene ring having in total up to 5 substituents;

$X_6$ represents O, S, or N $R_{32}$ wherein $R_{32}$ represents a hydrogen atom, an alkyl group, an acyl group, an aralkyl group, wherein the aryl moiety may be substituted or unsubstituted, or a substituted or unsubstituted aryl group;

$Y_2$ represents O or S;

$R_{31}$ represents an alkyl, aralkyl, or aryl group; and n represents an integer in the range from 2 to 6.

26. The method of claim 16, the PPARγ agonist or a derivative thereof comprising a compound of Formula X or pharmaceutically acceptable salt of a compound of Formula X, wherein Formula X is:

$$A_7-X_8-(CH_2)n-Y_3-A_8 \quad (X)$$

wherein: $A_7$ represents a substituted or unsubstituted aryl group;

$A_8$ represents a benzene ring having in total up to 5 substituents;

$X_8$ represents O, S, or N $R_9$, wherein $R_{39}$ represents a hydrogen atom, an alkyl group, an acyl group, an aralkyl group, wherein the aryl moiety may be substituted or unsubstituted, or a substituted or unsubstituted aryl group;

$Y_3$ represents O or S;

$R_{37}$ represents hydrogen;

$R_{38}$ represents hydrogen or an alkyl, aralkyl, or aryl group or $R_{37}$ together with $R_{38}$ represents a bond; and n represents an integer in the range from 2 to 6.

27. The method of claim 16, the PPARγ agonist or a derivative thereof comprising a compound of Formula II or pharmaceutically acceptable salt of a compound of Formula XI, wherein Formula XI is:

$$A_1-N(R_1)-(CH_2)n-O-A_2-CH_2 \quad (XI)$$

wherein $A_l$ represents a substituted or unsubstituted aromatic heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$A^2$ represents a benzene ring having in total 1 up to 5 substituents; and n represents an integer in the range of from to 6.

28. The method of claim 16, the PPARγ agonist or a derivative thereof comprising a compound of Formula XII or Formula XIII or pharmaceutically acceptable salt of a compound of Formula XII or Formula XIII, wherein Formula XII and Formula XIII are:

$$ (XII) $$

$$ (XIII) $$

wherein the dotted line represents a bond or no bond;

R is cycloalkyl of three to seven carbon atoms, naphthyl, thienyl, furyl, phenyl, or substituted phenyl wherein the substituent is alkyl of one to three carbon atoms, alkoxy of one to three carbon atoms, trifluoromethyl, chloro, fluoro, or bis(trifluoromethyl);

$R_1$ is alkyl of one to three carbon atoms;

X is O or C=O;

A is O or S; and

B is N or CH.

29. The method of claim 16, the PPARγagonist comprises at least one compound or a pharmaceutically salt thereof selected from the group consisting of:

(+)-5 [[4-[(3,4-dihydro-6-hydroxy-2,5,7,8-tetramethyl-2H-1-benzopyran-2-yl)methoxy]phenyl]methyl]-2,4thiazolidinedione; 5-[4-[2-(5-ethylpyridin-2-yl)ethoxyl]benzyl]thiazolidine-2,4-dione; 5-[4-[(1-methylcyclohexyl)methoxy]benzyl]thiazolidine-2,4-dione; (ciglitazone); 4-(2-naphthylmethyl)-1,2,3,5-oxathiadiazole-2-oxide; 5-[4-[2-[(N-(benzoxazol-2-yl)-N-methylamino]ethoxy]benzyl]-5-methlthiazolidine-2,4-dione; 5-[4-[2[2,4dioxo-5-phenylthiazolidine-3-yl)ethoxy]benzyl]thiazolidine-2,4-dione; 5-[4-[2-[(N-methyl-N-(phenoxycarbonyl)amino]ethoxy]benzyl]thiazolidine-2,4-dione; 5-[4-[2-phenoxyethoxy)benzyl]thiazolidine-2,4-dione; 5-[4-[2-(4-choropheny)ethylsulfonyl]benzyl]thiazolidine-2,4-dione; 5-[4-[3-(5-methyl-2-phenyloxazol-4-yl)propionyl]benzyl]thiazolidine-2,4-dione; 5-[[4-(3-hydroxy-1-methylcyclohexyl)methoxy]benzyl]thiazolidine-2,4-dione; 5-[4-[2-(5-methyl-2-phenyloxazol-4-yl)ethoxyl]benzyl]thiazolidine-2,4-dione ; 5-[(2-benzyl-2,3-dihydrobenzopyran)-5-ylmethyl]thiazolidine-2,4-dione; 5-[2-(2-naphthylmethyl)benzoxazol]-5-ylmethyl]thiazolidine-2,4-dione; 5-[4-[2-(3-phenylureido)ethoxyl]benzyl]thiazolidine-2,4-dione; 5-[4-[2-(N-benzoxazol-2-yl)-N-metholamino]ethoxy]benzyl]thiazolidine-2,4-dione; 5-[4-[3-(5-methyl-2-phenyloxazol-4-yl)propionyl]benzyl]thiazolidine-2,4-dione; 5-[2-(5-methyl-2-phenyloxazol-4-ylmethyl)benzofuran5-ylmethyl]oxazolidine-2,4dione; 5-[4-[2-(N-methyl-N-(2-pyridyl)amino]ethoxy]benzyl]thiazolidine-2,4-dione; and 5-[4-[2-(N-(benzoxazol-2-yl)-N-methylamino]ethoxy]benzyl]oxazolidine-2,4-dione.

30. The method of claim 16, the at least one PPARγ agonist inhibits or decreases lipid accumulation in at least one pilosebaceous unit in the subject.

\* \* \* \* \*

```
                        SEQUENCE LISTING

<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
gcggtctggc agtaaaaact atc                                              23

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
gtgaaacagc attgctgtca ctt                                              23

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tgtaatggaa gggcaaaagg                                                  20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
```

```
tggcttccag tgcataagtt                                               20

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
gtcacgttct gacaggactg tgtgac                                        26

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
tatcactgga gatctccgcc aacagc                                        26
```